US010485844B2

(12) United States Patent
Radin et al.

(10) Patent No.: US 10,485,844 B2
(45) Date of Patent: Nov. 26, 2019

(54) METHODS FOR TREATING SEVERE ATOPIC DERMATITIS BY ADMINISTERING AN IL-4R INHIBITOR

(71) Applicants: Regeneron Pharmaceuticals, Inc., Tarrytown, NY (US); Sanofi Biotechnology, Paris (FR)

(72) Inventors: Allen Radin, New York, NY (US); Neil Graham, Croton-on-Hudson, NY (US); Bolanle Akinlade, White Plains, NY (US); Gianluca Pirozzi, Bridgewater, NJ (US); Xing Sun, Bridgewater, NJ (US); Thomas Hultsch, Bridgewater, NJ (US); Brad S. Shumel, Chappaqua, NY (US); Ashish Bansal, White Plains, NY (US)

(73) Assignees: Regeneron Pharmaceuticals, Inc., Tarrytown, NY (US); Sanofi Biotechnology, Paris (FR)

( * ) Notice: Subject to any disclaimer, the term of this patent is extended or adjusted under 35 U.S.C. 154(b) by 0 days.

(21) Appl. No.: 15/711,815

(22) Filed: Sep. 21, 2017

(65) Prior Publication Data

US 2018/0078603 A1 Mar. 22, 2018

Related U.S. Application Data

(60) Provisional application No. 62/397,988, filed on Sep. 22, 2016, provisional application No. 62/442,083, filed on Jan. 4, 2017, provisional application No. 62/443,819, filed on Jan. 9, 2017, provisional application No. 62/445,774, filed on Jan. 13, 2017, provisional application No. 62/519,896, filed on Jun. 15, 2017.

(30) Foreign Application Priority Data

Aug. 18, 2017 (EP) .................... 17306081

(51) Int. Cl.
| | |
|---|---|
| A61K 38/02 | (2006.01) |
| A61K 39/395 | (2006.01) |
| A61K 45/06 | (2006.01) |
| A61P 17/00 | (2006.01) |
| C07K 16/28 | (2006.01) |
| A61K 9/00 | (2006.01) |
| C07K 7/06 | (2006.01) |
| C07K 16/24 | (2006.01) |
| A61K 39/00 | (2006.01) |

(52) U.S. Cl.
CPC ............ *A61K 38/02* (2013.01); *A61K 9/0019* (2013.01); *A61K 45/06* (2013.01); *A61P 17/00* (2018.01); *C07K 7/06* (2013.01); *C07K 16/247* (2013.01); *C07K 16/2866* (2013.01); *A61K 39/395* (2013.01); *A61K 2039/505* (2013.01); *A61K 2039/54* (2013.01); *A61K 2039/545* (2013.01); *C07K 2317/21* (2013.01)

(58) Field of Classification Search
None
See application file for complete search history.

(56) References Cited

U.S. PATENT DOCUMENTS

| 5,599,905 | A  | 2/1997  | Mosley |
| 5,714,146 | A  | 2/1998  | Lewis |
| 5,717,072 | A  | 2/1998  | Mosley |
| 5,856,296 | A  | 1/1999  | Mosley |
| 5,985,280 | A  | 11/1999 | Ritter |
| 6,156,877 | A  | 12/2000 | Ritter |
| 6,391,581 | B1 | 5/2002  | Mosley |
| 6,548,655 | B1 | 4/2003  | Mosley |
| 6,716,587 | B2 | 4/2004  | Mosley |
| 7,141,653 | B2 | 11/2006 | Greenfeder |
| 7,186,809 | B2 | 3/2007  | Pluenneke |
| 7,317,090 | B2 | 1/2008  | Mosley |
| 7,422,742 | B2 | 9/2008  | Greenfeder |
| 7,531,169 | B2 | 5/2009  | Singh |
| 7,605,237 | B2 | 10/2009 | Stevens |
| 7,608,693 | B2 | 10/2009 | Martin |
| 7,794,717 | B2 | 9/2010  | Stevens |
| 8,030,003 | B2 | 10/2011 | Rothenberg |
| 8,075,887 | B2 | 12/2011 | Martin |
| 8,075,895 | B2 | 12/2011 | Spertini |
| 8,092,802 | B2 | 1/2012  | Stevens |
| 8,092,804 | B2 | 1/2012  | Eriksson |

(Continued)

FOREIGN PATENT DOCUMENTS

| EP | 0604693 | 7/1994 |
| EP | 0367566 | 5/1997 |

(Continued)

OTHER PUBLICATIONS

Vakharia et al, Bio Drugs (2017) 31:409-422.*

(Continued)

*Primary Examiner* — Bridget E Bunner
*Assistant Examiner* — Fozia Hamud

(57) ABSTRACT

The present invention provides methods for treating moderate-to-severe or severe atopic dermatitis (AD). The methods of the present invention comprise administering to a subject in need thereof one or more doses of an interleukin-4 receptor (IL-4R) inhibitor such as an anti-IL-4R antibody. In certain embodiments, the methods of the present invention are used to treat severe AD in a patient whose disease is not controlled with systemic therapy (e.g., cyclosporine A) or when such therapy is inadvisable.

57 Claims, No Drawings
Specification includes a Sequence Listing.

(56) References Cited

U.S. PATENT DOCUMENTS

| | | |
|---|---|---|
| 8,252,284 B2 | 8/2012 | Singh |
| 8,324,192 B2 | 12/2012 | Dohil |
| 8,337,839 B2 | 12/2012 | Martin |
| 8,338,135 B2 | 12/2012 | Stevens |
| 8,497,528 B2 | 7/2013 | Lee |
| 8,604,171 B2 | 12/2013 | Singh |
| 8,637,239 B2 | 1/2014 | Furuta |
| 9,290,574 B2 | 3/2016 | Kostic |
| 2003/0103938 A1 | 6/2003 | Jinquan |
| 2003/0113387 A1 | 6/2003 | Tsuchida et al. |
| 2003/0124121 A1 | 7/2003 | Pluenneke |
| 2005/0031609 A1 | 2/2005 | Hultsch |
| 2005/0074462 A1 | 4/2005 | Holmgren |
| 2005/0118176 A1 | 6/2005 | Mosley |
| 2005/0255532 A1 | 11/2005 | Ruben |
| 2005/0282181 A1 | 12/2005 | Yan |
| 2006/0013811 A1 | 1/2006 | Dina |
| 2007/0041976 A1 | 2/2007 | Pluenneke |
| 2007/0274996 A1 | 11/2007 | Carter |
| 2008/0054606 A1 | 5/2008 | Eriksson |
| 2009/0074793 A1 | 3/2009 | Martin |
| 2009/0098142 A1 | 4/2009 | Kasaian |
| 2009/0264392 A1 | 10/2009 | Warndahl |
| 2010/0047254 A1 | 2/2010 | Martin |
| 2011/0195500 A1 | 8/2011 | Rothenberg |
| 2012/0004205 A1 | 1/2012 | Rothenberg |
| 2012/0052072 A1 | 3/2012 | Martin |
| 2012/0164080 A1 | 6/2012 | Hill |
| 2012/0207815 A1 | 8/2012 | Benhamou |
| 2013/0052190 A1 | 2/2013 | Collins |
| 2013/0078675 A1 | 3/2013 | Martin |
| 2013/0324435 A1 | 12/2013 | Rothenberg |
| 2014/0072583 A1 | 3/2014 | Ardeleanu |
| 2014/0187523 A1 | 7/2014 | Dohil |
| 2014/0271681 A1 | 9/2014 | Martin |
| 2014/0356372 A1 | 12/2014 | Stahl |
| 2015/0185228 A1 | 7/2015 | Reisacher |
| 2015/0246973 A1 | 9/2015 | Graham |
| 2016/0152718 A1 | 6/2016 | Kostic |
| 2017/0333557 A1 | 11/2017 | Ardeleanu |
| 2018/0094069 A1 | 4/2018 | Stahl |
| 2018/0094070 A1 | 4/2018 | Stahl |
| 2018/0179288 A1 | 6/2018 | Martin et al. |
| 2019/0183973 A1 | 6/2019 | Hamilton |

FOREIGN PATENT DOCUMENTS

| | | |
|---|---|---|
| EP | 1113818 | 5/2006 |
| EP | 2022507 | 2/2009 |
| EP | 1527100 | 7/2009 |
| JP | 05-246874 | 9/1993 |
| JP | 2006-131623 | 5/2006 |
| JP | 2016521713 A | 7/2016 |
| RU | 2162711 | 2/2001 |
| RU | 2453303 C1 | 6/2012 |
| WO | WO 92/19259 | 11/1992 |
| WO | WO 94/14975 | 7/1994 |
| WO | WO 2001/092340 | 12/2001 |
| WO | WO 2003/048083 | 6/2003 |
| WO | WO 2005/047331 | 5/2005 |
| WO | WO 2005/085284 | 9/2005 |
| WO | WO 2006/003407 | 1/2006 |
| WO | WO 2006/072564 | 7/2006 |
| WO | WO 2006/083390 | 8/2006 |
| WO | WO 2008/054606 | 5/2008 |
| WO | WO 2009/124954 | 10/2009 |
| WO | WO 2010/053751 | 5/2010 |
| WO | WO 2010/065557 | 6/2010 |
| WO | WO 2010/120524 | 10/2010 |
| WO | WO 2011/026966 | 3/2011 |
| WO | WO 2012/047954 | 4/2012 |
| WO | WO 2012/094643 | 7/2012 |
| WO | WO 2012/177945 | 12/2012 |
| WO | WO 2013/051928 | 4/2013 |
| WO | 2013/088109 | 6/2013 |
| WO | WO 2013/155010 | 10/2013 |
| WO | 2014/031610 | 2/2014 |
| WO | WO 2014/039461 | 3/2014 |
| WO | WO 2014/059178 | 4/2014 |
| WO | 2014/205365 | 12/2014 |
| WO | 2014197470 A1 | 12/2014 |
| WO | 2015/006571 | 1/2015 |
| WO | 2016077675 A1 | 5/2016 |
| WO | 2017/143270 | 8/2017 |
| WO | 2018/045130 | 3/2018 |

OTHER PUBLICATIONS

Ul-Haq et al, Cytokine & Growth Factor Reviews 32 (2016) 3-15.*
Mueller et al, Biochimica et Biophysica Acta, 2002, vol., pp. 237-250.*
Cortes, J. R, et al., Proton pump inhibitors inhibit IL-4 and IL-13 signaling stat6 activation, European Journal of Ummunology, (Sep. 2009) vol. 39, Supp.
Ivashkin, V. T., et al., "Eosinophilic esophagitis: literature review and description of own survey," RJGHC, 2012, vol. 22, 1, pp. 71-81.
Ivashkin, V. I., et al., "Eosinophilic esophagitis," a textbook for physicians, Moscow, "AISPI RAS" JSC, Feb. 14, 2013, pp. 13-21, 57-62 No English translation. (cited in Russian Office Action for RU Appl. No. 2016104400).
Assa'ad, Amal, "What is new in the Treatment of Eosinophilic Eosophagitis?" Clinical and Translational Allergy 2011 (Suppl 1):S69, doi:10.1186/2045-7022-1-S1-S69.
Abonia, et al., 2013, Journal of Allergy Clin Immunol, "High prevalence of eosinophilic esophagitis in patients with inherited connective tissue disorders".
Aceves, et al., 2009, Immunol Allergy Clin N Am 29 p. 197-211, "Relationships Between Eosinophilic Inflammation, Tissue Remodeling, and Fibrosis in Eosinophilic Esophagitis".
Arron et al. (2009) Am. J. Respir. Crit. Care Med. Online Abstracts Issue. 2009, B21 Airway Inflammation: New Information about Mediators and Biomarkers/Poster Discussion/Monday, May 18, 2009 "Peripheral Biomarkers of an IL-13 Induced Bronchial Epithelial Gene Signature in Asthma".
Assa'ad, et al., 2011, Gastroenterology 141:1593-1604, "An Antibody Against IL-5 Reduces Numbers of Esophageal Intraepithelial Eosinophils in Children with Eosinophilic Esophagitis".
Bachert et al. (2005) Drugs 65(11):1537-1552 "Pharmacological management of nasal polyposis".
Balint and Larrick (1993) Gene 137:109-118, "Antibody engineering by parsimonious mutagenesis".
Barnes, 2008, The Journal of Clinical Investigation 118(11):3546-3556, "The cytokine network in asthma and chronic obstructive pulmonary disease".
Bateman et al. (2004) Am. J. Respir. Crit. Care Med. 170:836-844 "Can guideline-defined asthma control be achieved?".
Beck et al. (2014) New England Journal of Medicine 371(2): 130-139 "Dupilumab treatment in adults with moderate-to-severe atopic dermatitis".
Beyer, et al., 2002, Journal of Allergy Clin Immunol 109(4):707-713, "Human milk-specific mucosal lymphocytes of the gastrointestinal tract display a $T_H2$ cytokine profile".
Bhardwaj and Ghaffari, 2012, Ann Allergy Asthma Immunol 109:155-159, "Biomarkers for eosinophilic esophagitis: a review".
Bieber, T., et al., "Atopic dermatitis: a candidate for disease-modifying strategy," Allergy 67 (2012) 969-975.
Blanchard, et al., 2005, Clin Exp Allergy 35:1096-1103, "Inhibition of human interleukin-13-induced respiratory and oesophageal inflammation by anti-human-interleukin-13 antibody (CAT-354)".
Blanchard, et al., 2006, The Journal of Clinical Investigation 116(2), "Eotaxin-3 and a uniquely conserved gene-expression profile in eosinophilic esophagitis".
Blanchard, et al., 2007, Journal of Allergy Clin Immunol 120(6), "IL-13 involvement in eosinophilic esophagitis: Transcriptome analysis and reversibility with glucocorticoids".
Blanchard and Rothenberg, 2009, Immunol Allergy Clin N Am 29, p. 141-148, "Chemotactic Factors Associated with Eosinophilic Gastrointestinal Diseases".

(56) References Cited

OTHER PUBLICATIONS

Blanchard, et al., 2010, The Journal of Immunology, "Coordinate Interaction between IL-13 and Epithelial Differentiation Cluster Genes in Eosinophilic Esophagitis".
Blanchard, et al., 2011, J Allergy Clin Immunol, 127(1):208-217, "A striking local esophageal cytokine expression profile in eosinophilic esophagitis".
Brown-Whitehorn and Spergel (2010) Expert Rev Clin Immunol. 6:1:101-115 "The link between allergies and eosinophilic esophagitis: implications for management strategies".
Burmeister-Getz et al. (2009) J. Clin. Pharmacol. 49:1025-1036 "Human pharmacokinetics/pharmacodynamics of an interleukin-4 and interleukin-13 dual antagonist in asthma".
Caldas et al. (2003) Molecular Immunology 39:941-952 "Humanization of the anti-CD18 antibody 6.7: an unexpected effect of a framework residue in binding to antigen".
Carter (2006) The Journal of Immunology 6:343-357, "Potent Antibody Therapeutics by Design".
Casset et al. (2003) Biochemical and Biophysical Research Communication 307:198-205 "A peptide mimetic of an anti-CD4 monoclonal antibody by rational design".
Chehade and Sampson, 2009, Immunol Allergy Clin N Am 29, p. 149-158, "The Role of Lymphocytes in Eosinophilic Gastrointestinal Disorders".
Cheng et al. (2012) Am J Physiol Gastrointest Liver Physiol 303:G1175-G1187 "Tissue remodeling in eosinophilic esophagitis".
Chien et al. (1989) Proc. Natl. Acad. Sci. 86:5532-5536 "Significant structural and functional change of an antigen-binding site by a distant amino acid substitution: Proposal of a structural mechanism".
Corren et al. (2010) American Journal of Respiratory and Critical Care Medicine 181(8):788-796 "A Randomized, Controlled, Phase 2 Study of AMG 317, an IL-4R Antagonist, in Patients with Asthma".
Davies, et al. (1996) Immunotechnol. 2(3): 169-179, "Affinity improvement of single antibody VH domains: residues in all three hypervariable regions affect antigen binding".
Davis (2004) Seminars in Immunology 16: 239-243, "The evolutionary and structural 'logic' of antigen receptor diversity".
De Pascalis et al. (2002) Journal of Immunology 169(6):3076-3084 "Grafting of "Abbreviated" Complementarity-Determining Regions Containing Specificity-Determining Residues Essential for Ligand Contact to Engineer a Less Immunogenic Humanized Monoclonal Antibody".
Dellon, 2013, Dig Dis Sci, "The Pathogenesis of Eosinophilic Esophagitis: Beyond the Eosinophil".
Desreumaux, et al., 1996, Gastroenterology 110:768-774, "Interleukin 3, Granulocyte-Macrophage Colony-Stimulating Factor, and Interleukin 5 in Eosinophilic Gastroenteritis".
Fillon, et al., 2009, Immunol Allergy Clin N Am 29, pp. 171-178, "Epithelial Function in Eosinophilic Gastrointestinal Diseases".
Foote and Winter (1992) J. Mol. Biol. 224:487-499 "Antibody Framework Residues Affecting the Conformation of the Hypervariable Loops".
Foroughi, et al., 2007, J Allergy Clin Immunol 120(3):594-601, "Anti-IgE Treatment of Eosinophil Associated Gastrointestinal Disorders".
Franciosi and Liacouras, 2009, Immunol Allergy Clin N Am 29, pp. 19-27, "Eosinophilic Esophagitis".
Gavett, et al. (1997) The American Physiological Society L253-L261, "Interleukin-4 receptor blockade prevents airway responses induced by antigen challenge in mice".
Gevaert et al. (2006) Journal of Allergy and Clinical Immunology 118(5):1133-1141 "Nasal IL-5 levels determine the response to anti-IL-5 treatment in patients with nasal polyps".
Giusti et al. (1987) Proc. Natl. Acad. Sci. 84:2926-2930 "Somatic diversification of S107 from an antiphosphocholine to anti-DNA autoantibody is due to a single base change in its heavy chain variable region".
Groves, et al. (2007) Aeroderm in AD Poster at St. John's Institute of Dermatology, "Inhibition of IL-4 and IL-13 with an IL-4 mutein (Aeroderm) protects against flares in atopic eczema".
Grunewald et al. (1998) The Journal of Immunology 160(8):4004-4009 "An Antagonistic IL-4 Mutant Prevents Type I Allergy in the Mouse: Inhibition of the IL-4/IL-13 Receptor System completely Abrogates Humoral Immune Response to Allergen and Development of Allergic Symptoms in Vivo".
Gussow and Seemann (1991) Methods in Enzymology 203:99-121 "Humanization of Monoclonal Antibodies".
Hijnen, et al. (2004) J. Allergy Clin. Immunology 113(2): 334-340, "Serum thymus and activation-regulated chemokine (TARC) and cutaneous T Cell-attracting chemokine (CTACK) levels in allergic diseases: TARC and CTACK are disease-specific markers for atopic dermatitis".
Holm et al. (2007) Molecular Immunology 44:1075-1084 "Functional mapping and single chain construction of the anti-cytokeratin 8 monoclonal antibody TS1".
Holt, et al. (2003) Trends Biotechnol. 21 (11): 484-490, "Domain antibodies: proteins for therapy".
Hopkins et al. (2007) Otolaryngology-Head and Neck Surgery 137(4):555-561 "The Lund-Mackay staging system for chronic rhino sinusitis: How is it used and what does it predict?".
Hopkins (2009) Clinical Otolaryngology 34(5):447-454 "Psychometric validity of the 22-item Sinonasal Outcome Test".
Jahnz-Rozyk, et al. (2005) Allergy 60: 685-688, "Serum thymus and activation-regulated chemokine, macrophage-derived chemokine and eotaxin as marker of severity of atopic dermatitis".
Junttila, et al. (2008) J. Exp. Med. 205(11): 2595-2608, "Tuning sensitivity to IL-4 and IL-13: differential expression of IL-4Rα, IL-13Rα1, and γc regulates relative cytokine sensitivity".
Jyonouchi, et al., 2013, Basic Mechanisms in Allergic Disease, "Invariant Natural Killer T cells in children with Eosinophilic Esophagitis".
Kagami, et al. (2003) Clin. Exp. Immunology 134: 309-313, "Significant elevation of serum levels of eotaxin-3/CCL26, but not of eotaxin-2/CCL24, in patients with atopic dermatitis: serum eotaxin-3/CCL26 levels reflect the disease activity of atopic dermatitis".
Kakinuma, et al. (2002) Clin. Exp. Immunol 127:270-273, "Serum macrophage-derived chemokine (MDC) levels are closely related with the disease activity of atopic dermatitis".
Kakinuma, et al. (2001) J. Allergy Clin. Immunol. 107(3):535-541, "Thymus and activation-regulated chemokine in atopic dermatitis: Serum thymus and activation-regulated chemokine level is closely related with disease activity".
Kakkar, et al. (2011) Pharmaceutical Research, Kluwer Academic Publishers-Plenum Publishers 28(10): 2530-2542, "Population PK and IgE Pharmacodynamic Analysis of a Fully Human Monoclonal Antibody Against IL4 Receptor".
Katial, 2009, Immunol Allergy Clin N Am 29, pp. 119-127, "Biomarkers for Nononcologic Gastrointestinal Disease".
Kelly and Liu (2014) World Allergy Organization Journal 7(S1):p. 8 "Poster 1013: IL-4R alpha antibody inhibits IgE production and airway remodeling in mouse model of house dust mite-induced eosinophilic asthma".
Kim, et al., 2004, J Allergy Clin Immunol 114(6):1449-1455, "Rebound eosinophilia after treatment of hypereosinophilic syndrome and eosinophilic gastroenteritis with monoclonal anti-IL-5 antibody SCH55700".
Konikoff, et al., 2006, Gastroenterology 131:1381-1391, "A Randomized, Double-Blind, Placebo-Controlled Trial of Fluticasone Propionate for Pediatric Eosinophilic Esophagitis".
Kottyan, et al., 2014, Nature Genetics, "Genome-wide association analysis of eosinophilic esophagitis provides insight into the tissue specificity of this allergic disease".
Kopf, et al. (1993) Letters to Nature 362: 245-248, "Disruption of the murine IL-4 gene blocks Th2 cytokine responses".
Kostic et al., (2010) Clinical Immunology 135:S105-S106, "A Fully Human IL4Rα Antibody for Inhibition of IL-4/IL-13-driven TH2 Responses in Allergic Disease".
Kulis et al. (2011) J. Allergy Clin Immunol 127:81-88 "Single-tree nut immunotherapy attenuates allergic reactions in mice with hypersensitivity to multiple tree nuts".

(56) References Cited

OTHER PUBLICATIONS

Leung et al. (2003) The New England Journal of Medicine 348:986-993 "Effect of Anti-IgE Therapy in Patients with Peanut Allergy".
Leung, et al. (2004) The Journal of Clinical Investigation 113(5): 651-657, "New insights into atopic dermatitis".
Lezcano-Meza et al. (2003) Allergy 58(10):1011-1017 "Interleukin (IL)-4 and to a lesser extent either IL-13 or interferon-gamma regulate the production of eotaxin-2/CCL24 in nasal polyps".
Liacouras, et al., 2011, J Allergy Clin Immunol 128(1), "Eosinophilic esophagitis: Updated consensus recommendations for children and adults".
Lin et al (2007) Clinical Reviews in Allergy & Immunology 33(3):167-177 "Role of Bacterial Pathogens in Atopic Dermatitis".
Liu, et al, 1999, Gene Therapy, 6:1258-1266, "Hydrodynamics-based transfection in animals by systemic administration of plasmid DNA".
Lucendo and Sanchez-Cazalilla, 2012, Expert Rev. Clin. Immunol. 8(8):733-745, "Adult versus pediatric eosinophilic esophagitis: important differences and similarities for the clinician to understand".
Ludmila and Xia (2014) World Allergy Organization Journal 7(1):p. 8 "Poster 1013: IL-4R alpha antibody inhibits IgE production and airway remodeling in mouse model of house dust mite-induced eosinophilic asthma".
Lwin, et al., 2011, Modern Pathology 24:556-563, "Eosinophilic gastritis: histopathological characterization and quantification of the normal gastric eosinophil content".
MacCallum et al. (1996) J. Mol. Biol. 262:732-745 "Antibody-antigen Interactions: Contact Analysis and Binding Site Topography".
Maliszewski, et al. (1994) Proc. Soc. Exp. Bio. Med. 206(3): 233-237, "In vivo biological effects of recombinant soluble interleukin-4 receptor".
Mannon et al., (2012) Gut 61(12):1765-1773, "Interleukin 13 and its role in gut defense and inflammation".
Mariuzza et al. (1987) Ann. Rev. Biophys. Biophys. Che. 16:139-159 "The Structural Basis of Antigen-Antibody Recognition".
Masterson, et al., 2011, Curr Opin Gastroenterol. 27(6): 515-522, "Update on clinical and immunological features of eosinophilic gastrointestinal diseases".
Mishra, et al., 2001, J Clin. Invest. 107:83-90, "An etiological role for aeroallergens and eosinophils in experimental esophagitis".
Mishra, et al., 2002, The Journal of Immunology 168:2464-2469, "IL-5 Promotes Eosinophil Trafficking to the Esophagus".
Mishra and Rothenberg, 2003, Gastroenterology 125:1419-1427, "Intratracheal IL-13 Induces Eosinophilic Esophagitis by an IL-5, Eotaxin-1, and STAT6-Dependent Mechanism".
Moldoveanu et al. (2009) Journal of Inflammation Research 2:1-11 "Inflammatory mechanisms in the lung".
Molfino et al. (2012) Clinical & Experimental Allergy 42(5):712-737 "Molecular and clinical rationale for therapeutic targeting of interleukin-5 and its receptor".
Morioka et al. (2009) British Journal of Dermatology 160(6):1172-1179 "IL-4/IL-13 antagonist DNA vaccination successfully suppresses Th2 type chronic dermatitis".
Muller et al. (1993) Journal of Immunology 150:5576-5584 "Th2 cells mediate IL-4-dependent local tissue inflammation".
Nadeau et al. (2011) J. Allergy Clin. Immunol 127(6) Letters to the Editor "Rapid oral desensitization in combination with omalizumab therapy in patients with cow's milk allergy".
Nguyen et al., (2011) Immunological Reviews 242(1):258-271, "Immune modulation for treatment of allergic disease".
Niederberger (2009) Immunology Letters 122:131-133 "Allergen-specific immunotherapy".
Niranjan, et al., 2013, Immunology and Cell Biology, pp. 1-8, "Pathogenesis of allergen-induced eosinophilic esophagitis is independent of interleukin (IL)-13".
Noel, et al., 2004, The New England Journal of Medicine 351:940-941, "Eosinophilic Esophagitis".
Novartis, 2013, QAX576 "A double blinded, randomized, placebo-controlled trial of intravenous QAX576 in the treatment of eosinophilic esophagitis".
Oh, et al., 2010, Eur Respir Rev 19(115):46-54, "Investigational therapeutics targeting the IL-4/IL-13/STAT-6 pathway for the treatment of asthma".
Ohno, et al. (1985) Proc. Natl. Acad. Sci. USA 82: 2945-2949, "Antigen-binding specificities of antibodies are primarily determined by seven residues of $V_h$".
Ong (2012) Expert Opinion on Emerging Drugs 17:2:129-133, "Editorial update on emerging treatments of atopic dermatitis".
Otani et al., (2013) Journal of Allergy and Clinical Immunology 131(6):1576-1582, "Anti-IL-5 therapy reduces mast cell and IL-9 cell numbers in pediatric patients with eosinophilic esophagitis".
Otulana et al. (2011) Am. J. Respir. Crit. Care Med. 183:A6179 "A Phase 2b Study of Inhaled Pitrakinra, An IL-4R/IL-13 Antagonist, Successfully Identified Responder Subpopulations of Patients with Uncontrolled Asthma".
Oyoshi et al. (2009) Advances in Immunology 102:135-226 "Cellular and Molecular Mechanisms in Atopic Dermatitis".
Peserico, et al. (2008) British Journal of Dermatology 158: 801-807, "Reduction of relapses of atopic dermatitis with methylprednisolone aceptonate cream twice weekly in addition to maintenance treatment with enrollient: a multicentre, randomized, double-blind, controlled study".
Petry et al. (2012) Anais Brasileiro De Dermatologia 87(5):732-733 "Bacterial skin colonization and infections in patients with atopic dermatitis".
Prieto and Richter, 2013, Curr Gastroenterol Rep 15:324, "Eosinophilic Esophagitis in Adults: an Update on Medical Management".
Prussin, et al., 2009, J Allergy Clin Immunol. 124(6):1326-1332, "Eosinophilic gastrointestinal disease and peanut allergy are alternatively associated with IL-5+ and IL-5-TH2 responses".
Rafi et al. (2010) Allergy and Asthma Proceedings 31(1):76-83 "Effects of omalizumab in patients with food allergy".
Rayapudi, et al., 2010, Journal of Leukocyte Biology 88, "Indoor insect allergens are potent inducers of experimental eosinophilic esophagitis in mice".
Receptos, Inc. 2013 Annual Report.
Ring et al. (2012) J. Eur. Acad. Dermatol. Venereol. 26(8):1045-1060 "Guidelines for treatment of atopic eczema (atopic dermatitis) Part 1".
Roll et al. (2006) J. Investig Allergol Clin Immunol 16(2):79-85 "Safety of specific immunotherapy using a four-hour ultra-rush induction scheme in bee and wasp allergy".
Rothenberg, 2004, J Allergy Clin Immunol, "Eosinophilic gastrointestinal disorders (EGID)".
Rothenberg, 2009, Gastroenterology 137:1238-1249, "Biology and Treatment of Eosinophilic Esophagitis".
Roitt, et al. (2001) Mosby—Harcourt Publishers Limited, "Immunology—Sixth Edition" pp. 110-111.
Rudikoff et al. (1982) Proc. Natl. Acad. Sci. 79:1979-1983 "Single amino acid substitution altering antigen-binding specificity".
Sampson et al. (2011) J. Allergy Clin Immunol. 127(5) Letters to the Editor, "A phase II, randomized, double-blind, parallel-group, placebo0controlled oral food challenge trial of Xolair (omalizumab) in peanut allergy".
"Sanofi and Regeneron Report Positive Proof-of-Concept Data for Dupilumab, an IL-4R alpha Antibody, in Atopic Dermatitis" 71st Annual Meeting of the American Academy of Dermatology (2013) http://files.shareholder.com/downloads/REGN/2689212012x0x640531/794a7e54-6904-416b-a38-a4ccc1726852/REGN_News_2013_3_2_General_Releases.pdf.
Sanofi with Regeneron Pharmaceuticals "An Evaluation of Dupilumab in Patients with Nasal Polyposis and Chronic Symptoms of Sinusitis" Trial in Progress, Jun. 2014. ClinicalTrials.gov Identifier: NCT01920893. Retrieved from the Internet URL: http://clinicaltrials.gov/show/NCT01920893 Accessed on Sep. 29, 2014.
Sato, et al. (1993) J. Immunol. 150(7): 2717-2723, "Recombinant soluble murine IL-4 receptor can inhibit or enhance IgE responses in vivo".

(56) References Cited

OTHER PUBLICATIONS

Scavuzzo et al. (2005) Biomedicine & Pharmacotherapy 59(6):323-9 "Inflammatory mediators and eosinophilia in atopic and non-atopic patients with nasal polyposis".
Schmitt, et al. (2007) J. of Allergy and Clinical Immunology 120(6): 1389-1398, "What are the best outcome measurements for atopic eczema? A systematic review".
Schmidt-Weber (2012) Chem Immunol Allergy 96:120-125 "Anti-IL-4 as a New Strategy in Allergy".
Schneider et al. (2013) J. Allergy Clin Immunol 132(6):1368-1374 "A pilot study of omalizumab to facilitate rapid oral desensitization in high-risk peanut-allergic patients".
Sekiya et al. (2002) Allergy 57:173-177 "Increased levels of a TH2-type CC chemokine thymus and activation-regulated chemokine (TARC) in serum and induced sputum of asthmatics".
Slager et al. (2012) Journal of Allergy, Asthma and Immunology 130(2):516-522.e4 "IL-4 Receptor Polymorphisms Predict Reduction in Asthma Exacerbations During Response to an Anti IL-4 Receptor Antagonist".
Stein, et al., 2006, J Allergy Clin Immunol 118(6):1312-1319, "Anti-IL-5 (mepolizumab) therapy for eosinophilic esophagitis".
Steinke and Borish (2001) Respiratory Research 2(2):1-5 "Th2 cytokines and asthma Interleukin-4: its role in the pathogenesis of asthma, and targeting it for asthma treatment with interleukin-4 receptor antagonists".
Strauman, 2009, Immunol Allergy Clin N Am 29, pp. 11-18, "Clinical Evaluation of the Adult who has Eosinophilic Esophagitis".
Straumann, et al., 2001, J Allergy Clin Immunol 108(6):954-961, "Idiopathic eosinophilic esophagitis is associated with a $T_H2$-type allergic inflammatory response".
Straumann, 2005, J Allergy Clin Immunol 115(2):418-419, "Eosinophilic esophagitis: Escalating epidemiology?".
Straumann, et al., 2009 Gut, "Anti-interleukin-5 antibody treatment (mepolizumab) in active eosinophilic oesophagitis: a randomized, placebo-controlled, double-blind trial".
Stone et al., (2008) Clinical & Experimental Allergy 38(12):1858-1865, "Immunomodulatory therapy of eosinophil-associated gastrointestinal diseases".
Spirin (1986) Vysshaya shkola, Moscow, pp. 17-23, "Molecular Biology Ribosome structure and protein biosynthesis".
Tazawa, et al. (2004) Arch Dermatol Res 295:459-464, "Relative importance of IL-4 and IL-13 in lesional skin of atopic dermatitis".
Tepper et al. (1990) Cell 52:457-467 "IL-4 Induces Allergic-like Inflammatory Disease and Alters T Cell Development in Transgenic Mice".
Tomkinson et al. (2001) J. Immunol 166: 5792-5800, "A Murine IL-4 Receptor Antagonist that Inhibits IL-4- and IL-13-induced Responses Prevents Antigen-Induced Airway Eosinophilia and Airway Hyper responsiveness".
Vajdos et al. (2002) Journal of Molecular Biology 320(2):415-428 "Comprehensive functional maps of the antigen-binding site of an anti-ErbB2 antibody obtained with shotgun scanning mutagenesis".
Veerappan, et al., 2009, Clinical Gastroenterology and Hepatology 7:420-426, "Prevalence of Eosinophilic Esophagitis in an Adult Population Undergoing Upper Endoscopy: A Prospective Study".
Vestergaard, et al. (2000) The Journal of Investigative Dermatology 115(4): 640-646, "A $Th_2$ Chemokine, TARC, Produced by Keratinocytes May Recruit $CLA^+CCR4^+$ Lymphocytes into Lesional Atopic Dermatitis Skin".
Virchow et al. (1994) Lung 172:313-334 "Cellular and immunological markers of allergic and intrinsic bronchial asthma".
Walker, et al. (1993) Clinical and Experimental Allergy 23:145-153, "Atopic dermatitis: correlation of peripheral blood T cell activation, eosinophilia and serum factors with clinical severity".
Wark, et al. (2006) Advanced Drug Delivery Reviews 58:657-670, "Latest technologies for the enhancement of antibody affinity".
Wang and Liu, 2008, Current Opinion in Immunology 20:697-702, "The IL-17 cytokine family and their role in allergic inflammation".
Watson et al. (2011) Allergy, Asthma & Clinical Immunology 7:S4 "Atopic dermatitis".
Weinbrand-Goichberg, et al., 2013, Immunol Res, "Eosinophilic esophagitis: an immune-mediated esophageal disease".
Wenzel et al. (2007) Lancet 370:1422-1431 "Effect of an interleukin-4 variant on late phase asthmatic response to allergen challenge in asthmatic patients: results of two phase 2a studies".
Wenzel et al. (2010) European Respiratory Society, Annual Congress "ERS—Programme" pp. 3980.
Wenzel et al. (2013) New England Journal of Medicine 368(26):2455-2466 "Dupilumab in Persistent Asthma with Elevated Eosinophil Levels".
Wershil, 2009, Immunol Allergy Clin N Am 29, pp. 189-195. "Exploring the Role of Mast Cells in Eosinophilic Esophagitis".
Whalley et al. (2004) British Journal of Dermatology 150:274-283 "A new instrument for assessing quality of life in atopic dermatitis: international development of the Quality of Life Index for Atopic Dermatitis (QoLIAD)".
Wilhelm and Stockinger, 2011, Frontiers in Immunology 2(68), "Innate lymphoid cells and type 2 (Th2) mediated immune responses-pathogenic or beneficial?".
Wills-Karp and Finkelman, 2008, Science Signaling 1(51), "Untangling the Complex Web of IL-4 and IL-13 Mediated Signaling Pathways".
Weihrauch, et al. (2005) Cancer Research 65:5516-5519, "Elevated Serum Levels of CC Thymus and Activation-Related Chemokine (TARC) in Primary Hodgkin's Disease: Potential for a Prognostic Factor".
Winkler et al. (2000) J. Immunol. 165(8):4505-4514 "Changing the Antigen Binding Specificity by Single Point Mutations of an Anti-p24 (HIV-1) Antibody".
Winter and Harris (1993) Immunology Today 14(6):243-246 "Humanized Antibodies".
Wu et al. (1999) Journal of Molecular Biology 294:151-162 "Humanization of a murine monoclonal anti body by simultaneous optimization of framework and CDR residues".
Yamanaka et al. (2011) Curr Probl Dermatol 41:80-92 "The Role of Cytokines/Chemokines in the Pathogenesis of Atopic Dermatitis".
Yan and Shaffer (2006) World J Gastroenterol 12(15):2328-2334 "Eosinophilic esophagitis: A newly established cause of dysphagia".
Zurawski, et al. (1995) J. Bioi. Chem. Am. Society of Biolochemical Biologists. 270(23):13869-13878, "The primary binding subunit of the human Interleukin-4 receptor is also a component of the Interleukin-13 receptor".
Zuo, et al., 2010, Journal of Immunology 185:660-669, "IL-13 Induces Esophageal Remodeling and Gene Expression by an Eosinophil-Independent, IL-13R{alpha}2-Inhibited Pathway".
Martel, Britta C., et al., "Translational animal Models of Atopic Dermatitis for Preclinical Studies," Yale Journal of Biology and Medicine 90 (2017), pp. 389-402.
Silverberg J.I., et al., "Dupilumab treatment induces rapid clinical improvement of itch in patients with moderate-to-severe atopic dermatitis" Paper presented at: American Academy of Dermatology—76th Annual Meeting; Feb. 16-20, 2018; San Diego, CA, USA.
Silverberg J.I., et al., p. 481, "Dupilumab treatment rapidly improves itch in patients with moderate-to-severe atopic dermatitis" An Allergy Asthma Immunol. 2017;119(suppl 5):S95.
Hamilton, Jennifer D., et al., "Drug evaluation review: Dupilumab in atopic dermatitis," Immunotherapy (2015) 7(10), 1043-1058.
Blauvelt, Andrew, et al., "Long-term management of moderate-to-severe atopic dermatitis with dupilumab and concomitant topical corticosteroids (Liberty AD CHRONOS): a 1-year, randomised, double-blinded, placebo-controlled, phase 3 trial," www.thelancet.com, published online May 4, 2016, http://dx.doi.org/10.1016/S0140-6736(17)31191-1.
Simpson, E.L., et al., "Two Phase 3 Trials of Dupilumab versus Placebo in Atopic Dermatitis," The New England Journal of Medicine, Oct. 1, 2016, DOI: 10.1056/NEJMoa1610020.
Oetjen, Landon K., et al., "Sensory Neurons Co-opt Classical Immune Signaling Pathways to Mediate Chronic Itch," Sep. 21, 2017, Cell 171, 217-228.
Sanofi/Regeneron Press Release, "Sanofi and Regeneron Report Positive Results with Sarilumab in First Phase 3 Rheumatoid Arthritis Registration Trial", Paris, France and Tarrytown, NY, Nov. 22, 2013, 3 pages.

(56) References Cited

OTHER PUBLICATIONS

Almagro et al., "Humanization of antibodies", (2008) Frontiers in Bioscience 13:1619-1633.
Romaniuk, L.I., "Allergan-specific immunotherapy: mechanisms, methods and efficacy", Clinical Immunology, Allergology and Infectology, 2012, special issue, pp. 44-47. (with English translation of the cited portion).
Bagnasco, Diego et al., "A critical evaluation of Anti-IL-13 and Anti-IL-4 Strategies in Severe Asthma", Int. Arch Allergy Immunol 2016; 170: 122-131.
Durham, Andrew L. et al., "Targeted anti-inflammatory therapeutics in asthma and chronic obstructive lung disease", Airway Disease Section, Nat'l. Heart and Lung Institiute, Imperial Collge London, UK, published Aug. 12, 2015, 12 pages.
Russian Official Action from Russian Federation for RU Application 2016104400, dated Oct. 6, 2017, with translation, 4 pages.
Saeki, Hidehisa, "Guidelines for Management of Atopic Dermatis", (Advances in Medicine, Special Issue, 2009, vol. 228(1):75-79 in part), cited in the Japanese Patent Application No. 2015-531149.
Simpson, Eric L. et al., "Dupilumab therapy provides clinically meaningful improvement in patient-reported outcomes (PROs): A phase IIb, randomized, placebo-controlled, clinical trial in adult patients with moderate to severe atopic dermatitis (AD)", Journal of the American Academy of Dermatology, Mosby, Inc., US, vol. 75, No. 3, Jun. 4, 2016.
Simpson, Eric L. et al., "Patient burden of moderate to severe atopic dermatitis (AD): Insights from a phase 2b clinical trial of dupilumab in adults," Journal of the American Academy of Dermatology, Mosby, Inc., US, vol. 74, No. 3, Jan. 14, 2016.
Thaci, Diamant et al.: "Efficacy and Safety of Dupilumab in Adults with Moderate-to_Severe Atopic Dermatitis Inadequately Controlled by Topical Treatments: A Randomised, placebo-controlled, dose-ranging phase 2b trial," The Lancet, The Lancet Publishing Group, GB, vol. 387, No. 10013, Oct. 8, 2015.
Tsianakas, Athanasios et al., "Dupilumab: A Milestone in the Treatment of Atopic Dermatitis," The Lancet, The Lancet Publishing Group, GB vol. 387, No. 10013, Oct. 8, 2015.
Bieber, T., et al., "Atopic dermatitis: A candidate for disease-modifying strategy," Allergy 67 (Apr. 12, 2012) 969-975.
Sanofi, "Positive Phase 2a Results of Dupilumab in Asthma in the New England Journal of Medicine," May 21, 2013, Regeneron Pharmaceuticals, Inc.
Wang, et al., "Peanut-induced intestinal allergy is mediated through a mast cell-IgE-FceRI-IL-13 Pathway," Journal of Allergy and Clinical Immunology, 2010, vol. 126, No. 2, 306-316, e1-e12.
Nadeau, et al., "Oral Immunotherapy and Anti-IgE Antibody-Adjunctive Treatment for Food Allergy," Immunology and Allergy clinics of North America, 2012, vol. 32, No. 1, 111-133.
Mathias, et al., IgE-mediated systemic anaphylaxs and impaired tolerance to food antigens in mice with enhanced IL-4 receptor signaling, Journal of Allergy and Clinical Immunology, 2011, vol. 127, No. 3, 795-805, e1-e6.
Burton, et al., "Direct effects of IL-4 on mast cells drive their intestinal expansion and increase susceptibility to anaphylaxis in a murine model of food allergy," Mucosal Immunology, Nov. 14, 2012, doi:10.1038/mi.2012.112.
Akiyama, et al., A Study on Indoor Allergens Measured in Home Environments of Adult-Asthmatic Patients, Study No. 9620, 1-10.
Terui, et al., "Learning from Fungus Allergy in Atopic Dermatitis Patients," Japan J. Med. Mycol, 2000, vol. 41, No. 3, 157-160.
Wong, et al., "Guidelines for the management of atopic dermatitis (eczema) for pharmacists," CPJ/RPC, Sep./Oct. 2017, vol. 150, No. 5.
Highlights of Prescribing Information, DUPIXENT (dupilumab) injection, for subcutaneous use Initial U.S. Approval: 2017, U.S. Food and Drug Administration (FDA), Revised Mar. 2017.
Hong, Judith, et al., "Management of Itch in Atopic Dermatitis," Seminars in cutaneous Medicine and Surgery, vol. 30, No. 2, May 14, 2011, pp. 71-86 XP028240445.
Paton, D. M., "Dupilumab: human monoclonal antibody against IL-4Ralpha for moderate to severe atopic dermatitis," Drugs Today, vol. 53, No. 9, Sep. 1, 2017, pp. 477-487, XP055465888.
Dellon, Evan S. et al., "A Randomized, Double-Blind, Placebo-Controlled Trial of a Novel Recombinant, Humanized, Anti-Interleukin-13 Monoclonal Antibody (RPC4046) in Patients with Active Eosinophilic Esophagitis: Results of the HEROS Study", Oct. 14, 2016, retrieved from the Internet on Sep. 20, 2018 at: https://www.eventscribe.com/2016/ACG/QRcode.asp?Pres= 178380, 3 pages.
Rothenberg, Marc E. et al., "Intravenous anti-IL-13 mAb QAX576 for the Treatment of eosinophilic esophagitis", Journal of Allergy and Clinical Immunology, vol. 135, No. 2, Feb. 1, 2015, pp. 500-507.
Hirano, Ikuo et al., "Dupilumab Efficacy and Safety in Adult Patients With Active Eosinophilic Esophagitis: a Randomized Double-Blind Placebo-Controlled Phase 2 Trial", Oct. 13, 2017, retrieved from the internet on Sep. 20, 2018 at: http://files.shareholder.com/downloads/REGN/6138593856x0x959724/16AF93AE-DAF8-480A-8301-311C91E8FA41/Presentation.pdf, 20 pages.
Hirano, Ikuo et al., "Sa1113—Correlation Between Esophageal Distensibility and Objective Measures of Disease in Patients with Active Eosinophilic Esophagitis: A Post HOC Analysis of a Randomized, Placebo-Controlled, Phase 2 Dupilumab Trial", abstract, Gastroenterology, vol. 154, No. 6, May 1, 2018, 1 page.
Collins, Margaret H. et al., "Sa1151—Baseline Characteristics and Correlation Between Dysphagia and Disease Activity in Patients with Eosinophilic Esophagitis in a Randomized, Placebo-Controlled, Phase 2 Dupilumab Trial", abstract, Gastroenterology, vol. 154, No. 6, May 1, 2016, 1 page.
Pesek, Robert D. et al., "Emerging drugs for eosinophilic esophagitis", Expert Opinion on Emerging Drugs, vol. 23, No. 2, Apr. 3, 2018, 12 pages.
Akiyama, et al., A Study on Indoor Allergens Measured in Home Environments of Adult-Asthmatic Patients, Housing Research Foundation, Research Annual Report, 1997, No. 24, Study No. 9620, 1-10.
European Notice of Opposition in Application 13765844.9, dated Feb. 22, 2019, 34 pages.
Nguyen, Tran Hoai et al., "FutureForms of Immunotherapy and Immunomodulators in Allergic Disease", Immunol Allergy Clin N Am 31 (2011); 343-365.
Antoniu, Sabina, "Pitrakinra, a Dual IL-4R/IL-13 Antagonist for the Potential Treatment of Asthma and Eczema", Current Opinion in Investigational Drugs Nov. 2010 (11): 1286-1294.
International Investigative Dermatology, Edinburgh, Conference Posters, May 8-11, 2013, 4 pages.
Abstracts, "Human Clinical Research and Therapeutics", Journal of Investigative Dermatology vol. 133, Supplement 1, (2013), pp. S159-S190, Abstracts 1042, and 1048 to 1050, http://apps.webofknowledge.com/full_record.do?product=WOS&search_mode=GeneralSearch&qid=2&SID=E6MDFsiCnXC9MIROx21&page=1&doc=1, 32 pages.
Bankhead, Charles, "IL-4 Antibody Tames Atopic Dermatitis", Medpage Today Article, https://www.medpagetoday.com/meetingcoverage/aad/37636, Mar. 3, 2013, 3 pages.
Clinical Trials, Study NCT01548404—"Study of REGN668 in Adult Patients With Extrinsic Moderate-to-Severe Atopic Dermatitis", first publication of clinical study protocol, Mar. 7, 2012, 7 pages.
Clinical Trials, Study NCT01548404—"Study of Dupilumab in Adult Patients with Extrinsic Moderate-to-severe Atopic Dermatitis", final publication of clinical study protocol, Aug. 27, 2015, 8 pages.
Clinical Trials, Study NCT00676884—"A Phase Study to Investigate the Effects of Repeated Administration of AeroDerm in Subjects with Atopic Dermatitis", Aeroderm first publication of clinical study protcol in TCS resistant moderate-to-severe AD, May 13, 2008, 6 pages.
Garriga, A., "71st Annual Meeting of the American Academy of Dermatology (AAAD) . . . Miami Beach, FL, Mar. 1-5, 2013", Drugs of the Future 2013, 38(4): 275-279, Apr. 2013, https://journals.

(56) References Cited

OTHER PUBLICATIONS prous.com/journals/servlet/xmlxls/pk_journals.xml_toc_pr?p_JournalID=2&p_IssueID=1186, 5 pages.

British Society for Allergy and Clinical Immunology (BSACI) Abstracts of the 2013 Annual Meeting (dated Jul. 8-10, 2013), Clinical & Experimental Allergy, 43, 1428-1472, Nov. 22, 2013, https://onlinelibrary.wiley.com/toc/13652222/2013/43/12, 45 pages.

Clinical Trials, Study NCT01639040—"Study to Assess the Safety of REGN668 (SAR231893) Administered Concomitantly with Topical Corticosteroids (TCS) in Patients with Moderate-to-severe Atopic Dermatitis (AD)", Concomitant treatment with TCS, Jul. 11, 2012, 6 pages.

Journal of Allergy & Clinical Immunology: Abstracts at conference; https://www.jacionline.org/issue/S0091-6749(13)X0013-2, Feb. 2013, 1 page.

Joost, T.H. Van, "Cyclosporin in atopical dermatitis: a multicentre placebo-controlled study", Journal of the America Academy of Dermatology, (1992), vol. 27, Issue 6, Part 1, pp. 922-928.

BSACI News Report confirming BSACI conference date of Jul. 8-10, 2013, 2 pages.

Clinical Trials Study No. NCT01312961—"Efficacy, Safety, and Tolerability of Dupilumab in Patients with Persistent Moderate to Severe Eosinophilic Asthma", In: ClinicalTrials.gov, A service of the U.S. National Institutes of Health, First Received: Mar. 11, 2011, 10 pages, Available from: https://clinicaltrials.gov/ct2/show/NCT01312961.

Kopp, M.V. et al., "Combination of omalizumab and specific immunotherapy is superior to immunotherapy in patients with seasonal allergic rhinoconjunctivitis and co-morbid seasonal allergic asthma", Clinical and Experimental Allergy, vol. 39, No. 2, pp. 271-279, published on Jan. 22, 2009.

Regeneron 2011 Annual Report (Apr. 2011), 12 pages.

ClinicalTrials.gov archive, History of Changes for Study: NCT01548404, "Study of Dupilumab in Adult Patients with Extrinsic Moderate-to-Severe Atopic Dermatitis", (Apr. 19, 2012), 7 pages.

ClinicalTrials.gov archive, History of Changes for Study: NCT01259323, "Sequential Ascending Dose Study to Assess the Safety and Tolerability of REGN668 (SAR231893) in Patients With Atopic Dermatitis", (May 31, 2012), 6 pages.

* cited by examiner

SEQUENCE LISTING

<160> NUMBER OF SEQ ID NOS: 11

<210> SEQ ID NO 1
<211> LENGTH: 124

```
<212> TYPE: PRT
<213> ORGANISM: Artificial Sequence
<220> FEATURE:
<223> OTHER INFORMATION: HCVR

<400> SEQUENCE: 1

Glu Val Gln Leu Val Glu Ser Gly Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
                100                 105                 110

Asp Val Trp Gly Gln Gly Thr Thr Val Thr Val Ser
            115                 120

<210> SEQ ID NO 2
<211> LENGTH: 112
<212> TYPE: PRT
<213> ORGANISM: Artificial Sequence
<220> FEATURE:
<223> OTHER INFORMATION: LCVR

<400> SEQUENCE: 2

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
                100                 105                 110

<210> SEQ ID NO 3
<211> LENGTH: 8
<212> TYPE: PRT
<213> ORGANISM: Artificial Sequence
<220> FEATURE:
<223> OTHER INFORMATION: HCDR1

<400> SEQUENCE: 3

Gly Phe Thr Phe Arg Asp Tyr Ala
1               5

<210> SEQ ID NO 4
<211> LENGTH: 8
<212> TYPE: PRT
```

```
<213> ORGANISM: Artificial Sequence
<220> FEATURE:
<223> OTHER INFORMATION: HCDR2

<400> SEQUENCE: 4

Ile Ser Gly Ser Gly Gly Asn Thr
1               5

<210> SEQ ID NO 5
<211> LENGTH: 18
<212> TYPE: PRT
<213> ORGANISM: Artificial Sequence
<220> FEATURE:
<223> OTHER INFORMATION: HCDR3

<400> SEQUENCE: 5

Ala Lys Asp Arg Leu Ser Ile Thr Ile Arg Pro Arg Tyr Tyr Gly Leu
1               5                   10                  15

Asp Val

<210> SEQ ID NO 6
<211> LENGTH: 11
<212> TYPE: PRT
<213> ORGANISM: Artificial Sequence
<220> FEATURE:
<223> OTHER INFORMATION: LCDR1

<400> SEQUENCE: 6

Gln Ser Leu Leu Tyr Ser Ile Gly Tyr Asn Tyr
1               5                   10

<210> SEQ ID NO 7
<211> LENGTH: 3
<212> TYPE: PRT
<213> ORGANISM: Artificial Sequence
<220> FEATURE:
<223> OTHER INFORMATION: LCDR2

<400> SEQUENCE: 7

Leu Gly Ser
1

<210> SEQ ID NO 8
<211> LENGTH: 9
<212> TYPE: PRT
<213> ORGANISM: Artificial Sequence
<220> FEATURE:
<223> OTHER INFORMATION: LCDR3

<400> SEQUENCE: 8

Met Gln Ala Leu Gln Thr Pro Tyr Thr
1               5

<210> SEQ ID NO 9
<211> LENGTH: 451
<212> TYPE: PRT
<213> ORGANISM: Artificial Sequence
<220> FEATURE:
<223> OTHER INFORMATION: HC

<400> SEQUENCE: 9

Glu Val Gln Leu Val Glu Ser Gly Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30
```

-continued

Ala Met Thr Trp Val Arg Gln Ala Pro Gly Lys Gly Leu Glu Trp Val
        35                  40                  45
Ser Ser Ile Ser Gly Ser Gly Gly Asn Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Asp Arg Leu Ser Ile Thr Ile Arg Pro Arg Tyr Tyr Gly Leu
            100                 105                 110
Asp Val Trp Gly Gln Gly Thr Thr Val Thr Val Ser Ser Ala Ser Thr
        115                 120                 125
Lys Gly Pro Ser Val Phe Pro Leu Ala Pro Cys Ser Arg Ser Thr Ser
130                 135                 140
Glu Ser Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
Val Val Thr Val Pro Ser Ser Ser Leu Gly Thr Lys Thr Tyr Thr Cys
        195                 200                 205
Asn Val Asp His Lys Pro Ser Asn Thr Lys Val Asp Lys Arg Val Glu
210                 215                 220
Ser Lys Tyr Gly Pro Pro Cys Pro Pro Cys Pro Ala Pro Glu Phe Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
Gln Glu Asp Pro Glu Val Gln Phe Asn Trp Tyr Val Asp Gly Val Glu
        275                 280                 285
Val His Asn Ala Lys Thr Lys Pro Arg Glu Glu Gln Phe Asn Ser Thr
290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Gly Leu Pro Ser Ser
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Gln Glu Glu Met Thr Lys Asn Gln Val
        355                 360                 365
Ser Leu Thr Cys Leu Val Lys Gly Phe Tyr Pro Ser Asp Ile Ala Val
370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Arg Leu Thr
                405                 410                 415
Val Asp Lys Ser Arg Trp Gln Glu Gly Asn Val Phe Ser Cys Ser Val
            420                 425                 430
Met His Glu Ala Leu His Asn His Tyr Thr Gln Lys Ser Leu Ser Leu
        435                 440                 445
Ser Leu Gly

<210> SEQ ID NO 10
<211> LENGTH: 219
<212> TYPE: PRT
<213> ORGANISM: Artificial Sequence
<220> FEATURE:
<223> OTHER INFORMATION: LC

<400> SEQUENCE: 10

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 11
<211> LENGTH: 207
<212> TYPE: PRT
<213> ORGANISM: Artificial Sequence
<220> FEATURE:
<223> OTHER INFORMATION: hIL-4Ralpha

<400> SEQUENCE: 11

```
Met Lys Val Leu Gln Glu Pro Thr Cys Val Ser Asp Tyr Met Ser Ile
1               5                   10                  15

Ser Thr Cys Glu Trp Lys Met Asn Gly Pro Thr Asn Cys Ser Thr Glu
            20                  25                  30

Leu Arg Leu Leu Tyr Gln Leu Val Phe Leu Leu Ser Glu Ala His Thr
        35                  40                  45

Cys Ile Pro Glu Asn Asn Gly Gly Ala Gly Cys Val Cys His Leu Leu
    50                  55                  60

Met Asp Asp Val Val Ser Ala Asp Asn Tyr Thr Leu Asp Leu Trp Ala
65                  70                  75                  80
```

```
                                                -continued

Gly Gln Gln Leu Leu Trp Lys Gly Ser Phe Lys Pro Ser Glu His Val
                 85                  90                  95

Lys Pro Arg Ala Pro Gly Asn Leu Thr Val His Thr Asn Val Ser Asp
            100                 105                 110

Thr Leu Leu Leu Thr Trp Ser Asn Pro Tyr Pro Pro Asp Asn Tyr Leu
            115                 120                 125

Tyr Asn His Leu Thr Tyr Ala Val Asn Ile Trp Ser Glu Asn Asp Pro
            130                 135                 140

Ala Asp Phe Arg Ile Tyr Asn Val Thr Tyr Leu Glu Pro Ser Leu Arg
145                 150                 155                 160

Ile Ala Ala Ser Thr Leu Lys Ser Gly Ile Ser Tyr Arg Ala Arg Val
                165                 170                 175

Arg Ala Trp Ala Gln Cys Tyr Asn Thr Thr Trp Ser Glu Trp Ser Pro
            180                 185                 190

Ser Thr Lys Trp His Asn Ser Tyr Arg Glu Pro Phe Glu Gln His
            195                 200                 205
```

METHODS FOR TREATING SEVERE ATOPIC DERMATITIS BY ADMINISTERING AN IL-4R INHIBITOR

CROSS-REFERENCE TO RELATED APPLICATIONS

This application claims the benefit under 35 U.S.C. § 119(e) of U.S. provisional application No. 62/397,988, filed on Sep. 22, 2016; 62/442,083, filed on Jan. 4, 2017; 62/443,819, filed on Jan. 9, 2017; 62/445,774, filed on Jan. 13, 2017; and 62/519,896, filed on Jun. 15, 2017, and under 35 U.S.C. § 119(b) of European application No. EP17306081, filed on Aug. 18, 2017, the disclosures of each herein incorporated by reference in their entireties.

SEQUENCE STATEMENT

The instant application contains a Sequence Listing, which has been submitted electronically in ASCII format and is hereby incorporated by reference in its entirety. Said ASCII copy, created on Sep. 11, 2017, is named SequenceList_29.TXT and is 10.9 kilobytes in size.

FIELD OF THE INVENTION

The present invention relates to methods for treating atopic dermatitis. More specifically, the invention relates to the administration of an interleukin-4 receptor (IL-4R) inhibitor in a subject in need thereof.

BACKGROUND

Atopic dermatitis (AD) is a chronic/relapsing inflammatory skin disease characterized by intense pruritus (i.e., itchiness), xerosis (skin dryness), and eczematous lesions whose features include erythema, infiltration/papulation, oozing with crusting, excoriations, and lichenification. It is often associated with other atopic disorders, such as allergic rhinitis and asthma. Severe disease can be extremely disabling due to several factors: major psychological problems, significant sleep loss, and impaired quality of life (QOL) that lead to a high socioeconomic cost. An estimated 2% to 10% of adults are affected by AD (Bieber 2008, N. Engl. J. Med. 358:1483-94).

The pathophysiology of AD is influenced by a complex interplay between inflammation, environmental factors, genetics and skin barrier dysfunction.

AD is the most common inflammatory skin disease in childhood (Illi et al 2004, J. Allergy Clin. Immunol. 113: 925-31). The disease usually presents during early infancy and childhood, but it can persist into or start in adulthood (Kay et al 1994, J. Am. Acad. Dermatol. 30: 35-9). The disease affects 15 to 30% of children and 2 to 10% of adults in industrialized countries (Bieber 2008, N. Engl. J. Med. 358: 1483-94). Phase 1 of the International Study of Asthma and Allergies in Childhood showed a 1-year period prevalence rate as high as 20% in Australia, England, and Scandinavia (Williams et al 1999, J. Allergy Clin. Immunol. 103: 125-38). Often AD constitutes the first step of atopic march (progression from one atopic disease to another). Approximately up to 60% of AD patients have concomitant asthma or allergic rhinitis or food allergy (Hong et al 2012, Envt. Health Toxicol. 27: e2012006).

Topical corticosteroids (TCS) are overwhelmingly the most frequently prescribed class of drugs for AD patients. However, long-term application of TCS is not recommended because of the risk of skin atrophy, dyspigmentation, acneiform eruptions, and risks associated with systemic absorption (e.g., hypothalamic pituitary axis effects, Cushing's disease, etc.). Topical calcineurin inhibitors (TCI) are generally effective and safe as short-term treatments, but concerns of skin malignancies and increased risk of lymphomas have prompted regulatory authorities to require a warning regarding the long-term safety of topical tacrolimus and pimecrolimus in their prescribing information. Repeated application of any topical therapy over a long period of time or to large surface areas also leads to reduced patient compliance. First generation antihistamines are widely prescribed for acute symptomatic treatment of pruritus, although their effectiveness is limited and largely attributed to their sedating effect. Oral immunosuppressants (Schmitt et al 2007, JEADV 21: 606-619) and glucocorticoids are effective, but are sometimes associated with severe toxicity and side effects, thus limiting their use to short courses and/or intermittent therapy. No systemic agents are approved in the treatment of AD in children. All systemic agents are used off label (cyclosporine, methotrexate, azathioprine, mycophenolate mofetil, systemic corticosteroids) and lack evidence basis of use. All of these agents have a broad immunosuppressive effect which predisposes the patients to serious infections and increased risk of malignancies if used for prolonged periods. Other reported significant side effects with these agents include gastritis, stunted growth, diabetes, weight gain, hypertension, osteoporosis and adrenal suppression (corticosteroids), nephrotoxicity, hypertension, tremor, hypertrichosis, headache, gingival hyperplasia (cyclosporine), gastrointestinal disturbances, ulcerative stomatitis, myelosuppression, hepatotoxicity and pulmonary fibrosis (methotrexate), hypersensitivity reactions, elevated liver enzymes and leukopenia (azathioprine). Moreover, a high proportion of patients in which disease is initially controlled by systemic agents suffer from relapse once therapy is discontinued (Granlund et al 1995, Br. J. Dermatol. 132: 106-112; Schmitt et al 2009, Br. J. Dermatol. 162: 661-8).

Cyclosporine A (CSA), a current therapy for severe AD in some regions, is a potent immunosuppressant affecting both humoral and cellular immune responses. This results in increased susceptibility to infections and decreased cancer immunosurveillance. Other commonly recognized toxicities include hypertension and impaired renal and hepatic function. In addition, CSA interacts with other commonly used medicines potentially affecting their metabolism and effect. Patients' disease often rebounds when the treatment is stopped, especially after the administration of systemic glucocorticoids (Schmitt et al 2009, Brit J Dermatol journal compilation:1-8, Schram 2012, Allergy 67:99-106, Akhavan 2008, Semin Cutan Med Surg 2008; 27:151-155). Biological agents including tumor necrosis factor α (TNF) inhibitors (e.g., infliximab, etanercept), IgE inhibitors (e.g., omalizumab), IL-5 inhibitors (e.g., mepolizumab), and CD11a inhibitors (e.g., efalizumab) have generally been ineffective in clinical trials. Therefore, there exists a significant unmet medical need for an alternative treatment for AD, specifically severe AD in patients that are candidates for systemic therapy.

BRIEF SUMMARY OF THE INVENTION

According to certain aspects of the present invention, methods are provided for treating, preventing and/or reducing the severity of a symptom of atopic dermatitis (AD), including moderate-to-severe AD and severe AD. Certain embodiments of the invention pertain to methods for treating patients with severe AD that is resistant to treatment or is inadequately controlled by systemic therapy (including a systemic immunosuppressant). In some embodiments, the present invention includes methods of treating patients with severe AD that is uncontrolled despite treatment with a systemic therapeutic agent. In some embodiments, the present invention includes methods of treating patients with severe AD for whom treatment with a systemic therapeutic agent (e.g., a systemic immunosuppressant) is medically inadvisable. The methods of the present invention comprise administering to a subject or a patient in need thereof one or more doses of a pharmaceutical composition comprising a therapeutically effective amount of an interleukin-4 receptor (IL-4R) inhibitor. In certain embodiments, the IL-4R inhibitor is administered as monotherapy. In other embodiments, the IL-4R inhibitor is administered in combination with a topical therapy (such as a topical corticosteroid or a topical calcineurin inhibitor).

In certain embodiments, the systemic therapeutic agent is an immunosuppressant selected from the group consisting of cyclosporine A, methotrexate, mycophenolate mofetil, azathioprine, an oral corticosteroid, and interferon-gamma.

In certain embodiments, the present invention includes methods to treat severe AD or to improve at least one AD-associated parameter in a patient, the methods comprising administering a pharmaceutical composition comprising a therapeutically effective amount of an antibody or antigen-binding fragment thereof that binds IL-4R, and determining an improvement in an AD-associated parameter. In certain embodiments, the administration of the IL-4R inhibitor results in an improvement in one or more AD-associated parameters selected from the group consisting of Investigators Global Assessment (IGA); Body Surface Area Involvement of Atopic Dermatitis (BSA); Eczema Area and Severity Index (EASI); Scoring atopic dermatitis (SCORAD); 5-D Pruritus Scale; and Pruritus Numeric Rating Scale (NRS). In certain embodiments, administration of the IL-4R inhibitor results in an improvement in at least one patient-related outcome selected from the group consisting of Global Individual Signs Score (GISS), Patient Oriented Eczema Measure (POEM), Patient-assessed Hospital Anxiety and Depression Scale (HADS) and Patient-reported Dermatology Life Quality Index (DLQI).

According to certain aspects, the present invention provides methods for treating a patient with severe AD or for improving at least one AD-associated parameter in a patient with AD wherein the patient has an attribute or is selected on the basis of an attribute selected from the group consisting of: (i) the patient has a baseline IGA score=4; (ii) the patient has a baseline IGA score 3; (iii) the patient is a candidate for systemic therapy; (iv) the patient has disease that is uncontrolled by topical AD therapy; (v) the patient has a documented history of inadequate response to topical AD therapy or for whom topical therapy is inadvisable due to adverse side effects or safety risks; (vi) the patient has been previously treated with a medication or procedure selected from the group consisting of a topical corticosteroid, a topical calcineurin inhibitor, an anti-histamine, an emollient, a dermatological therapeutic, a systemic glucocorticoid, a non-steroidal systemic immunosuppressant, cyclosporine A, azathioprine, ultraviolet (UV) light therapy, and phototherapy; and (vii) the patient has a concomitant disease or disorder selected from the group consisting of food allergy, asthma, seasonal allergy, allergic rhinitis, house dust allergy, and allergic conjunctivitis. The methods, according to this aspect, comprise administering a pharmaceutical composition comprising a therapeutically effective amount of an IL-4R inhibitor to the patient in need thereof. In certain embodiments, the administration results in one or more of the following effects: (a) more than 70% reduction from baseline in EASI score; (b) more than 50% reduction from baseline in pruritus NRS from week 2 after administration of the first dose; (c) a 4-point reduction from baseline in pruritus NRS as early as week 2 after administration of first dose; (d) patient achieves IGA of 0 or 1 ("clear" or "almost clear") with a reduction of points from baseline on a 0 to 4 IGA scale; (e) an improvement in the quality of life of the patient. In certain embodiments, the IL-4R inhibitor is administered as monotherapy. In other embodiments, the IL-4R inhibitor is administered in combination with a topical therapy (such as a topical corticosteroid or a topical calcineurin inhibitor).

According to certain aspects, the present invention provides methods for treating or reducing pruritus in a patient with severe AD wherein the patient is a candidate for systemic therapy. The methods, according to these aspects, comprise selecting a patient diagnosed with severe AD wherein the patient is resistant, inadequately responsive or intolerant to a systemic immunosuppressant; and administering to the patient in need thereof one or more doses of an IL-4R inhibitor. In certain embodiments, the IL-4R inhibitor is administered as monotherapy. In other embodiments, the IL-4R inhibitor is administered in combination with a topical therapy (such as a topical corticosteroid or a topical calcineurin inhibitor). In certain embodiments, the administration of the IL-4R inhibitor results in more than 70% reduction from baseline in EASI score, more than 50% reduction from baseline in pruritus NRS, a ≥4-point reduction from baseline in pruritus NRS, and/or a reduction of ≥2 points from baseline on a 0 to 4 IGA scale.

According to certain aspects, the present invention includes methods of treating a patient with severe AD. The methods, according to these aspects, comprise selecting a patient with severe AD, wherein the patient has been previously treated with a therapeutic selected from the group consisting of cyclosporine A, an IgE inhibitor, a TNFalpha inhibitor, a CD11a inhibitor, a CD20 inhibitor, an antibiotic, an IL-4R inhibitor (e.g., an anti-IL-4R antibody such as dupilumab), a systemic immunosuppressant, a topical corticosteroid, an oral corticosteroid, calcineurin inhibitor and phototherapy; and administering one or more doses of an IL-4R inhibitor to the patient in need thereof.

In certain embodiments, the present invention includes methods to reduce the dependence on topical corticosteroids (TCS) in a patient with severe AD, the methods comprising administering one or more doses of an IL-4R inhibitor to the subject in need thereof. In certain further embodiments, a medium-potency or high-potency TCS is concomitantly administered with the IL-4R inhibitor. In one further embodiment, the amount of TCS is gradually reduced by at least 20%, at least 30%, at least 40% or at least 50% upon administration of the first dose of the IL-4R inhibitor.

According to certain aspects, the present invention includes methods to reduce flares or AD exacerbations, the methods comprising selecting a patient with severe AD and administering one or more doses of an IL-4R inhibitor to the patient in need thereof. In certain embodiments, the patient has refractory AD or has relapsed after therapy with a systemic therapeutic agent (e.g., a systemic immunosuppressant).

According to certain aspects, the present invention includes methods to treat AD or to reduce pruritus or to improve an AD-associated parameter, the methods comprising selecting a patient with moderate-to-severe or severe AD wherein the patient has been previously treated more than 5 weeks ago, more than 8 weeks ago, more than 13 weeks ago, or more than 20 weeks ago with an IL-4R inhibitor (e.g., an anti-IL-4R antibody such as dupilumab) and re-treating the patient in need thereof with one or more doses of an IL-4R inhibitor wherein the re-treatment leads to more than 70% reduction from baseline in EASI score, more than 50% reduction from baseline in pruritus NRS, a ≥4-point reduction from baseline in pruritus NRS, and/or a reduction of ≥2 points from baseline on a 0 to 4 IGA scale. In certain embodiments, each dose of the IL-4R inhibitor comprises about 50-600 mg and is administered 1, 2, 3 or 4 weeks after the immediately preceding dose.

According to certain aspects, the present invention includes methods to treat AD or to improve at least one AD-associated parameter in a patient with AD, the methods comprising (a) selecting a patient with AD wherein the patient has an attribute selected from the group consisting of: (i) the patient has a baseline IGA score=4; (ii) the patient has a baseline IGA score ≥3; (iii) the patient is between 6 and 18 years of age; (iv) the patient has disease that is uncontrolled by topical AD therapy; (v) the patient has a documented history of inadequate response to topical AD therapy or for whom topical therapy is inadvisable due to adverse side effects or safety risks; (vi) the patient has been previously treated with a medication or procedure selected from the group consisting of a topical corticosteroid, a topical calcineurin inhibitor, an anti-histamine, an emollient, a dermatological therapeutic, a systemic glucocorticoid, a non-steroidal systemic immunosuppressant, cyclosporine A, azathioprine, UV light therapy, and phototherapy; and (vii) the patient has a concomitant disease or disorder selected from the group consisting of food allergy, asthma, seasonal allergy, allergic rhinitis, house dust allergy, and allergic conjunctivitis; and (b) administering one or more doses of a therapeutically effective amount of an IL-4R inhibitor to the patient in need thereof. In certain embodiments, each dose of the IL-4R inhibitor comprises 1, 2, 3, 4 or 5 mg/kg of the patient's body weight, and each dose is administered 1-4 weeks after the immediately preceding dose.

According to certain embodiments, the methods of the present invention comprise administering one or more doses of an IL-4R inhibitor to a subject in need thereof. In certain embodiments, the methods of the present invention comprise administering about 10 mg to about 600 mg of an IL-4R inhibitor as an initial dose followed by one or more secondary doses, each secondary dose comprising 25 to 400 mg of an IL-4R inhibitor. In certain embodiments, the initial dose and the one or more secondary doses each comprise about 10 mg to about 600 mg of the IL-4R inhibitor. In certain embodiments, the IL-4R inhibitor is administered at an initial dose of 600 mg followed by one or more secondary doses wherein each secondary dose comprises 300 mg. According to this aspect of the invention, the IL-4R inhibitor may be administered to the subject at a dosing frequency of, e.g., once a week, once in 2 weeks, once in 3 weeks or once in 4 weeks. In one embodiment, each secondary dose is administered 1 week after the immediately preceding dose. In one embodiment, each secondary dose is administered 2 weeks after the immediately preceding dose. In certain embodiments, the methods of the present invention comprise administering an IL-4R inhibitor to a subject in need thereof wherein the IL-4R inhibitor comprises about 1-10 mg/kg of the subject's body weight. In certain embodiments, the subject in need thereof is administered one or more doses of the IL-4R inhibitor wherein each dose comprises 1, 2, 4, 5 or 10 mg/kg of the subject's body weight and wherein each dose is administered 1-4 weeks after the immediately preceding dose.

Exemplary IL-4R inhibitors that can be used in the context of the methods of the present invention include, e.g., small molecule chemical inhibitors of IL-4R or its ligands (IL-4 and/or IL-13), or biological agents that target IL-4R or its ligands. According to certain embodiments, the IL-4R inhibitor is an antigen-binding protein (e.g., antibody or antigen-binding fragment thereof) that binds the IL-4Rα chain and blocks signaling by IL-4, IL-13, or both IL-4 and IL-13. In one embodiment, the antibody or antigen-binding fragment thereof that specifically binds IL-4R comprises complementarity determining regions (CDRs) in a heavy chain variable region (HCVR)/light chain variable region (LCVR) sequence pair of SEQ ID NOs: 1/2. In certain embodiments, the antibody or antigen-binding fragment thereof comprises a heavy chain CDR (HCDR1) having amino acid sequence of SEQ ID NO: 3, a HCDR2 having amino acid sequence of SEQ ID NO: 4, a HCDR3 having amino acid sequence of SEQ ID NO: 5, a light chain CDR (LCDR1) having amino acid sequence of SEQ ID NO: 6, a LCDR2 having amino acid sequence of SEQ ID NO: 7, and a LCDR3 having amino acid sequence of SEQ ID NO: 8. One such type of antigen-binding protein that can be used in the context of the methods of the present invention is an anti-IL-4Rα antibody such as dupilumab.

In some embodiments, the IL-4R inhibitor is administered subcutaneously, intravenously, or intraperitoneally to the subject.

In certain embodiments, the present invention provides use of an IL-4R inhibitor of the invention in the manufacture of a medicament to treat moderate-to-severe or severe AD or to reduce pruritus in a patient, wherein the patient is a candidate for systemic therapy (e.g., a systemic immunosuppressant) In certain embodiments, the patient is resistant or intolerant to systemic therapy or for whom systemic therapy is inadvisable due to safety and health risks coupled with suboptimal efficacy. In certain embodiments, the present invention provides use of an IL-4R inhibitor of the invention in the manufacture of a medicament reduce dependence on topical corticosteroids in a patient with severe AD. In certain embodiments, the present invention provides use of an IL-4R inhibitor in a method to treat severe AD or to reduce pruritus in a patient with severe AD, wherein the IL-4R inhibitor is administered to a subject in need thereof. In certain embodiments, the present invention provides use of an IL-4R inhibitor in a method to reduce dependence on topical corticosteroids in a subject with severe AD, wherein the IL-4R inhibitor is administered to the subject in need thereof.

Other embodiments of the present invention will become apparent from a review of the ensuing detailed description.

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.). As used herein, the terms "treat", "treating", or the like, mean to alleviate symptoms, eliminate the causation of symptoms either on a temporary or permanent basis, or to prevent or slow the appearance of symptoms of the named disorder or condition.

Although any methods and materials similar or equivalent to those described herein can be used in the practice of the present invention, the preferred methods and materials are now described. All publications mentioned herein are incorporated herein by reference to describe in their entirety.

Methods for Treating Severe Atopic Dermatitis

The present invention includes methods which comprise administering to a subject in need thereof a therapeutic composition comprising an IL-4R inhibitor. As used herein, the expression "a subject in need thereof" means a human or non-human animal that exhibits one or more symptoms or indicia of atopic dermatitis, and/or who has been diagnosed with atopic dermatitis.

"Atopic dermatitis" (AD), as used herein, means an inflammatory skin disease characterized by intense pruritus (e.g., severe itch) and by scaly and dry eczematous lesions. The term "atopic dermatitis" includes, but is not limited to, AD caused by or associated with epidermal barrier dysfunction, allergy (e.g., allergy to certain foods, pollen, mold, dust mite, animals, etc.), radiation exposure, and/or asthma. The present invention encompasses methods to treat patients with moderate-to-severe or severe AD. As used herein, "moderate-to-severe AD", is characterized by intensely pruritic, widespread skin lesions that are often complicated by persistent bacterial, viral or fungal infections. Moderate-to-severe AD also includes chronic AD in patients. In many cases, the chronic lesions include thickened plaques of skin, lichenification and fibrous papules. Patients affected by moderate-to-severe AD also, in general, have more than 20% of the body's skin affected, or 10% of skin area in addition to involvement of the eyes, hands and body folds. Moderate-to-severe AD is also considered to be present in patients who require frequent treatment with topical corticosteroids. A patient may also be said to have moderate-to-severe AD when the patient is resistant or refractory to treatment by either a topical corticosteroid or a calcineurin inhibitor.

In certain preferred embodiments, the term "a subject in need thereof" refers to patients with severe AD. As used herein, "severe AD" refers to chronic relapsing AD that is refractory to treatment with medium-potency and high-potency TCS and/or immunosuppressant therapy. Severe AD is also characterized by chronic intensely pruritic lesions affecting more than 20% of the body surface area. In certain embodiments, the term refers to chronic AD according to the Eichenfield criteria (Eichenfield et al 2014, J. Am. Acad. Dermatol. 70: 338-351) for which treatment with potent topical corticosteroids (TCS) is indicated. In certain embodiments, the term includes patients with chronic AD that are resistant to treatment with systemic corticosteroids and/or non-steroidal immunosuppressants. A patient with severe AD may also show frequent exacerbations or flares of the disease. In certain embodiments, the term "severe AD" refers to patients with Investigators Global Assessment (IGA) score of 4.

As used herein, "flare", also referred to as "exacerbation" refers to an increase in signs and/or symptoms leading to escalation of therapy, which can be an increase in the dose of an immunosuppressant therapy (e.g., cyclosporine A), a switch to a higher-potency class of TCS, or the start of another oral immunosuppressive drug. In certain embodiments, the present invention includes methods to reduce the number of flares or exacerbations in a patient with severe AD, the methods comprising administering a therapeutically effective amount of an IL-4R inhibitor to the patient in need thereof.

In certain embodiments, the term "subject in need thereof" includes subjects resistant, non-responsive or inadequately responsive to treatment with a systemic immunosuppressant. The present invention includes methods to treat AD in subjects or patients resistant, non-responsive or inadequately responsive to treatment with a systemic immunosuppressant. The term "resistant, non-responsive or inadequately responsive to a systemic immunosuppressant", as used herein, refers to subjects or patients with AD who have been treated with a systemic immunosuppressant and wherein the immunosuppressant does not have a therapeutic effect. In some embodiments, the term refers to reduced patient compliance and/or toxicity and side effects and/or ineffectiveness of the administered immunosuppressant to reduce, ameliorate or decrease the symptoms of AD. In some embodiments, the term refers to patients suffering from moderate-to-severe AD or severe AD who are refractory to treatment by a systemic immunosuppressant. In some embodiments, the term refers to patients with AD which is uncontrolled despite treatment with an immunosuppressant. In some embodiments, the patients who are "resistant, non-responsive or inadequately responsive to a systemic immunosuppressant" may show no improvement in one or more AD-associated parameters. Examples of AD-associated parameters are described elsewhere herein. For example, treatment with a systemic immunosuppressant may result in no decrease in pruritus or Eczema Area and Severity Index (EASI) score or Body Surface Area (BSA) score. In some embodiments, the term refers to patients with severe AD that have been treated with systemic immunosuppressant, but have since relapsed and/or show increased AD exacerbations or flares. In certain embodiments, the term refers to patients with severe AD for whom immunosuppressant therapy is inadvisable due to safety and health risks to the patient coupled with suboptimal efficacy. In some embodiments, the present invention includes methods to treat moderate-to-severe AD or severe AD in patients who have been treated earlier with a systemic immunosuppressant for 1 month and do not show a decrease in one or more AD-associated parameters. For example, the present methods may be used to treat a patient with chronic relapsing AD who has been treated with a systemic immunosuppressant and has a Body Surface Area (BSA) score of 10% or an Investigators Global Assessment (IGA) score ≥3.

In certain embodiments, the term "subject in need thereof" includes patients with severe AD whose disease cannot be adequately controlled with TCS, who are not adequately controlled with, or are intolerant to oral immunosuppressant, or when immunosuppressant treatment is currently deemed not medically advisable by a physician, according to the following: (A) No prior immunosuppressant exposure (who are not currently a candidate for such treatment) due to:

Medical contraindications;
    Hypersensitivity to immunosuppressant active substance or excipients;
    Use of concomitant medications prohibited with immunosuppressant; or Increased susceptibility to immunosuppressant induced renal damage, increased risk of serious infections, etc.

Or (B) Previously exposed to immunosuppressant and for whom immunosuppressant should not be continued or restarted due to:

Previous intolerance and/or unacceptable toxicity

Inadequate response—defined as flare of AD on immunosuppressant tapering after a maximum of 6 weeks of high dose (5 mg/kg/day) to maintenance dose (2 to 3 mg/kg/day) or a flare after a minimum of 3 months on maintenance dose. Flare is defined as increase in signs and/or symptoms leading to escalation of therapy, which can be an increase in immunosuppressant dose, a switch to a higher-potency class of TCS, or the start of another oral immunosuppressive drug; or Requirement for immunosuppressant at doses or duration beyond that specified in the prescribing information.

In certain embodiments, the term "subject in need thereof" includes patients with moderate-to-severe or severe AD who are candidates for systemic therapy. As used herein, the term "systemic therapy" refers to systemically administered therapeutic agents (e.g., orally administered corticosteroids) and other immunosuppressant or immunomodulatory agents. In the context of the present invention, the term "systemic immunosuppressant" includes, but is not limited to, cyclosporine A, methotrexate, mycophenolate mofetil, azathioprine, systemic or oral corticosteroids, and interferon-gamma. In certain embodiments, the term also includes immunobiologics such as tumor necrosis factor alpha (TNFα) inhibitors (e.g., an anti-TNFα antibody such as infliximab), CD11a inhibitors (e.g., an anti-CD11a antibody such as efalizumab), IgE inhibitors (e.g., omalizumab), CD20 inhibitors (e.g., rituximab). Systemic therapy including systemic immunosuppressants may be used for short-term treatment of flares or as a temporary measure to control disease, but their use is limited by significant side-effects, e.g., growth retardation in children, Cushing's syndrome, hypertension, glucose intolerance, myopathy, osteonecrosis, glaucoma and cataracts. Use of systemic immunosuppressants also carries the risk of rebound phenomenon, wherein symptoms of the disease may worsen significantly following cessation of treatment. In certain embodiments, the terms "systemic therapy", "systemic therapeutic agent" and "systemic immunosuppressant" have been used interchangeably throughout this disclosure.

In certain embodiments, the term "subject in need thereof" includes patients with moderate-to-severe or severe AD who have been administered one or more TCS for more than 6 months, more than 1 year, more than 2 years, more than about 5 years, more than about 7 years, or more than about 10 years, in addition to periodic treatment with an immunosuppressant. In certain embodiments, the term "subject in need thereof" includes patients with moderate-to-severe or severe AD that have been previously treated with a therapeutic selected from the group consisting of cyclosporine A, an IgE inhibitor, a TNFalpha inhibitor, a CD11a inhibitor, a CD20 inhibitor, an IL-4R inhibitor (e.g., an anti-IL-4R antibody such as dupilumab), an antibiotic, a systemic immunosuppressant, a topical corticosteroid, an oral corticosteroid, calcineurin inhibitor and phototherapy. The patients may desire to minimize or avoid the adverse side effects of the TCS and/or immunosuppressant. The present invention includes methods to treat moderate-to-severe or severe AD in a patient, the methods comprising administering an IL-4R inhibitor concomitantly with a TCS wherein the dosage is adjusted to minimize or prevent adverse side effects of the TCS. In certain embodiments, the present invention includes methods to reduce dependence on TCS in a patient with moderate-to-severe or severe AD; the methods comprising administering a therapeutically effective amount of an IL-4R inhibitor concomitantly with a potent TCS wherein the amount of TCS used by the patient is reduced by about 50% as compared to a patient not administered the IL-4R inhibitor. In certain embodiments, the present invention includes methods to reduce dependence on TCS in a patient with moderate-to-severe or severe AD, the methods comprising administering a therapeutically effective amount of an IL-4R inhibitor concomitantly with a potent TCS wherein the amount of TCS used by the patient is reduced by at least 20%, at least 30%, at least 40% or at least 50% as compared to the amount used by the patient before treatment with the IL-4R inhibitor. In certain embodiments, the administration of an IL-4R inhibitor and a TCS results in additive or synergistic activity in treating AD as compared to monotherapy.

The term "TCS", as used herein includes group I, group II, group III and group IV topical corticosteroids. According to the Anatomical Therapeutic Classification System of World Health Organization, the corticosteroids are classified as weak (group I), moderately potent (Group II) and potent (Group III) and very potent (Group IV), based on their activity as compared to hydrocortisone. Group IV TCS (very potent) are up to 600 times as potent as hydrocortisone and include clobetasol propionate and halcinonide. Group III TCS (potent) are 50 to 100 times as potent as hydrocortisone and include, but are not limited to, betamethasone valerate, betamethasone dipropionate, diflucortolone valerate, hydrocortisone-17-butyrate, mometasone furoate, and methylprednisolone aceponate. Group II TCS (moderately potent) are 2 to 25 times as potent as hydrocortisone and include, but are not limited to, clobetasone butyrate, and triamcinolone acetonide. Group I TCS (mild) includes hydrocortisone.

Patients with severe AD are often prescribed medium-potency or high-potency TCS for treatment of AD. Such treatment may be, for example, for more than 2 months, for more than 3 months, more than 4 months, more than 5 months, or more than 6 months. It is known in prior art that treatment with TCS leads to adverse side-effects. In certain aspects, the present invention includes methods to reduce use of TCS or dependence on TCS and/or to reduce the adverse side-effects of TCS in a patient with severe AD, the methods comprising administering one or more doses of an IL-4R inhibitor to the patient in need thereof. In certain embodiments, the IL-4R inhibitor is administered in combination with a medium-potency or high-potency TCS, wherein the amount of TCS administered is gradually reduced such that the patient's severe AD is treated and/or one or more AD-associated parameters is significantly improved as well as the side effects and toxicity due to TCS are minimized or prevented. In certain embodiments, the present invention includes methods to reduce or eliminate the risk of rebound upon TCS or immunosuppressant reduction or discontinuation, the methods comprising selecting a patient with severe AD that is uncontrolled with a background therapy and administering one or more doses of IL-4R inhibitor to the patient in need thereof. In certain further embodiments, the patient is initially administered one or more doses of IL-4R inhibitor in combination with a concomitantly administered background therapy; followed by gradually reducing the background therapy. In certain embodiments, the background therapy comprises a therapeutic agent selected from the group consisting of TCS, calcineurin inhibitors, a systemic immunosuppressant and emollients. In one embodiment, the patient with severe AD is earlier treated with a systemic immunosuppressant wherein the systemic immunosuppressant is cyclosporine A. In certain embodiments, the amount of the background therapy is reduced by at least 20%, at least 30%, at 40% or at least 50% as compared to a patient that is not administered an IL-4R inhibitor.

The present invention includes methods for treating severe AD by improving one or more atopic dermatitis (AD)-associated parameters in a subject in need thereof, wherein the methods comprise selecting a patient with severe AD, wherein the patient is resistant, inadequately responsive or intolerant to systemic immunosuppressant therapy, and administering a pharmaceutical composition comprising an IL-4R inhibitor to the subject. In one embodiment, the pharmaceutical composition comprising an IL-4R inhibitor is administered in combination with a potent TCS.

Examples of "AD-associated parameters" include: (a) Investigators Global Assessment (IGA); (b) Body Surface Area Involvement of Atopic Dermatitis (BSA); (c) Eczema Area and Severity Index (EASI); (d) SCORAD; (e) 5-D Pruritus Scale; and (f) Pruritus Numeric Rating Scale (NRS). An "improvement in an AD-associated parameter" means a decrease from baseline of one or more of IGA, BSA, EASI, SCORAD, 5-D Pruritus Scale, or NRS. As used herein, the term "baseline," with regard to an AD-associated parameter, means the numerical value of the AD-associated parameter for a subject prior to or at the time of administration of a pharmaceutical composition of the present invention.

To determine whether an AD-associated parameter has "improved," the parameter is quantified at baseline and at one or more time points after administration of the pharmaceutical composition of the present invention. For example, an AD-associated parameter may be measured at day 1, day 2, day 3, day 4, day 5, day 6, day 7, day 8, day 9, day 10, day 11, day 12, day 14, day 15, day 22, day 25, day 29, day 36, day 43, day 50, day 57, day 64, day 71, day 85; or at the end of week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, week 24, or longer, after the initial treatment with a pharmaceutical composition of the present invention. The difference between the value of the parameter at a particular time point following initiation of treatment and the value of the parameter at baseline is used to establish whether there has been an "improvement" (e.g., a decrease) in the AD associated parameter. AD-associated parameters are described in US Patent Publication No. US20140072583, incorporated herein in its entirety. In the context of the present invention, "a subject in need thereof" may include, e.g., subjects who, prior to treatment, exhibit (or have exhibited) one or more AD-associated parameters such as, e.g., elevated IGA, BSA, EASI, SCORAD, 5D-Pruritus, and/or NRS score. For example, the methods of the present invention comprise administering an IL-4R inhibitor to patients with IGA≥3 or ≥4; or BSA more than 10%.

According to one aspect, the present invention provides methods of treating moderate-to-severe or severe AD or reducing pruritus or improving an AD-associated parameter, the methods comprising: (1) selecting a patient with moderate-to-severe or severe AD wherein the patient has an attribute selected from the group consisting of: (a) patient has a documented history of inadequate response or intolerance to cyclosporine A (CsA); (b) patient has a baseline peak pruritus NRS ≥4; (c) patient has a baseline IGA score ≥3; (d) patient has a baseline IGA score=4; and (e) patient has a concurrent disease or disorder selected from the group consisting of asthma, allergic rhinitis, food allergy, allergic conjunctivitis, hives, allergy and environmental allergens; and (2) administering one or more doses of a therapeutically effective amount of an IL-4R inhibitor to the patient in need thereof. In certain embodiments, the administration of the IL-4R inhibitor leads to an effect selected from the group consisting of: (i) a decrease from baseline of more than 70% in EASI; (ii) a decrease from baseline of about 75% in EASI by Week 2 after administration of the first dose of the IL-4R inhibitor; (iii) a decrease from baseline of more than 50% in pruritus NRS by week 16 after administration of the first dose of the IL-4R inhibitor; (iv) ≥4-point improvement in peak pruritus NRS by week 2 after administration of the first dose of the IL-4R inhibitor; (v) a 2-point improvement in IGA score by week 16 after administration of the first dose of the IL-4R inhibitor; (vi) a decrease from baseline in IGA to achieve an IGA score of 0 or 1 by week 16 after administration of the first dose of the IL-4R inhibitor; (vii) a reduction in the number of flares or exacerbations; and (viii) reduction in the incidence of skin infections; and (vii) improvement of quality of life as determined by, for example, Dermatology Life Quality Index (DLQI) or any other patient-reported outcome disclosed herein. In certain embodiments, the IL-4R inhibitor is an anti-IL-4R antibody or antigen-binding fragment thereof (such as dupilumab). In certain embodiments, the IL-4R inhibitor is administered in combination with a second therapeutic agent. In certain embodiments, the second therapeutic agent is selected from the group consisting of topical corticosteroids and topical calcineurin inhibitors. In certain embodiments, each dose of the IL-4R inhibitor comprises 50-600 mg and each dose is administered one week or 2 weeks after the immediately preceding dose. In one embodiment, each dose of the anti-IL-4R antibody comprises 300 mg and wherein each dose is administered once a week or once in 2 weeks. In certain specific embodiments, the one or more doses comprise a first dose comprising 600 mg followed by one or more secondary doses wherein each secondary dose comprises 300 mg and wherein each secondary dose is administered 1 week or 2 weeks after the immediately preceding dose.

According to one aspect, the present invention includes methods for treating AD or for reducing pruritus or for improving an AD-associated parameter in a patient with moderate-to severe or severe AD wherein the patient has been previously treated with an IL-4R inhibitor (e.g., an anti-IL-4R antibody such as dupilumab). In certain embodiments, the patient has been previously treated more than 4 weeks ago, more than 8 weeks ago, more than 12 weeks ago or more than 20 weeks ago with dupilumab. In certain embodiments, the present invention includes methods to treat moderate-to-severe or severe AD in patients whose prior treatment with an IL-4R inhibitor has been interrupted more than 4 weeks ago, more than 8 weeks ago or more than 12 weeks ago. The methods, according to this aspect, comprise re-treating the patient in need thereof with an IL-4R inhibitor wherein the retreatment comprises administering one or more doses of the IL-4R inhibitor such that the patient's disease is treated or at least one AD-associated parameter is improved. In certain embodiments, the retreatment of the patient leads to more than 70% reduction from baseline in EASI score and/or more than 50% reduction from baseline in pruritus NRS score upon administration of the IL-4R inhibitor.

In certain embodiments, the methods of the present invention may be used to treat patients that show elevated levels of one or more AD-associated biomarkers (e.g., IgE). AD-associated biomarkers are described in US Patent Publication No. US20140072583, incorporated herein in its entirety. For example, the methods of the present invention comprise administering an IL-4R inhibitor to patients with elevated levels of IgE or TARC or periostin. In the context of the present invention, "a patient in need thereof" may include, e.g., subjects who, prior to treatment, exhibit (or have exhibited) an elevated level of one or more AD-associated biomarker such as, e.g., IgE and/or TARC. In certain embodiments, "a subject in need thereof" may include a subset of population which is more susceptible to AD or may show an elevated level of an AD-associated biomarker.

In some embodiments, the methods herein may be used to treat severe AD in children who are ≤1 year old. For example, the present methods may be used to treat infants who are less than 1 month, 1 month, 2 months, 3 months, 4 months, 5 months, 6 months, 7 months, 8 months, 9 months, 10 months, 11 months or less than 12 months old. In other embodiments, the present invention includes methods to treat children and/or adolescents who are ≤18 years old. For example, the present methods may be used to treat children or adolescents less than 17 years, 16 years, 15 years, 14 years, 13 years, 12 years, 11 years, 10 years, 9 years, 8 years, 7 years, 6 years, 5 years, 4 years, 3 years, or less than 2 years old.

According to certain aspects, the present invention includes methods for treating moderate-to-severe or severe atopic dermatitis (AD) or improving an AD-associated parameter, the method comprising: (a) selecting a patient with moderate-to-severe or severe AD wherein the patient has an attribute selected from the group consisting of: (i) the patient has a baseline IGA score=4; (ii) the patient has a baseline IGA score ≥3; (iii) the patient is between 6 and 18 years of age; (iv) the patient has disease that is uncontrolled by topical AD therapy; (v) the patient has a documented history of inadequate response to topical AD therapy or for whom topical therapy is inadvisable due to adverse side effects or safety risks; (vi) the patient has been previously treated with a medication or procedure selected from the group consisting of a topical corticosteroid, a topical calcineurin inhibitor, an anti-histamine, an emollient, a dermatological therapeutic, a systemic glucocorticoid, a non-steroidal systemic immunosuppressant, cyclosporine A, azathioprine, UV light therapy, and phototherapy; and (vii) the patient has a concomitant disease or disorder selected from the group consisting of food allergy, asthma, seasonal allergy, allergic rhinitis, house dust allergy, and allergic conjunctivitis; and (b) administering one or more doses of a therapeutically effective amount of an IL-4R inhibitor to the patient in need thereof. In certain embodiments, the administration of the IL-4R inhibitor leads to a therapeutic effect selected from the group consisting of: (i) more than 30% reduction from baseline in EASI score by week 2 after administration of the first dose of the IL-4R inhibitor; (ii) more than 50% reduction from baseline in pruritus NRS; and (iii) a reduction from baseline in IGA score to achieve an IGA score of 0 or 1 by week 12 after administration of the first dose of the IL-4R inhibitor. In certain embodiments, the IL-4R inhibitor is administered in combination with a second therapeutic agent selected from the group consisting of a topical corticosteroid, a topical calcineurin inhibitor, an anti-histamine, an emollient, an anti-bacterial therapeutic, and a therapeutic agent for obstructive airway disease, a lung disorder and/or allergic reaction.

Interleukin-4 Receptor Inhibitors

The methods of the present invention comprise administering to a subject in need thereof a therapeutic composition comprising an interleukin-4 receptor (IL-4R) inhibitor. As used herein, an "IL-4R inhibitor" (also referred to herein as an "IL-4R inhibitor," an "IL-4Rα antagonist," an "IL-4R blocker," an "IL-4Rα blocker," etc.) is any agent which binds to or interacts with IL-4Rα or an IL-4R ligand, and inhibits or attenuates the normal biological signaling function a type 1 and/or a type 2 IL-4 receptor. Human IL-4Rα has the amino acid sequence of SEQ ID NO: 11. A type 1 IL-4 receptor is a dimeric receptor comprising an IL-4Rα chain and a γc chain. A type 2 IL-4 receptor is a dimeric receptor comprising an IL-4Rα chain and an IL-13Rα1 chain. Type 1 IL-4 receptors interact with and are stimulated by IL-4, while type 2 IL-4 receptors interact with and are stimulated by both IL-4 and IL-13. Thus, the IL-4R inhibitors that can be used in the methods of the present invention may function by blocking IL-4-mediated signaling, IL-13-mediated signaling, or both IL-4- and IL-13-mediated signaling. The IL-4R inhibitors of the present invention may thus prevent the interaction of IL-4 and/or IL-13 with a type 1 or type 2 receptor.

Non-limiting examples of categories of IL-4R inhibitors include small molecule IL-4R inhibitors, anti-IL-4R aptamers, peptide-based IL-4R inhibitors (e.g., "peptibody" molecules), "receptor-bodies" (e.g., engineered molecules comprising the ligand-binding domain of an IL-4R component), and antibodies or antigen-binding fragments of antibodies that specifically bind human IL-4Rα. As used herein, IL-4R inhibitors also include antigen-binding proteins that specifically bind IL-4 and/or IL-13.

Anti-IL-4Rα Antibodies and Antigen-Binding Fragments Thereof

According to certain exemplary embodiments of the present invention, the IL-4R inhibitor is an anti-IL-4Rα antibody or antigen-binding fragment thereof. The term "antibody," as used herein, includes immunoglobulin molecules comprising four polypeptide chains, two heavy (H) chains and two light (L) chains inter-connected by disulfide bonds, as well as multimers thereof (e.g., IgM). In a typical antibody, each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-IL-4R antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (v) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The term "antibody," as used herein, also includes multispecific (e.g., bispecific) antibodies. A multispecific antibody or antigen-binding fragment of an antibody will typically comprise at least two different variable domains, wherein each variable domain is capable of specifically binding to a separate antigen or to a different epitope on the same antigen. Any multispecific antibody format may be adapted for use in the context of an antibody or antigen-binding fragment of an antibody of the present invention using routine techniques available in the art. For example, the present invention includes methods comprising the use of bispecific antibodies wherein one arm of an immunoglobulin is specific for IL-4Rα or a fragment thereof, and the other arm of the immunoglobulin is specific for a second therapeutic target or is conjugated to a therapeutic moiety. Exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [*Epub:* Dec. 4, 2012]).

The antibodies used in the methods of the present invention may be human antibodies. The term "human antibody," as used herein, is intended to include antibodies having variable and constant regions derived from human germline immunoglobulin sequences. The human antibodies of the invention may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The antibodies used in the methods of the present invention may be recombinant human antibodies. The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and V$_L$ regions of the recombinant antibodies are sequences that, while derived from and related to human germline V$_H$ and V$_L$ sequences, may not naturally exist within the human antibody germline repertoire in vivo.

According to certain embodiments, the antibodies used in the methods of the present invention specifically bind IL-4Rα. The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" IL-4Rα, as used in the context of the present invention, includes antibodies that bind IL-4Rα or portion thereof with a K$_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 1 nM, less than about 0.5 nM, less than about 0.25 nM, less than about 0.1 nM or less than about 0.05 nM, as measured in a surface plasmon resonance assay. An isolated antibody that specifically binds human IL-4Rα may, however, have cross-reactivity to other antigens, such as IL-4Rα molecules from other (non-human) species.

According to certain exemplary embodiments of the present invention, the IL-4R inhibitor is an anti-IL-4Rα antibody, or antigen-binding fragment thereof comprising a heavy chain variable region (HCVR), light chain variable region (LCVR), and/or complementarity determining regions (CDRs) comprising any of the amino acid sequences of the anti-IL-4R antibodies as set forth in U.S. Pat. No. 7,608,693. In certain exemplary embodiments, the anti-IL-4Rα antibody or antigen-binding fragment thereof that can be used in the context of the methods of the present invention comprises the heavy chain complementarity determining regions (HCDRs) of a heavy chain variable region (HCVR) comprising the amino acid sequence of SEQ ID NO: 1 and the light chain complementarity determining regions (LCDRs) of a light chain variable region (LCVR) comprising the amino acid sequence of SEQ ID NO: 2. According to certain embodiments, the anti-IL-4Rα antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO: 3; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 6; the LCDR2 comprises the amino acid sequence of SEQ ID NO: 7; and the LCDR3 comprises the amino acid sequence of SEQ ID NO: 8. In some embodiments, the anti-IL-4R antibody or antigen-binding fragment thereof comprises an HCVR comprising SEQ ID NO: 1 and an LCVR comprising SEQ ID NO: 2. According to certain exemplary embodiments, the methods of the present invention comprise the use of the anti-IL-4R antibody comprising HCDR1-HCDR2-HCDR3-LCDR1-LCDR2-LCDR3 amino acid sequences of SEQ ID NOs: 3-4-5-6-7-8, or a bioequivalent thereof. In certain embodiments, the methods of the present invention comprise the use of an anti-IL-4R antibody, wherein the antibody comprises a heavy chain comprising the amino acid sequence of SEQ ID NO: 9. In some embodiments, the anti-IL-4R antibody comprises a light chain comprising the amino acid sequence of SEQ ID NO: 10. An exemplary antibody comprising a heavy chain comprising the amino acid sequence of SEQ ID NO: 9 and a light chain comprising the amino acid sequence of SEQ ID NO: 10 is the fully human anti-IL-4R antibody referred to and known in the art as "dupilumab". According to certain exemplary embodiments, the methods of the present invention comprise the use of dupilumab, or a bioequivalent thereof. The term "bioequivalent", as used herein, refers to anti-IL-4R antibodies or IL-4R-binding proteins or fragments thereof that are pharmaceutical equivalents or pharmaceutical alternatives whose rate and/or extent of absorption do not show a significant difference with that of dupilumab when administered at the same molar dose under similar experimental conditions, either single dose or multiple dose. In the context of the invention, the term refers to antigen-binding proteins that bind to IL-4R which do not have clinically meaningful differences with dupilumab in their safety, purity and/or potency.

Other anti-IL-4Rα antibodies that can be used in the context of the methods of the present invention include, e.g., the antibody referred to and known in the art as AMG317 (Corren et al., 2010, *Am J Respir Crit Care Med.*, 181(8): 788-796), or MEDI 9314, or any of the anti-IL-4Rα antibodies as set forth in U.S. Pat. Nos. 7,186,809, 7,605,237, 7,638,606, 8,092,804, 8,679,487, or U.S. Pat. No. 8,877,189.

The anti-IL-4Rα antibodies used in the context of the methods of the present invention may have pH-dependent binding characteristics. For example, an anti-IL-4Rα antibody for use in the methods of the present invention may exhibit reduced binding to IL-4Rα at acidic pH as compared to neutral pH. Alternatively, an anti-IL-4Rα antibody of the invention may exhibit enhanced binding to its antigen at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding to IL-4Rα at acidic pH as compared to neutral pH" is expressed in terms of a ratio of the K$_D$ value of the antibody binding to IL-4Rα at acidic pH to the K$_D$ value of the antibody binding to IL-4Rα at neutral pH (or vice versa). For example, an antibody or antigen-binding fragment thereof may be regarded as exhibiting "reduced binding to IL-4Rα at acidic pH as compared to neutral pH" for purposes of the present invention if the antibody or antigen-binding fragment thereof exhibits an acidic/neutral K$_D$ ratio of about 3.0 or greater. In certain exemplary embodiments, the acidic/neutral K$_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0, 25.0, 30.0, 40.0, 50.0, 60.0, 70.0, 100.0, or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained. As used herein, the expression "acidic pH" means a pH of 6.0 or less.

Pharmaceutical Compositions

The present invention includes methods which comprise administering an IL-4R inhibitor to a patient, wherein the IL-4R inhibitor is contained within a pharmaceutical composition. The pharmaceutical compositions of the invention are formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient according to the methods of the present invention may vary depending upon the age and the size of the patient, symptoms, conditions, route of administration, and the like. The dose is typically calculated according to body weight or body surface area. Depending on the severity of the condition, the frequency and the duration of the treatment can be adjusted. Effective dosages and schedules for administering pharmaceutical compositions comprising anti-IL-4R antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351). Specific exemplary doses of anti-IL4R antibodies and administration regimens involving the same that can be used in the context of the present invention are disclosed elsewhere herein.

Various delivery systems are known and can be used to administer the pharmaceutical composition comprising an IL-4R inhibitor, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but are not limited to, the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared can be filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Exemplary pharmaceutical compositions comprising an anti-IL-4R antibody that can be used in the context of the present invention are disclosed in, e.g., U.S. Pat. No. 8,945,559.

Administration Regimens

The present invention includes methods comprising administering to a subject an IL-4R inhibitor at a dosing frequency of about four times a week, twice a week, once a week, once every two weeks, once every three weeks, once every four weeks, once every five weeks, once every six weeks, once every eight weeks, once every twelve weeks, or less frequently so long as a therapeutic response is achieved. In certain embodiments involving the administration of an anti-IL-4R antibody, once a week dosing at an amount of about 25 mg, 50 mg, 150 mg, 200 mg, or 300 mg, is employed. In certain embodiments involving the administration of an anti-IL-4R antibody, once in 2 weeks dosing at an amount of about 25 mg, 50 mg, 150 mg, 200 mg, or 300 mg, is employed.

According to certain embodiments of the present invention, multiple doses of an IL-4R inhibitor may be administered to a subject over a defined time course. The methods according to this aspect of the invention comprise sequentially administering to a subject multiple doses of an IL-4R inhibitor. As used herein, "sequentially administering" means that each dose of IL-4R inhibitor is administered to the subject at a different point in time, e.g., on different days separated by a predetermined interval (e.g., hours, days, weeks or months). The present invention includes methods which comprise sequentially administering to the patient a single initial dose of an IL-4R inhibitor, followed by one or more secondary doses of the IL-4R inhibitor, and optionally followed by one or more tertiary doses of the IL-4R inhibitor.

The terms "initial dose," "secondary doses," and "tertiary doses," refer to the temporal sequence of administration of the IL-4R inhibitor. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of IL-4R inhibitor, but generally may differ from one another in terms of frequency of administration. In certain embodiments, however, the amount of IL-4R inhibitor contained in the initial, secondary and/or tertiary doses varies from one another (e.g., adjusted up or down as appropriate) during the course of treatment. In certain embodiments, the initial dose comprises a first amount of the antibody or antigen-binding fragment thereof and the one or more secondary doses each comprise a second amount of the antibody or antigen-binding fragment thereof. In some embodiments, the first amount of antibody or fragment thereof is 1.5×, 2×, 2.5×, 3×, 3.5×, 4×, or 5× the second amount of the antibody or antigen-binding fragment thereof. In certain embodiments, one or more (e.g., 1, 2, 3, 4, or 5) doses are administered at the beginning of the treatment regimen as "loading doses" followed by subsequent doses that are administered on a less frequent basis (e.g., "maintenance doses"). For example, an IL-4R inhibitor may be administered to a patient in need thereof at a loading dose of about 300 mg or about 600 mg followed by one or more maintenance doses of about 25 mg to about 400 mg. In one embodiment, the initial dose and the one or more secondary doses each include 10 mg to 600 mg of the IL-4R inhibitor, e.g., 100 mg to 400 mg of the IL-4R inhibitor, e.g., 10 mg, 25 mg, 50 mg, 100 mg, 150 mg, 200 mg, 250 mg, 300 mg, 400 mg or 500 mg of the IL-4R inhibitor.

In one exemplary embodiment of the present invention, each secondary and/or tertiary dose is administered 1 to 14 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, or more) weeks after the immediately preceding dose. The phrase "the immediately preceding dose," as used herein, means, in a sequence of multiple administrations, the dose of IL-4R inhibitor which is administered to a patient prior to the administration of the very next dose in the sequence with no intervening doses.

The methods according to this aspect of the invention may comprise administering to a patient any number of secondary and/or tertiary doses of an IL-4R inhibitor. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 6 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the regimen.

The methods of the present invention, according to certain embodiments, comprise administering to the subject a topical corticosteroid (TCS) in combination with an IL-4R inhibitor (e.g., an anti-IL-4R antibody). As used herein, the expression "in combination with" means that the TCS is administered before, after, or concurrent with the IL-4R inhibitor. The term "in combination with" also includes sequential or concomitant administration of IL-4R inhibitor and TCS.

For example, when administered "before" the IL-4R inhibitor, the TCS may be administered more than 72 hours, about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes or about 10 minutes prior to the administration of the IL-4R inhibitor. When administered "after" the IL-4R inhibitor, the TCS may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours, about 72 hours, or more than 72 hours after the administration of the IL-4R inhibitor. Administration "concurrent" with the IL-4R inhibitor means that the TCS is administered to the subject in a separate dosage form within less than 5 minutes (before, after, or at the same time) of administration of the IL-4R inhibitor, or administered to the subject as a single combined dosage formulation comprising both the TCS and the IL-4R inhibitor.

Dosage

The amount of IL-4R inhibitor (e.g., anti-IL-4R antibody) administered to a subject according to the methods of the present invention is, generally, a therapeutically effective amount. As used herein, the phrase "therapeutically effective amount" means an amount of IL-4R inhibitor that results in one or more of: (a) an improvement in one or more AD-associated parameters (as mentioned elsewhere herein); and/or (b) a detectable improvement in one or more symptoms or indicia of atopic dermatitis. In the context of the invention, a "therapeutically effective amount" includes an amount of IL-4R inhibitor that results in one or more of: (a) at least 70% decrease from baseline in EASI; (b) reduction in pruritus by at least 30%; (c) a decrease from the baseline of points in IGA; (d) a decrease from the baseline of ≥4 points in NRS; (e) a decrease in skin colonization of Staphylococcus aureus; (f) a reduction in the level of an AD-associated biomarker such as IgE or TARC; (g) reduction in the use of TCS by at least 20%; and/or (h) a reduction in the number of flares or AD exacerbations.

In the case of an anti-IL-4R antibody, an immunologically effective amount can be from about 0.05 mg to about 600 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-IL-4R antibody. In certain embodiments, 10 mg, 25 mg, 50 mg, 75 mg, 150 mg, or 300 mg of an anti-IL-4R antibody is administered to a subject.

The amount of IL-4R inhibitor contained within the individual doses may be expressed in terms of milligrams of antibody per kilogram of subject body weight (i.e., mg/kg). For example, the IL-4R inhibitor may be administered to a subject at a dose of about 0.0001 to about 100 mg/kg of subject body weight.

SELECTED EMBODIMENTS

In Embodiment 1, the present invention includes a method of treating severe atopic dermatitis (AD), the method comprising: (a) selecting a patient with severe AD, wherein the patient is resistant, inadequately responsive or intolerant to systemic immunosuppressant therapy and/or when said therapy is inadvisable; and (b) administering one or more doses of an interleukin 4 receptor (IL-4R) inhibitor to the patient in need thereof.

In Embodiment 2, the present invention includes the method of embodiment 1, wherein the therapy is inadvisable due to safety and health risks to the patient coupled with suboptimal efficacy.

In Embodiment 3, the present invention includes the method of embodiment 1 or 2, wherein the systemic immunosuppressant is selected from the group consisting of cyclosporine A, methotrexate, mycophenolate mofetil, azathioprine, systemic corticosteroids, and interferon-gamma.

In Embodiment 4, the present invention includes the method of embodiment 3, wherein the systemic immunosuppressant is cyclosporine A (CSA).

In Embodiment 5, the present invention includes the method of embodiment 4, wherein the patient has no prior exposure to CSA and CSA therapy is inadvisable due to a condition selected from the group consisting of medical contraindications, hypersensitivity to CSA or excipients, use of a concomitant medication prohibited with CSA, increased susceptibility to CSA-induced renal damage, increased susceptibility to CSA-induced liver damage, and increased risk of serious infections.

In Embodiment 6, the present invention includes the method of embodiment 4, wherein the patient is previously exposed to CSA and CSA therapy is inadvisable due to a condition selected from the group consisting of intolerance, unacceptable toxicity, inadequate response, requirement for CSA at a dose >5 mg/kg/day of the patient's body weight, and requirement of CSA administration for a duration >1 year.

In Embodiment 7, the present invention includes the method of any one of embodiments 1-3, wherein the patient has been previously treated with a therapeutic agent selected from the group consisting of cyclosporine A, an IgE inhibitor, a TNFalpha inhibitor, a CD11a inhibitor, a CD20 inhibitor, an antibiotic, a topical corticosteroid, an oral corticosteroid, a calcineurin inhibitor and phototherapy.

In Embodiment 8, the present invention includes a method of treating or reducing pruritus comprising: (a) selecting a patient with severe AD wherein the patient is resistant, inadequately responsive or intolerant to systemic immunosuppressant therapy; and (b) administering one or more doses of an IL-4R inhibitor to the patient in need thereof.

In Embodiment 9, the present invention includes the method of embodiment 8, wherein the systemic immunosuppressant is selected from the group consisting of cyclosporine A, methotrexate, mycophenolate mofetil, azathioprine, systemic corticosteroids, and interferon-gamma.

In Embodiment 10, the present invention includes the method of embodiment 8 or 9, wherein the systemic immunosuppressant is cyclosporine A (CSA).

In Embodiment 11, the present invention includes the method of any one of embodiments 8-10, wherein the patient has severe AD.

In Embodiment 12, the present invention includes the method of any one of embodiments 8-11, wherein administration of the IL-4R inhibitor leads to reduction from the baseline of at least 30% in pruritus in the patient.

In Embodiment 13, the present invention includes a method of treating severe AD, the method comprising: (a) selecting a patient with severe AD, wherein the patient has been previously treated with a therapeutic selected from the group consisting of cyclosporine A, an IgE inhibitor, a TNFalpha inhibitor, a CD11a inhibitor, a CD20 inhibitor, an antibiotic, an IL-4R inhibitor, dupilumab, a systemic immunosuppressant, a topical corticosteroid, an oral corticosteroid, a calcineurin inhibitor and phototherapy; and (b) administering one or more doses of an IL-4R inhibitor to the patient in need thereof.

In Embodiment 14, the present invention includes the method of embodiment 13, wherein the patient is resistant, inadequately responsive or intolerant to the therapeutic.

In Embodiment 15, the present invention includes the method of embodiment 13 or 14, wherein the therapy is inadvisable due to safety and health risks to the patient coupled with suboptimal efficacy.

In Embodiment 16, the present invention includes the method of any one of embodiments 1-15, wherein the one or more doses comprise 50-600 mg of the IL-4R inhibitor.

In Embodiment 17, the present invention includes the method of any one of embodiments 1-15, wherein the one or more doses comprise 300 mg of the IL-4R inhibitor.

In Embodiment 18, the present invention includes the method of embodiment 16 or 17, wherein one or more doses of the IL-4R inhibitor are administered once a week, once in 2 weeks, once in 3 weeks, or once in 4 weeks.

In Embodiment 19, the present invention includes the method of any one of embodiments 1-15, wherein the IL-4R inhibitor is administered at an initial dose followed by one or more secondary doses.

In Embodiment 20, the present invention includes the method of embodiment 19, wherein the initial dose comprises 50-600 mg of the IL-4R inhibitor and each secondary dose comprises 25-400 mg of the IL-4R inhibitor.

In Embodiment 21, the present invention includes the method of embodiment 20, wherein the initial dose comprises 600 mg of the IL-4R inhibitor and each secondary dose comprises 300 mg of the IL-4R inhibitor.

In Embodiment 22, the present invention includes the method of embodiment 19 or 20, wherein each secondary dose is administered one week after the immediately preceding dose.

In Embodiment 23, the present invention includes the method of embodiment 19 or 20, wherein each secondary dose is administered 2 weeks after the immediately preceding dose.

In Embodiment 24, the present invention includes the method of any of any one of embodiments 1-23, wherein administration of the IL-4R inhibitor results in an improvement in at least one AD-related parameter selected from the group consisting of: (a) a decrease from baseline in Eczema Area and Severity Index (EASI) score of at least 75%; (b) a decrease from baseline in Pruritus Numeric Rating Scale (NRS) score of at least 30%; (c) a decrease from baseline in Body Surface Area Involvement of Atopic Dermatitis (BSA) score of at least 25%; (d) a decrease from baseline in Investigator's Global Assessment (IGA) score of points; and (e) a decrease from baseline in NRS score of ≥3 points.

In Embodiment 25, the present invention includes the method of any of any one of embodiments 1-24, wherein administration of the IL-4R inhibitor results in an improvement in at least one patient related outcome selected from the group consisting of Global Individual Signs Score (GISS), Patient Oriented Eczema Measure (POEM), Patient-assessed Hospital Anxiety and Depression Scale (HADS) and Patient-reported Dermatology Life Quality Index (DLQI).

In Embodiment 26, the present invention includes the method of any one of embodiments 1-25, wherein administration of the IL-4R inhibitor results in a decrease in the number of flares or exacerbations in the patient.

In Embodiment 27, the present invention includes the method of any of any one of embodiments 1-26, wherein the IL-4R inhibitor is administered subcutaneously.

In Embodiment 28, the present invention includes the method of any one of embodiments 1-27, wherein the IL-4R inhibitor is administered concomitantly with a second therapeutic agent.

In Embodiment 29, the present invention includes the method of embodiment 28, wherein the second therapeutic agent is selected from the group consisting of topical corticosteroids, calcineurin inhibitors, and emollients.

In Embodiment 30, the present invention includes the method of embodiment 29, wherein the topical corticosteroid is selected from the group consisting of low-potency TCS, medium-potency TCS and high-potency TCS.

In Embodiment 31, the present invention includes the method of embodiment 30, wherein the amount of topical corticosteroids used by the patient is gradually reduced following administration of the first dose of the IL-4R inhibitor.

In Embodiment 32, the present invention includes the method of embodiment 31, wherein the amount of topical corticosteroids used by the patient is reduced by least about 20% in 4 weeks following administration of the first dose of the IL-4R inhibitor.

In Embodiment 33, the present invention includes the method of embodiment 31 or 32, wherein the amount of topical corticosteroids used by the patient is reduced by about 50% in 4 weeks following administration of the first dose of the IL-4R inhibitor.

In Embodiment 34, the present invention includes the method of any one of embodiments 1-33, wherein the IL-4R inhibitor is an antibody or antigen-binding fragment thereof that binds IL-4Rα and prevents the interaction of IL-4 and/or IL-13 with a type 1 or type 2 IL-4 receptor.

In Embodiment 35, the present invention includes the method of embodiment 34, wherein the antibody or antigen-binding fragment thereof prevents the interaction of IL-4 and IL-13 with both type 1 and type 2 IL-4 receptors.

In Embodiment 36, the present invention includes the method of embodiment 34 or 35, wherein the antibody or antigen-binding fragment thereof comprises the heavy chain complementarity determining regions (HCDRs) of a heavy chain variable region (HCVR) comprising the amino acid sequence of SEQ ID NO: 1 and the light chain complementarity determining regions (LCDRs) of a light chain variable region (LCVR) comprising the amino acid sequence of SEQ ID NO: 2.

In Embodiment 37, the present invention includes the method of embodiment 34 or 35, wherein the antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO: 3; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 6; the LCDR2 comprises the amino acid sequence of SEQ ID NO: 7; and the LCDR3 comprises the amino acid sequence of SEQ ID NO: 8.

In Embodiment 38, the present invention includes the method of embodiment 37, wherein the HCVR comprises the amino acid sequence of SEQ ID NO: 1 and the LCVR comprises the amino acid sequence of SEQ ID NO: 2.

In Embodiment 39, the present invention includes the method of embodiment 36 or 37, wherein the antibody or antigen-binding fragment thereof comprises a heavy chain comprising the amino acid sequence of SEQ ID NO: 9 and a light chain comprising the amino acid sequence of SEQ ID NO: 10.

In Embodiment 40, the present invention includes the method of any one of embodiments 1-38, wherein the IL-4R inhibitor is dupilumab or a bioequivalent thereof.

In Embodiment 41, the present invention includes the method of embodiment 34, wherein the antibody or antigen-binding fragment thereof is MED19314 or AMG317.

In Embodiment 42, the present invention includes a method for treating moderate-to-severe or severe atopic dermatitis (AD) or improving an AD-associated parameter, the method comprising: (a) selecting a patient with moderate-to-severe or severe AD wherein the patient has an attribute selected from the group consisting of: (i) the patient has a baseline IGA score=4; (ii) the patient has a baseline IGA score ≥3; (iii) the patient is between 6 and 18 years of age; (iv) the patient has disease that is uncontrolled by topical AD therapy; (v) the patient has a documented history of inadequate response to topical AD therapy or for whom topical therapy is inadvisable due to adverse side effects or safety risks; (vi) the patient has been previously treated with a medication or procedure selected from the group consisting of a topical corticosteroid, a topical calcineurin inhibitor, an anti-histamine, an emollient, a dermatological therapeutic, a systemic glucocorticoid, a non-steroidal systemic immunosuppressant, cyclosporine A, azathioprine, UV light therapy, and phototherapy; and (vii) the patient has a concomitant disease or disorder selected from the group consisting of food allergy, asthma, seasonal allergy, allergic rhinitis, house dust allergy, and allergic conjunctivitis; and (b) administering one or more doses of a therapeutically effective amount of an IL-4R inhibitor to the patient in need thereof.

In Embodiment 43, the present invention includes the method of embodiment 42, wherein the patient has severe AD, is between 6 and 11 years of age, has a baseline IGA score=4, and has disease that is uncontrolled by topical therapy.

In Embodiment 44, the present invention includes the method of embodiment 42 or 43, wherein the IL-4R inhibitor is an anti-IL-4R antibody of any one of embodiments 34-41.

In Embodiment 45, the present invention includes the method of any one of embodiments 42-44, wherein each dose of the IL-4R inhibitor comprises 1, 2, 3, 4 or 5 mg/kg of the patient's body weight, and wherein each dose is administered 1-4 weeks after the immediately preceding dose.

In Embodiment 46, the present invention includes the method of any one of embodiments 42-44, wherein each dose comprises 20-600 mg of the IL-4R inhibitor, and wherein each dose is administered 1-4 weeks after the immediately preceding dose.

In Embodiment 47, the present invention includes the method of any one of embodiments 42-46, wherein the administration of the IL-4R inhibitor leads to an effect selected from the group consisting of: (i) more than 30% reduction from baseline in EASI score by week 2 after administration of the first dose of the IL-4R inhibitor; (ii) more than 50% reduction from baseline in pruritus NRS; and (iii) a reduction from baseline in IGA score to achieve an IGA score of 0 or 1 by week 12 after administration of the first dose of the IL-4R inhibitor.

In Embodiment 48, the present invention includes the method of any one of embodiments 42-47, wherein the IL-4R inhibitor is administered in combination with a second therapeutic agent selected from the group consisting of a topical corticosteroid, a topical calcineurin inhibitor, an anti-histamine, an emollient, an anti-bacterial therapeutic, and a therapeutic agent for obstructive airway disease.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Clinical Trial of Anti-IL-4R Antibody in Adult Patients with Severe Atopic Dermatitis (AD) Who are not Adequately Controlled with or are Intolerant to Cyclosporine A, or when this Treatment is not Medically Advisable This is a 32-week double-blind, randomized, placebo-controlled, parallel group study to confirm the efficacy, safety and tolerability of dupilumab administered in adults with severe AD for whom cyclosporine A (CSA) has either not demonstrated adequate efficacy, had unacceptable side effects, or for whom initiating CSA is not medically advisable.

Dupilumab is a fully human anti-IL-4R antibody comprising a heavy chain comprising the amino acid sequence of SEQ ID NO: 9 and a light chain comprising the amino acid sequence of SEQ ID NO: 10; an HCVR/LCVR amino acid sequence pair comprising SEQ ID NOs: 1/2; and heavy and light chain CDR sequences comprising SEQ ID NOs: 3-8.

The study comprises a 2-week screening period, a 2-week medium-potency TCS standardization period, a 16-week treatment period, and a 12-week safety follow up period. This study is done to evaluate dupilumab treatment in these patients, who have also previously demonstrated inadequate response to TCS. All patients receive concomitant medium-potency TCS as background concomitant therapy to reflect standard of care treatment of this severe population.

Study Objectives

The primary objective of the study is to evaluate the efficacy of 2 dose regimens of dupilumab compared to placebo, administered with concomitant topical corticosteroids (TCS), in adult patients with severe AD who are not adequately controlled with, or are intolerant to, oral CSA, or when this treatment is currently not medically advisable.

The secondary objective of the study is to assess the safety and tolerability of 2 dose regimens of dupilumab compared to placebo, administered with concomitant TCS, in adult patients with severe AD who are not adequately controlled with, or are intolerant to, oral CSA, or when this treatment is currently not medically advisable.

Study Design

The study comprises a 2-week screening period, a 2-week medium-potency TCS standardization period, a 16-week treatment period, and a 12-week safety follow up period. This study is done to evaluate dupilumab treatment in these patients with severe AD who have also previously demonstrated inadequate response to TCS. All patients receive concomitant medium-potency TCS as background concomitant therapy to reflect standard of care treatment of this severe population.

After providing informed consent, patients are assessed for study eligibility at the screening visit. Patients undergo screening between day −28 and day −15, prior to randomization. During this 2-week screening period, TCS treatment is allowed at the discretion of the investigator.

Starting on day −14, all patients initiate a standardized TCS treatment regimen, and continue the standardized medium-potency regimen through the end of the treatment period (week 16). During the 12-week follow-up period, they may continue to receive TCS at the discretion of the investigator, for intolerable AD disease activity.

Patients are also required to apply moisturizers at least twice daily for at least the 7 consecutive days immediately before randomization (baseline/day 1) and continue at least twice daily throughout the study.

Patients who continue to meet eligibility criteria at baseline (day 1) undergo assessments and are randomized in a 1:1:1 ratio to receive either once-weekly (qw) or every 2 week (q2w) subcutaneous (SC) injections of 300 mg dupilumab (following an SC loading dose of 600 mg on day 1), or matching injectable placebo, including the placebo for the loading dose. During weeks in which dupilumab is not administered (in the q2w regimen), patients receive injectable placebo. In order to maintain blinding, all patients receive an injection (active or placebo) each week from day 1 to week 16 (treatment period).

The patients are stratified by: 1) Baseline assessment of disease severity (Investigator's Global Assessment [IGA] 3 vs IGA 4) and 2) documented history of no prior CSA exposure and not currently a candidate for CSA treatment or CSA prior exposure that should not be continued or restarted.

Patients are followed up for an additional 12 weeks for safety after the end of the treatment period.

Study Population

Adult, male and female patients with severe AD whose disease cannot be adequately controlled with TCS, who are not adequately controlled with, or are intolerant to oral CSA, or when CSA treatment is currently deemed not medically advisable by a physician, according to the following:

(A) No prior CSA exposure (who are not currently a candidate for CSA treatment) due to:
  Medical contraindications;
  Hypersensitivity to CSA active substance or excipients;
  Use of concomitant medications prohibited with CSA; or
  Increased susceptibility to CSA induced renal damage, increased risk of serious infections, etc.
  Or
(B) Previously exposed to CSA and for whom CSA should not be continued or restarted due to:
  Previous intolerance and/or unacceptable toxicity
  Inadequate response—defined as flare of AD on CSA tapering after a maximum of 6 weeks of high dose (5 mg/kg/day) to maintenance dose (2 to 3 mg/kg/day) or a flare after a minimum of 3 months on maintenance dose. Flare is defined as increase in signs and/or symptoms leading to escalation of therapy, which can be an increase in CSA dose, a switch to a higher-potency class of TCS, or the start of another oral immunosuppressive drug; or
  Requirement for CSA at doses or duration beyond that specified in the prescribing information.

Inclusion Criteria:

A patient must meet the following criteria to be eligible for inclusion in the study:

(1) Male or female, 18 years of age or older with severe chronic AD (according to American Academy of Dermatology Consensus Criteria [Eichenfield et al 2014, J. Am. Acad. Dermatol. 70: 338-351]) for whom treatment with potent TCS is indicated;

(2) Eczema Area Severity Index (EASI) score ≥20 at the screening and baseline visits (Leshem et al 2015, doi: 10.1111/bjd.13662 [epub ahead of print]). A single reassessment of the EASI score is allowed within 48 hours of the initial screening, if the EASI score at the initial screening visit is either 18 or 19;

(3) IGA score ≥3 (on the 0 to 4 IGA scale) at the screening and baseline visits;

(4) ≥10% body surface area (BSA) of AD involvement at the screening and baseline visits;

(5) Documented history by a physician of either:
  (A) No Prior CSA Exposure and not Currently a Candidate for CSA Treatment Due to:
    medical contraindications (e.g., uncontrolled hypertension on medication), or
    use of prohibited concomitant medications (e.g., statins, digoxin, macrolide antibiotics, barbiturates, anti-seizure, nonsteroidal anti-inflammatory drugs, diuretics, angiotensin-converting-enzyme inhibitors, St John's Wort, etc.), or
    increased susceptibility to CSA-induced renal damage (elevated creatinine) and liver damage (elevated function tests), or
    increased risk of serious infections, or
    hypersensitivity to CSA active substance or excipients, or
  (B) Previously Exposed to CSA, and CSA Treatment should not be Continued or Restarted Due to:
    intolerance and/or unacceptable toxicity (e.g., elevated creatinine, elevated liver function tests, uncontrolled hypertension, paraesthesia, headache, nausea, hypertrichosis, etc.), or
    inadequate response to CSA (defined as flare of AD on CSA tapering after a maximum of 6 weeks of high dose [5 mg/kg/day] to maintenance dose [2 to 3 mg/kg/day] or a flare after a minimum of 3 months on maintenance dose). Flare is defined as increase in signs and/or symptoms leading to escalation of therapy, which can be an increase in dose, a switch to a higher-potency class of TCS, or the start of another systemic non-steroidal immunosuppressive drug; or
    requirement for CSA at doses >5 mg/kg/day, or duration beyond those specified in the prescribing information (>1 year);

(6) Documented recent history (within 6 months before the screening visit) of inadequate response to treatment with TCS.
  NOTE: Inadequate response is defined as failure to achieve and maintain remission or a low disease activity state (comparable to IGA 0=clear to 2=mild) despite treatment with a daily regimen of TCS of medium to higher-potency (±TCI as appropriate), applied for at least 28 days or for the maximum duration recommended by the product prescribing information (e.g., 14 days for super-potent TCS), whichever is shorter;

(7) Have applied a stable dose of topical emollient (moisturizer) twice daily for at least 7 consecutive days immediately before the baseline visit;

(8) Willing and able to comply with clinic visits and study-related procedures;

(9) Provide signed informed consent; and (10) Able to understand and complete study-related questionnaires.

Exclusion Criteria:

A patient who meets any of the following criteria is excluded from the study: (1) Participation in a prior dupilumab clinical study; (2) Treatment with an investigational drug within 8 weeks or within 5 half-lives (if known), whichever is longer, prior to screening; (3) Hypersensitivity and/or intolerance to corticosteroids or to any other ingredients contained in the TCS product used in the study; (4) Systemic CSA, systemic corticosteroids, or phototherapy within 4 weeks prior to screening, and azathioprine (AZA), methotrexate (MTX), mycophenolate mofetil (MMF), or Janus kinase (JAK) inhibitors within 8 weeks prior to screening; (5) Treatment with a TCI within 1 week prior to the screening visit; (6) Treatment with biologics as follows: (a) Any cell-depleting agents including but not limited to rituximab: within 6 months before the screening visit, or until lymphocyte count returns to normal, whichever is longer; (b) Other biologics: within 5 half-lives (if known) or 16 weeks prior to the screening visit, whichever is longer; (7) At the baseline visit, 30% of the total lesional surface located on areas of thin skin that cannot be safely treated with medium-potency TCS (e.g., face, neck, intertriginous areas, genital areas, areas of skin atrophy); (8) Initiation of treatment of AD with prescription moisturizers or moisturizers containing additives such as ceramide, hyaluronic acid, urea, or filaggrin degradation products during the screening period (patients may continue using stable doses of such moisturizers if initiated before the screening visit); (9) Regular use (more than 2 visits per week) of a tanning booth/parlor within 4 weeks of the screening visit; (10) Planned or anticipated use of any prohibited medications and procedures during study treatment; (11) Treatment with a live (attenuated) vaccine within 12 weeks before the screening visit; (12) Active chronic or acute infection requiring treatment with systemic antibiotics, antivirals, antiparasitics, antiprotozoals, or antifungals within 2 weeks before the screening visit, or superficial skin infections within 1 week before the screening visit. NOTE: Patients may be rescreened no sooner than 2 weeks after the infection resolves, and with permission of the sponsor's medical monitor; (13) Known or suspected history of immunosuppression, including history of invasive opportunistic infections (e.g., tuberculosis [TB], histoplasmosis, Listeriosis, coccidioidomycosis, pneumocystosis, aspergillosis) despite infection resolution; or unusually frequent, recurrent, or prolonged infections, per investigator judgment; (14) Presence of any 1 of the following TB criteria: (a) A positive tuberculin skin test at the screening visit; (b) A positive blood QuantiFERON®-TB or T-Spot test at the screening visit; or (c) Chest x-ray (posterior-anterior and lateral views) at screening or within 3 months before the screening visit (radiology report must be available) with results consistent with prior TB infection (including but not limited to apical scarring, apical fibrosis, or multiple calcified granuloma). This does not include non-caseating granulomata. NOTE: Any of these 3 TB tests will be performed on a country-by-country basis according to local guidelines only if required by regulatory authorities or ethics boards; (15) History of human immunodeficiency virus (HIV) infection or positive HIV serology at screening; (16) Positive hepatitis B surface antigen (HBsAg), hepatitis B core antibody (HBcAb), or hepatitis C antibody (HCV Ab) at the screening visit; (17) At baseline, presence of any conditions listed as criteria for study drug discontinuation; (18) Presence of skin characteristics that may interfere with study assessments; (19) History of malignancy within 5 years before the screening visit, except completely treated in situ carcinoma of the cervix, completely treated and resolved non-metastatic squamous or basal cell carcinoma of the skin; (20) Diagnosed active endoparasitic infections; suspected or high risk of endoparasitic infection, unless clinical and (if necessary) laboratory assessment have ruled out active infection before randomization; (21) History of alcohol or drug abuse within 2 years of the screening visit; (22) Severe concomitant illness(es) that, in the investigator's judgment, would adversely affect the patient's participation in the study. Examples include, but are not limited to, patients with short life expectancy, patients with uncontrolled diabetes (hemoglobin A1c [HbA1c]≥9%), patients with cardiovascular conditions (e.g., stage III or IV cardiac failure according to the New York Heart Association classification), severe renal conditions (e.g., patients on dialysis), hepato-biliary conditions (e.g., Child-Pugh class B or C), neurological conditions (e.g., demyelinating diseases), active major autoimmune diseases (e.g., lupus, inflammatory bowel disease, rheumatoid arthritis, etc.), neuro-inflammatory disease, other severe endocrinological, gastrointestinal, metabolic, pulmonary or lymphatic diseases. The specific justification for patients excluded under this criterion will be noted in study documents (chart notes, case report forms [CRFs], etc.); (23) Any other medical or psychological condition (including relevant laboratory abnormalities at screening) that, in the opinion of the investigator, may suggest a new and/or insufficiently understood disease, may present an unreasonable risk to the study patient as a result of his/her participation in this clinical trial, may make patient's participation unreliable, or may interfere with study assessments. The specific justification for patients excluded under this criterion will be noted in study documents (chart notes, CRFs, etc.); (24) Planned or anticipated major surgical procedure during the patient's participation in this study; (25) Patient is a member of the investigational team or his/her immediate family; (26) Pregnant or breast-feeding women, or women planning to become pregnant or breast-feed during the study; and (27) Women unwilling to use adequate birth control, if of reproductive potential and sexually active.

Study Treatments

Study Drug:

Patients receive either qw SC injections of 300 mg dupilumab (following a loading dose of 600 mg on day 1), or q2w SC injections of 300 mg dupilumab (following a loading dose of 600 mg on day 1) during the 16-week treatment period. During weeks in which dupilumab is not administered (in the q2w regimen), patients receive injectable placebo.

Placebo:

Patients receive weekly injections of matching placebo (following a placebo "loading dose" on day 1) during the 16-week treatment period.

Background Treatment

Topical Corticosteroids:

Starting on day −14, all patients are required to undergo treatment with TCS using a standardized regimen according to the following guidelines:

Apply medium-potency TCS once daily to areas with active lesions
  Low-potency TCS should be used once daily on areas of thin skin (face, neck, intertriginous, and genital areas, areas of skin atrophy, etc.) or for areas where continued treatment with medium-potency TCS is considered unsafe Monitor the patient for signs of local or systemic TCS toxicity and stop treatment as necessary It is recommended that patients use triamcinolone acetonide 0.1% cream or fluocinolone acetonide 0.025% ointment for medium-potency, and hydrocortisone 1% cream for low-potency. If patients have tolerance issues with any of these steroids or if they are not commercially available in some countries, they may substitute with products of the same potency from the list provided in the study reference manual. On areas treated with TCS, moisturizers should be applied once daily only at the time when TCS is not applied (i.e., do not use moisturizers and TCS on the same areas at the same time during the day). For example, if TCS are applied in the evening, moisturizers are not to be used in the evening on areas treated with TCS, but are applied to those areas in the morning. On areas not treated with TCS, moisturizers will be applied twice daily—morning and evening.

The type, amount, frequency, and potency of topical products used during the study is recorded at home by patients in a medication diary. Patients return TCS tubes at each clinic visit up until week 16, and these tubes are weighed by the site staff to determine the actual amount of TCS used. During the 12-week safety follow-up period, the weighing of tubes is no longer needed.

During the 16-week placebo-controlled study treatment period, medium-potency TCS dosing frequency will be symptom-based (IGA score) adjusted every 4 weeks as per the following protocol-specified tapering algorithm:

At day 29 (week 4): * If a patient on daily (qd) dosing achieves an IGA of 0 they will be switched to every-other-day (qod) dosing until day 57 (week 8); * If a patient on qd dosing does not achieve an IGA of 0 they will remain on qd dosing until day 57 (week 8)

At day 57 (week 8): * If a patient on qd dosing achieves an IGA of 0 they are switched to qod dosing until day 85 (week 12); * If a patient on qd dosing does not achieve an IGA of 0 they remain on qd dosing until day 85 (week 12); * If a patient on qod dosing remains an IGA 0 they are switched to twice-a-week dosing until day 85 (week 12); * If a patient on qod dosing does not remain an IGA 0 they switch to qd dosing until day 85 (week 12)

At day 85 (week 12): * If a patient on qd dosing does not achieve an IGA 0 they remain on qd dosing until day 113 (week 16); * If a patient on qd dosing achieves an IGA 0 they are switched to qod dosing until day 113 (week 16); * If a patient on qod dosing remains an IGA 0 they are switched to twice-a-week dosing until day 113 (week 16); * If a patient on twice-a-week dosing remains an IGA 0 they remain on twice-a-week dosing until day 113 (week 16); * If a patient on twice-a-week dosing does not remain an IGA 0 they switch to qod dosing until day 113 (week 16)

Emollients:

All patients are required to apply moisturizers (emollients) at least twice daily for at least the 7 consecutive days immediately before randomization (baseline/day 1) and to continue throughout the study (all 32 weeks). However, to allow adequate assessment of skin dryness, moisturizers should not be applied on the area(s) of non-lesional skin designated for such assessments for at least 8 hours before each clinic visit. All types of moisturizers are permitted, but patients may not initiate treatment with prescription moisturizers or moisturizers containing additives during the screening period or during the study. Patients may continue using stable doses of prescription moisturizers or moisturizers containing additives, if initiated before the screening visit.

Rescue Treatment

If medically necessary (i.e., to control intolerable AD symptoms), rescue treatment for AD may be provided to study patients, starting with high-potency TCS and if needed, escalation to systemic medications for patients who do not respond adequately after at least 7 days of topical treatment.

Study Endpoints

The primary endpoint in the study is: the proportion of patients with Eczema Area and Severity Index (EASI) 75 (≥75% improvement from baseline) at week 16.

The secondary endpoints are:

Efficacy:
• Proportion of patients with EASI 75 (75% improvement from baseline) at week 16 for patients with prior CSA use; • Proportion of patients with IGA 0 or 1 (on a 5-point scale) and a reduction from baseline of points at week 16; • Percent change from baseline to week 16 in the pruritus numerical rating scale (NRS); • Proportion of patients with improvement (reduction) of pruritus NRS at week 16; • Percent change from baseline to week 16 in the EASI score; • Change from baseline to week 16 in percent body surface area (BSA); • Percent change from baseline to week 16 in the SCORing Atopic Dermatitis (SCORAD); • Proportion of patients with SCORAD 50 (≥50% improvement from baseline) at week 16; • Percent change from baseline to week 16 in the Global Individual Signs Score (GISS) (erythema, infiltration/papulation, excoriations, lichenification); • Change from baseline to week 16 in the Dermatology Life Quality Index (DLQI); • Change from baseline to week 16 in the Patient Oriented Eczema Measure (POEM); • Change from baseline to week 16 in the Hospital Anxiety and Depression Scale (HADS); • Percent change from baseline to week 2 in the pruritus NRS; • Mean weekly dose of TCS through week 16

Safety and Tolerability:
• Incidence of skin infection treatment-emergent adverse events (TEAEs) requiring systemic treatment from baseline through the on-treatment period; • Incidence of treatment-emergent serious adverse events (TESAEs) from baseline through the on-treatment period; • Incidence of TEAEs leading to treatment discontinuation from baseline through the on-treatment period; • Overall incidence of TEAEs from baseline through the on-treatment period Procedures and Assessments Overall safety is assessed by monitoring/evaluation of TEAEs, vital signs, physical examinations, electrocardiograms (ECGs), and clinical safety laboratory tests.

Other measures include pharmacokinetic (PK) assessments, the potential emergence of anti-drug antibodies (ADA) to dupilumab, and research testing.

Efficacy Procedures

A variety of parameters are collected during the study to assess efficacy/effectiveness of dupilumab including measures of AD severity, use of concomitant treatment for AD, and patient reported measures of AD symptoms and QOL. Efficacy is assessed using pruritus NRS, pruritus categorical scale, POEM, HADS, DLQI, the European Quality of Life-5 Dimensions (EQ-5D), Patient Global Assessment of Disease, Patient Global Assessment of Treatment, Asthma Control Questionnaire (ACQ-5), the Sino-Nasal Outcome Test (SNOT-22), assessment of sick leave/missed school days, IGA, EASI, BSA of involvement of AD, GISS and SCORAD.

Pruritus NRS, pruritus categorical scale, POEM, HADS, DLQI, the European Quality of Life-5 Dimensions (EQ-5D), Patient Global Assessment of Disease, Patient Global Assessment of Treatment, IGA, EASI, BSA of involvement of AD, GISS and SCORAD have been described in US Patent Application Publication 20140072583, incorporated herein in its entirety.

Juniper Asthma Control Questionnaire: The 5-question version of the Juniper ACQ is a validated questionnaire to evaluate asthma control. The questionnaire is administered only to the subset of patients with a medical history of asthma and who fluently speak a language in which the questionnaire is presented (based on availability of validated translations in participating countries).

Sinonasal Outcome Test: The SNOT-22 is a validated questionnaire to assess the impact of chronic rhinosinusitis on QOL. The questionnaire is administered only to the subset of patients with chronic inflammatory conditions of the nasal mucosa and/or paranasal sinuses (e.g., chronic rhinitis/rhinosinusitis, nasal polyps, allergic rhinitis) who fluently speak a language in which the questionnaire is presented.

Assess Sick Leave/Missed School Days: Patients who are employed or enrolled in school are asked to report the number of sick leave/missed school days since the last study assessment.

Global Individual Signs Score: Individual components of the AD lesions (erythema, infiltration/papulation, excoriations, and lichenification) are rated globally (i.e., each assessed for the whole body, not by anatomical region) on a 4-point scale (from 0=none to 3=severe) using the EASI severity grading criteria.

Exploratory Biomarker Testing

Biomarkers to be analyzed in this study are TARC and serum total IgE. These are exploratory assessments to further the understanding of AD-associated biomarkers and the response to dupilumab treatment. Thymus and activation regulated chemokine and total IgE are markers of Th2 activity and are downstream of IL-4/13 signaling. These analytes are assessed as measures of Th2 activity and pharmacodynamic effect of the drug. These results may also be used for modeling dupilumab activity with drug levels. Thymus and activation regulated chemokine levels have also been closely associated with AD disease activity and severity, and will be evaluated as an exploratory marker of efficacy. These markers may also be assessed for their potential value in predicting treatment response.

Safety Assessment

Safety is assessed throughout the study by monitoring Adverse Events and Serious Adverse Events.

An Adverse Event (AE) is any untoward medical occurrence in a subject or clinical investigation subject administered a pharmaceutical product. An AE can, therefore, be any unfavorable and unintended sign (including abnormal laboratory finding), symptom, or disease temporally associated with the use of a medicinal product, whether or not considered related to the medicinal (investigational) product. AEs also include: any worsening (i.e., any clinically significant change in frequency and/or intensity) of a pre-existing condition that is temporally associated with the use of the study drug; abnormal laboratory findings considered by the Investigator to be clinically significant; and any untoward medical occurrence.

A Serious Adverse Event (SAE) is any untoward medical occurrence that at any dose results in death; is life-threatening; requires in-patient hospitalization or prolongation of existing hospitalization; results in persistent or significant disability/incapacity; is a congenital anomaly/birth defect; or is an important medical event.

Results

It is expected that at the end of the study period, dupilumab administration will treat AD, including severe and/or refractory AD, in patients with severe AD who are not adequately controlled with, or are intolerant to, oral cyclosporine A, or when this treatment is currently not medically advisable. Patients treated with dupilumab show significant improvement in at least one AD-associated parameter as compared to placebo. Patients treated with dupilumab use up to 50% less TCS than placebo.

The baseline demographic and baseline disease characteristics were similar among the treatment groups (Table 1).

TABLE 1

Baseline demographic and disease characteristics across treatment groups

|  | Placebo + TCS (N = 108) | 300 mg dupilumab q2w + TCS (N = 107) | 300 mg dupilumab qw + TCS (N = 110) |
|---|---|---|---|
| Age, mean ± SD, years | 38.9 (13.35) | 37.5 (12.89) | 38.7 (13.21) |
| Male sex, n (%) | 68 (63.0) | 65 (60.7) | 66 (60.0) |
| Duration of AD (years), mean (SD) | 29.2 (14.72) | 29.6 (15.61) | 32.3 (14.00) |
| EASI score, mean ± SD | 32.9 ± 10.80 | 33.3 ± 9.93 | 33.1 ± 11.02 |
| Patients with IGA = 4$^a$, n (%) | 52 (48.1) | 50 (46.7) | 52 (47.3%) |
| Peak Weekly Averaged Pruritus NRS, mean ± SD | 6.4 ± 2.23 | 6.6 ± 2.10 | 6.2 ± 2.01 |
| BSA, mean ± SD | 55.0 ± 20.51 | 56.1 ± 17.83 | 56.0 ± 19.26 |
| SCORAD score, mean (SD) | 67.0 (12.20) | 68.6 (11.91) | 66.0 (12.70) |
| POEM score, mean ± SD | 19.1 ± 5.99 | 19.3 ± 6.21 | 18.6 (6.97) |
| DLQI score, mean (SD) | 13.2 (7.60) | 14.5 (7.63) | 13.8 (8.03) |

Compared to placebo, both dupilumab dose regimens (300 mg qw+TCS; 300 mg q2w+TCS) demonstrated robust efficacy across multiple clinical outcomes, reflecting improvements in objective signs of AD, pruritus, quality of life and mental health. The primary endpoint at week 16 was achieved for both dupilumab dose regimens. Compared with placebo+TCS, dupilumab q2w+TCS significantly improved patient-reported itch, sleep, skin symptoms, quality of life (QoL) and health status as measured by pruritus Numerical Rating Scale; Scoring Atopic Dermatitis visual analog scale for sleep loss; Patient-Oriented Eczema Measure; and Dermatology Life Quality Index. Table 2 presents the primary and secondary efficacy results for the endpoints in the endpoint hierarchy specified in the SAP.

TABLE 2

Effect of dupilumab on clinical parameters across treatment groups

| Endpoint | Dose Regimen | Placebo + TCS | Dupilumab + TCS |
|---|---|---|---|
| % patients with EASI-75 | 300 mg qw | 29.6% | 59.1% |
|  | 300 mg q2w |  | 62.6% |
| % change in EASI score from baseline to week 16 | 300 mg qw | −46.6 | −78.2 |
|  | 300 mg q2w |  | −79.8 |
| % change in baseline in weekly average of peak daily pruritus NRS | 300 mg qw | −25.4 | −51.7 |
|  | 300 mg q2w |  | −53.9 |
| % change from baseline in SCORAD | 300 mg qw | −29.5 | −62.4 |
|  | 300 mg q2w |  | −58.3 |

TABLE 2-continued

Effect of dupilumab on clinical parameters across treatment groups

| Endpoint | Dose Regimen | Placebo + TCS | Dupilumab + TCS |
|---|---|---|---|
| % patients with reduction of weekly average peak daily pruritus NRS ≥4 from baseline | 300 mg qw<br>300 mg q2w | 14.3% (N = 91) | 40.4% (N = 94)<br>45.7% (N = 94) |
| Change from baseline in % BSA | 300 mg qw<br>300 mg q2w | −19.6 | −37.5<br>−39.2 |
| % patients with IGA 0 or 1 and reduction from baseline of ≥2 points | 300 mg qw<br>300 mg q2w | 13.9% | 39.1%<br>40.2% |
| Change from baseline in DLQI | 300 mg qw<br>300 mg q2w | −4.5 | −8.9<br>−9.6 |
| Change from baseline in POEM | 300 mg qw<br>300 mg q2w | −4.3 | −11.4<br>−11.9 |
| % patients with EASI-75 for patients with prior CSA use | 300 mg qw<br>300 mg q2w | 26.4% (N = 72) | 56.5% (N = 69)<br>58.0% (N = 69) |
| Mean weekly dose of TCS use during the treatment period | 300 mg qw<br>300 mg q2w | 25.1 | 17.5 (0.0003)<br>15.0 |
| Change from baseline in HADS | 300 mg qw<br>300 mg q2w | −2.3 | −5.2<br>−6.1 |

P-value, if not shown, for the efficacy endpoints in the testing hierarchies was <0.0001

The order of endpoints followed the pre-specified hierarchy test order in SAP. All secondary endpoints except the AE related endpoints were statistically significant at the 5% significance level.

Table 3 summarizes some of patient-reported outcomes and the improvements against baseline values

TABLE 3

Effect of dupilumab on selected patient-reported outcomes

| | Placebo + TCS (N = 108) | | 300 mg dupilumab q2w + TCS (N = 107) | |
|---|---|---|---|---|
| Baseline | | | | |
| SCORAD VAS sleep loss, mean ± SD | 4.3 ± 3.29 | | 4.6 ± 3.27 | |
| POEM score, mean ± SD | 19.1 ± 5.99 | | 19.3 ± 6.21 | |
| Pruritus NRS | | | | |
| Proportion of patients with ≥4-point improvement at Week 16, n/N1$^b$ (%) | 13/91 (14.3) | | 43/94 (45.7)*** | |
| Proportion of patients with ≥3-point improvement at Week 16, n/N1$^c$ (%) | 19/98 (19.4) | | 56/99 (56.6)*** | |
| SCORAD VAS | | | | |
| LS mean change from baseline to Week 16 (±SE) | | | | |
| Sleep loss$^d$ | −0.7 (0.25) | | −3.0 (0.25)*** | |
| LS mean percent change from baseline to Week 16 (±SE) | | | | |
| Sleep loss$^e$ | 85.8 (34.3) | | −61.2 (34.38)* | |
| POEM score | | | | |
| Mean change from baseline to Week 16 (±SE) | −3.5 (0.65) | | −11.7 (0.68)*** | |
| Proportion of patients with ≥4-point improvement at Week 16, n (%) | 45 (41.7) | | 89 (83.2)*** | |
| Proportion of patients reporting 'no days' or '1-2 days', n (%) | Baseline | Week 16 | Baseline | Week 16 |
| Last week days skin been itchy | 3 (2.8) | 19 (17.6) | 3 (2.8) | 49 (45.8)*** |
| Last week nights sleep been disturbed | 47 (43.5) | 59 (54.6) | 41 (38.3) | 89 (83.2)*** |
| Last week days skin been bleeding | 44 (40.7) | 52 (48.1) | 37 (34.6) | 90 (84.1)*** |
| Last week days been weeping/oozing | 54 (50.0) | 56 (51.9) | 45 (42.1) | 94 (87.9)*** |
| Last week days skin been cracked | 20 (18.5) | 36 (33.3) | 25 (23.4) | 81 (75.7)*** |
| Last week days skin been flaking off | 15 (13.9) | 28 (25.9) | 17 (15.9) | 70 (65.4)*** |
| Last week days skin felt dry or rough | 8 (7.4) | 21 (19.4) | 9 (8.4) | 64 (59.8)*** |

TABLE 3-continued

Effect of dupilumab on selected patient-reported outcomes

DLQI score

| | | |
|---|---|---|
| Proportion of patients with DLQI 0 or 1 at Week 16, n (%) | 12 (11.1) | 32 (29.9)** |
| Mean change from baseline to Week 16 (±SE) | −3.1 (0.58) | −9.7 (0.64)*** |
| Proportion of Patients with ≥4-point improvement at Week 16, n (%) | 42 (38.9) | 85 (79.4)*** |

| Proportion of patients reporting "no impact" or "little impact", n (%) | Baseline | Week 16 | Baseline | Week 16 |
|---|---|---|---|---|
| How itchy, sore, painful, stinging | 24 (22.2) | 46 (42.6) | 17 (15.9) | 89 (83.2)*** |
| How embarrassed, self-conscious | 53 (49.1) | 68 (63.0) | 51 (47.7) | 93 (86.9)*** |
| Interfered shopping, home, yard | 68 (63.0) | 80 (74.1) | 65 (60.7) | 100 (93.5)*** |
| Influenced clothes you wear | 47 (43.5) | 66 (61.1) | 47 (43.9) | 90 (84.1)*** |
| Affected social, leisure activity | 60 (55.6) | 69 (63.9) | 56 (52.3) | 98 (91.6)*** |
| Made it difficult to do any sports | 69 (63.9) | 72 (66.7) | 60 (56.1) | 97 (90.7)*** |
| Prevented/problem at working or studying | 62 (57.4) | 77 (71.3) | 59 (55.1) | 98 (91.6)*** |
| Problem partner, friends, relative | 72 (66.7) | 76 (70.4) | 68 (63.6) | 102 (95.3)*** |
| Caused any sexual difficulties | 84 (77.8) | 80 (74.1) | 68 (63.6)‡ | 100 (93.5)*** |
| How much a problem is treatment | 64 (59.3) | 72 (66.7) | 64 (59.8) | 96 (89.7)*** |

‡P < 0.05;
*P < 0.01;
**P < 0.001;
***P ≤ 0.0001.
$^a$Denotes severe disease;
$^b$Analysis was performed for patients with baseline peak pruritus NRS ≥4. N1 stands for number of patients with baseline NRS score ≥4;
$^c$Analysis was performed for patients with baseline peak pruritus NRS ≥3. N1 stands for number of patients with baseline NRS score ≥3;
$^d$Placebo + TCS: n = 107, 300 mg Dupilumab q2w + TCS: n = 106;
$^e$Placebo + TCS: n = 99, 300 mg Dupilumab q2w + TCS: n = 98;
$^f$MedDRA Preferred Term.
BSA, body surface area; DLQI, Dermatology Life Quality Index; EQ-5D, EuroQol five dimensions questionnaire; MedDRA, Medical Dictionary for Regulatory Activities; NRS, numerical rating scale; PGATE, Patient Global Assessment of Treatment Effect; POEM, Patient-Oriented Eczema Measure; q2w, every 2 weeks; SCORAD, Scoring Atopic Dermatitis; SE, standard error; TCS, topical corticosteroid.

Safety: Treatment with dupilumab plus concomitant TCS was well tolerated and demonstrated an acceptable safety profile during the 16-week treatment period. Table 4 summarizes selected AEs during the 16-week treatment period.

TABLE 4

Selected listing of AEs

| | Placebo + TCS (N = 108) | 300 mg dupilumab q2w + TCS (N = 107) |
|---|---|---|
| Number of patients with TEAEs, n (%) | 75 (69.4) | 77 (72.0) |
| Nasopharyngitis$^f$ | 18 (16.7) | 22 (20.6) |
| Conjunctivitis allergic$^f$ | 7 (6.5) | 16 (15.0) |
| Conjunctivitis$^f$ | 3 (2.8) | 12 (11.2) |
| Headache$^f$ | 9 (8.3) | 10 (9.3) |
| Atopic dermatitis$^f$ | 16 (14.8) | 8 (7.5) |
| Rhinitis allergic$^f$ | 1 (0.9) | 7 (6.5) |

$^f$MedDRA Preferred Term

No deaths occurred during the study. The percentage of patients with a treatment-emergent adverse event (TEAE) was similar across all treatment groups. Serious adverse events were evenly distributed among the treatment groups (2 events in each group). There were fewer severe TEAEs in the combined dupilumab-treated groups compared to placebo. Treatment with dupilumab did not increase the rate of infections: adverse events in the Infections and Infestations occurred at comparable rates in all treatment groups. There were also fewer skin infections in the combined dupilumab-treated groups compared to placebo. There was a higher incidence of conjunctivitis in the dupilumab-treated groups, with more events occurring in the 300 mg Q2W group than the 300 mg QW group. Only one event was severe in intensity and no patient discontinued treatment for an AE of conjunctivitis. Injection site reactions were more common in the dupilumab groups, with a higher rate in the 300 mg qw group versus the 300 mg q2w group; there were no severe ISRs.

Conclusion

In this 16-week study of dupilumab+TCS vs. placebo+TCS, the primary efficacy endpoint of EASI-75 at week 16 was met for both dupilumab dose regimens. EASI-75 responder rates at week 16 were 29.6% in placebo+TCS group, 62.6%, and 59.1% in dupilumab 300 mg q2w+TCS, and dupilumab 300 mg qw+TCS, respectively. All pre-specified key secondary and other secondary efficacy endpoints were met up to the endpoint of incidence of skin infection for the dupilumab 300 mg qw+TCS group.

Dupilumab with concomitant use of TCS was generally well tolerated with an acceptable safety profile.

In patients with a history of intolerance or inadequate response to CsA or for whom treatment with CsA is otherwise medically inadvisable, dupilumab and concomitant TCS, compared with TCS alone, significantly improved patient-reported itch, sleep, skin symptoms, and QoL, with an acceptable safety profile.

Example 2: Pharmacokinetics, Safety and Efficacy of Dupilumab in a Pediatric Population with Moderate-to-Severe or Severe AD: Results from a Phase 2a Clinical Trial This Example describes a phase 2a, multicenter, open-label, ascending-dose, sequential-cohort study (NCT02407756) which included adolescents (12-17 years) with moderate-to-severe AD and children (6-11 years) with severe AD, uncontrolled by topical medications. Patients received 2 mg/kg or 4 mg/kg single-dose subcutaneous dupilumab with 8 weeks follow-up, followed by 4 weekly 2 mg/kg or 4 mg/kg doses.

Study Objectives

The primary objective of the study was to characterize the safety and PK of dupilumab in pediatric patients with moderate-to-severe AD (for adolescents ≥12 to <18 years of age) or severe AD (for children ≥6 to <12 years of age). The secondary objective of the study was to explore the immunogenicity and efficacy of dupilumab in pediatric patients with moderate-to-severe AD (for adolescents ≥12 to <18 years of age) or severe AD (for children ≥6 to <12 years of age).

Study Design

This was conducted as a phase 2a, multicenter, open-label, ascending dose, sequential cohort study investigating the safety, tolerability, pharmacokinetics (PK), immunogenicity, and efficacy of single-dose and repeat-doses of subcutaneously administered (SC) dupilumab in pediatric patients with moderate-to-severe AD (for adolescents ≥12 to <18 years of age) or severe AD (for children ≥6 to <12 years of age) that was not adequately controlled by topical treatments.

Two sequential ascending SC dose cohorts were planned: dose cohort 1 (2 mg/kg) and dose cohort 2 (4 mg/kg) up to a maximum dose of 300 mg. Within each dose cohort, approximately 36 to 40 patients were planned to be enrolled in 2 age subsets: subset A (adolescents ≥12 to <18 years of age) and subset B (children ≥6 to <12 years of age). Enrollment and study dosing started with cohort 1A (2 mg/kg, adolescent age subset) and proceeded in sequence to cohort 1B (2 mg/kg, children ≥6 to <12 years of age subset), cohort 2A (4 mg/kg, adolescent age subset), and cohort 2B (4 mg/kg, children ≥6 to <12 years of age subset); a safety review of data from the previous cohort(s) was performed before proceeding to the next cohort.

The study consisted of a screening period (day −35 to day −1), a baseline visit, Part A (including a single-dose treatment followed by an 8-week semi-dense PK sampling period), and Part B (including a 4-week repeat-dose treatment period [4 weekly doses] followed by an 8-week follow-up period).

Patients received concomitant medications (except for prohibited medications) as needed, while continuing study treatment. Frequency of use and type of treatment were documented. If medically necessary, rescue treatments were provided to study patients. The rescue treatments included more intensive topical treatment (medications and/or procedures) before escalating rescue to systemic medications, if medically appropriate. Patients who received rescue with systemic corticosteroids or systemic nonsteroid immunosuppressive drugs (e.g., cyclosporine, methotrexate, mycophenolate-mofetil, azathioprine, etc.) during Part A (the single-dose treatment and 8-week semi-dense PK sampling period) needed to have such rescue treatment discontinued at least 2 weeks prior to start of Part B (i.e., prior to the start of administration of repeat-doses of study treatment); patients who received any of these rescue treatments during the repeat-dose treatment period were discontinued from study drug.

Dose Escalation:

Dosing started with cohort 1A. Proceeding to the next cohort (1B) occurred once all of the initial 8 patients enrolled in cohort 1A had been observed for at least 2 weeks, had completed the week 2 (day 15) safety assessments, and the data had been reviewed. Dosing escalated to cohort 2A once all of the initial 20 patients enrolled in cohorts 1A and/or 1B had been observed for at least 2 weeks, completed the week 2 (day 15) safety assessments, and the data had been reviewed. Proceeding to the next cohort (2B) occurred once all of the initial 8 patients enrolled in cohort 2A had been observed for at least 2 weeks, had completed the week 2 (day 15) safety assessments, and the data had been reviewed.

Study Population

The study population included pediatric patients with moderate-to-severe AD (for adolescents aged ≥2 to <18 years at the time of baseline) or severe AD (for children aged ≥6 to <12 years at the time of baseline) that was not adequately controlled with topical medications.

Inclusion Criteria:

A patient had to meet the following criteria to be eligible for inclusion in the study: (1) Male or female ≥6 to <18 years of age at the time of baseline; (2) Diagnosis of AD according to the American Academy of Dermatology criteria (Eichenfield et al 2014, J. Am. Acad. Dermatol. 70: 338-51) established at least 1 year before screening; (3) Patients with documented recent history (within 6 months before the screening visit) of inadequate response to a sufficient course of outpatient treatment with topical AD medication(s), or for whom topical AD therapies were otherwise inadvisable (e.g., because of side effects or safety risks). NOTE: For the purpose of this disclosure, inadequate response represented failure to achieve and maintain remission or a low disease activity state (comparable to Investigator's Global Assessment [IGA] 0=clear to 2=mild) despite treatment for at least 28 days with a regimen of TCS of medium to high potency (±TCI as appropriate). Side effects or safety risks that may outweigh the potential treatment benefits included intolerance to treatment, hypersensitivity reactions, significant skin atrophy, and side effects related to systemic absorption. Acceptable documentation included contemporaneous chart notes that recorded TCS with or without TCI prescription and treatment outcome, or investigator documentation based on communication with patient's treating physician. If documentation was inadequate, potential patients may have been re-screened after patients had been shown to fail mid-to-higher potency TCS (±TCI) for the prescribed length of treatment stated above. (4) IGA at baseline: a. IGA=3 or 4 in adolescents ≥12 to <18 year of age; b. IGA=4 in children ≥6 to <12 years of age; (5) At least 10% body surface area (BSA) affected by AD lesions at baseline. Note: This inclusion criterion was modified from the original criterion to clarify that the BSA affected by AD should be based on the assessment performed at baseline. (6) Willing and able to comply with clinic visits and study-related procedures; (7) With a parent/caregiver or legal guardian, able to understand the study requirements (8) Parent or legal guardian must have provided signed informed consent. Patients years of age (or above an age determined by the IRB/IEC and in accordance with the local regulations and requirements) must have also provided informed assent to enroll in the study, and must have signed and dated either a separate IAF or the ICF; and (9) Parent or legal guardian/patient, as appropriate, must have been able to understand and complete study-related questionnaires.

Exclusion Criteria:

A patient who met any of the following criteria was excluded from the study: (1) Treatment with an investigational drug within 8 weeks or within 5 half-lives (if known), whichever was longer, before the baseline visit; (2) The following treatments within 2 weeks before the baseline visit a. Systemic corticosteroids b. Immunosuppressive/immunomodulating drugs (e.g., cyclosporine, mycophenolate mofetil, interferon-gamma, Janus kinase inhibitors, azathioprine or methotrexate) c. Phototherapy for AD; (3) Treatment with biologics as follows: a. Any cell-depleting agents including, but not limited to, rituximab within 6 months before the baseline visit or until lymphocyte returned to normal, whichever was longer b. Other biologics within 5 half-lives (if known) or 4 months before the baseline visit, whichever was longer; (4) Planned or anticipated use of any prohibited medications and procedures during study treatment; (5) Treatment with a live (attenuated) vaccine within 3 months before the baseline visit; (6) Active chronic or acute infection requiring treatment with systemic antibiotics, antivirals, antiprotozoals, or antifungals within 4 weeks before the baseline visit, or superficial skin infections within 1 week before the baseline visit; (7) Known or suspected immunodeficiency, including history of invasive opportunistic infections (e.g., tuberculosis, histoplasmosis, listeriosis, coccidioidomycosis, pneumocystosis, aspergillosis) despite infection resolution, or otherwise recurrent infections of abnormal frequency or prolonged duration suggesting an immune compromised status; (8) Known history of human immunodeficiency virus infection; (9) Active infection with hepatitis B or C at screening, or a prior history of active infection with hepatitis B or C, as reported at time of screening; (10) Persistent (confirmed by repeated tests weeks apart) elevated transaminases (alanine aminotransferase [ALT] and/or aspartate aminotransferase [AST]) more than 3 times the upper limit of normal (ULN) during the screening period; (11) At baseline, presence of any conditions listed as criteria for study treatment discontinuation; (12) Presence of skin comorbidities that may have interfered with study assessments; (13) History of malignancy within 5 years before the baseline visit, except completely treated in situ carcinoma of the cervix and completely treated and resolved non-metastatic squamous or basal cell carcinoma of the skin; (14) History of clinical endoparasitosis (i.e., helminth infection) within 12 months before the baseline visit, or high risk of helminth infection, such as residence within or recent travel (within 12 months before the baseline visit) to areas endemic for endoparasitoses, where the circumstances were consistent with parasite exposure (e.g., extended stay, rural or slum areas, lack of running water, consumption of uncooked, undercooked, or otherwise potentially contaminated food, close contact with carriers and vectors, etc.), unless subsequent medical assessments (e.g., stool exam, blood tests, etc.) ruled out the possibility of parasite infection/infestation; (15) History of alcohol or drug abuse within 2 years before the screening visit; (16) Severe concomitant illness(es) that would have adversely affected the patient's participation in the study. Examples included, but were not limited to, patients with short life expectancy, patients with uncontrolled diabetes (hemoglobin A1c≥9%), patients with cardiovascular conditions (e.g., stage III or IV cardiac failure according to the New York Heart Association classification), severe renal conditions (e.g., patients on dialysis), hepatobiliary conditions (e.g., Child-Pugh class B or C), neurological conditions (e.g., demyelinating diseases), active major autoimmune diseases (e.g., lupus, inflammatory bowel disease, rheumatoid arthritis, etc.), and other severe endocrinological, gastrointestinal, metabolic, pulmonary, or lymphatic diseases; (17) Any other medical or psychological condition including relevant laboratory abnormalities at screening that suggested a new and/or insufficiently understood disease, may have presented an unreasonable risk to the study patient as a result of his/her participation in this clinical trial, may have made patient's participation unreliable, or may have interfered with study assessments; (18) Planned major surgical procedure during the patient's participation in this study; (19) Patient was a member of the investigational team or his/her immediate family; and (20) Female patients who were pregnant, breastfeeding, or planning to become pregnant or breastfeed during the study, or female patients of childbearing potential, who were unwilling to use adequate methods of contraception throughout the duration of the study and for 120 days after the last dose of study drug.

Study Treatments

Sterile dupilumab drug product 150 mg/mL was provided in an aqueous buffered vehicle, pH 5.0. It was supplied in a 5-mL vial containing 2.5 mL (150 mg/mL) with a withdrawable volume of 2.0 mL or 300 mg of dupilumab. Study drug was administered SC by the investigator or other qualified study personnel at the following dose and dosing schedules:

For dose cohort 1: 2 mg/kg at day 1 as a single dose in Part A, then weekly at day 1 to week 3 in Part B as repeat doses For dose cohort 2: 4 mg/kg at day 1 as a single dose in Part A, then weekly at day 1 to week 3 in Part B as repeat doses Subcutaneous injection sites of the study drug were to be alternated among the different quadrants of the abdomen (avoiding navel and waist areas), upper thighs, and upper arms so that the same site was not injected for 2 consecutive weeks. To allow for adequate assessment of possible injection site reactions, study drug was to be administered only into areas of normal-looking skin.

Primary and Secondary Endpoints

The primary objective was characterizing the PK profiles of dupilumab in pediatric AD patients aged ≥6 to <18 years. The secondary endpoints were:

Incidence of TEAEs

Percent change from baseline in Eczema Area and Severity Index (EASI)

Percent change from baseline in SCORing Atopic Dermatitis (SCORAD) score

Percent change from baseline in Pruritus Numerical Rating Scale (NRS)

Percentage of patients with an IGA score of 0 or 1

Change from baseline in % BSA affected by AD

Study Variables and Procedures

Safety and tolerability was assessed by vital signs, physical examinations, clinical laboratory tests, and clinical evaluations. Patients were asked to monitor all adverse events (AEs) experienced from the time of informed consent/assent until their last study visit. Serum samples were collected for assay of dupilumab levels, and PK parameters were calculated using the dupilumab concentration data. Serum samples were collected for assay of ADA, and exploratory analyses. Efficacy was assessed during the study at specified clinic visits using the Pruritus NRS, SCORAD, and EASI that measure the extent and severity of AD, and the IGA that rates the overall severity of AD.

Results (A) Baseline Disease Characteristics

This study enrolled adolescent patients aged ≥12 to <18 years with moderate-to-severe AD (baseline IGA score of 3 or 4) and children aged ≥6 to <12 years with severe AD (baseline IGA score of 4; see inclusion criteria for each age group). Therefore, disease characteristics at baseline differed between the two age groups.

Adolescent Patients Aged ≥12 to <18 Years:

The proportion of adolescent patients diagnosed with AD within specified age ranges was generally similar between the dose cohorts, with the majority of patients in each dose cohort diagnosed before the age of 5 (Table 1). The mean duration of AD was also similar between the dose cohorts. As expected, patients in the older age subsets within each dose cohort had a longer duration of AD than younger patients. Mean baseline values for all AD assessments were consistent with moderate-to-severe AD. Differences in mean EASI score at baseline, mean pruritus NRS score, mean BSA and SCORAD score were minor and consistent with that expected in non-randomized groups (Table 5). Overall, the baseline disease characteristics were comparable between the 2 dose cohorts.

TABLE 5

Summary of Baseline Disease Characteristics for Adolescent Patients Aged ≥12 to <18 Years

| | 2 mg/kg SC (N = 20) | 4 mg/kg SC (N = 20) | Total (N = 40) |
|---|---|---|---|
| Chronic AD Diagnosis Age: | | | |
| Before 5 years of age | 16 (80%) | 18 (90%) | 34 (85%) |
| Between 5 and 9 years of age | 3 (15%) | 2 (10%) | 5 (12.5%) |
| Between 10 and 17 years of age | 1 (5%) | 0 | 1 (2.5%) |
| Duration of AD (years) Mean (SD) | 11.8 (4.21) | 12.5 (2.28) | 12.2 (3.36) |
| EASI score Mean (SD) | 34.8 (17.00) | 28.6 (14.70) | 31.7 (16.00) |
| Number n (%) of patients with IGA score 3 | 8 (40%) | 11 (55%) | 19 (47.5%) |
| Number n (%) of patients with IGA score 4 | 12 (60%) | 9 (45%) | 21 (52.5%) |
| Pruritus NRS Mean (SD) | 6.1 (2.47) | 6.9 (2.21) | 6.5 (2.34) |
| Number n (%) of patients with Pruritus NRS ≥3 | 18 (90%) | 19 (95%) | 37 (92.5%) |
| Number n (%) of patients with Pruritus NRS ≥4 | 15 (75%) | 18 (90%) | 33 (82.5%) |
| BSA Mean (SD) | 52.2 (24.78) | 45.9 (25.34) | 49 (24.94) |
| SCORAD Mean (SD) | 68.0 (13.19) | 63.0 (14.43) | 65.5 (13.88) |

BSA, body surface area;
EASI, Eczema Area Severity Index;
IGA, Investigator's Global Assessment;
NRS, numerical rating scale;
SAF, safety analysis set;
SC, subcutaneous;
SCORAD, Scoring Atopic Dermatitis;
SD, standard deviation Patients Aged ≥6 to <12 Years:

The proportion of patients aged ≥6 to <12 years diagnosed with AD within specified age ranges was generally similar between the dose cohorts, with the majority of patients in each dose cohort diagnosed before the age of 5 (Table 2). The mean duration of AD was also similar between the dose cohorts. As expected, patients in the older age subsets within each dose cohort had a longer duration of AD than younger patients. Mean baseline values for all AD assessments were consistent with severe/moderate AD. Differences in mean EASI score at baseline, mean pruritus NRS score, mean BSA and SCORAD score were minor and consistent with that expected in non-randomized groups (Table 6). Overall, the baseline disease characteristics were comparable between the 2 dose cohorts.

TABLE 6

Summary of Baseline Disease Characteristics - Children >=6 to <12 Years of Age

| | 2 mg/kg SC (N = 18) | 4 mg/kg SC (N = 19) | Total (N = 37) |
|---|---|---|---|
| Chronic AD Diagnosis Age | | | |
| Before 5 years of age | 16 (88.9%) | 19 (100%) | 35 (94.6%) |
| Between 5 and 9 years of age | 2 (11.1%) | 0 | 2 (5.4%) |
| Duration of AD (years) Mean (SD) | 6.8 (2.46) | 7.4 (2.24) | 7.1 (2.33) |
| EASI Mean (SD) | 32.9 (15.53) | 38.8 (18.64) | 35.9 (17.22) |
| Number n (%) of patients with IGA score 3 | 1 (5.6%) | 0 | 1 (2.7%) |
| Number n (%) of patients with IGA score 4 | 17 (94.4%) | 19 (100%) | 36 (97.3%) |
| Pruritus NRS Mean (SD) | 6.4 (2.23) | 6.7 (2.35) | 6.6 (2.27) |
| Number n (%) of patients with Pruritus NRS ≥3 | 18 (100%) | 18 (94.7%) | 36 (97.3%) |
| Number n (%) of patients with Pruritus NRS ≥4 | 18 (100%) | 17 (89.5%) | 35 (94.6%) |
| BSA Mean (SD) | 59.0 (22.49) | 62.3 (30.34) | 60.7 (26.49) |
| SCORAD Mean (SD) | 66.4 (13.06) | 72.7 (12.96) | 69.7 (13.22) |

BSA, body surface area;
EASI, Eczema Area Severity Index;
IGA, Investigator's Global Assessment;
NRS, numerical rating scale;
SAF, safety analysis set;
SC, subcutaneous;
SCORAD, Scoring Atopic Dermatitis;
SD, standard deviation (B) Medical History Medical history was assessed using a general questionnaire, and specific atopic disease medical history was collected using a targeted questionnaire that elicited extensive atopic history.

Adolescent Patients Aged ≥12 to <18 Years:

All adolescent patients (100%) had at least 1 medical history finding using the general questionnaire. The most common non-AD MedDRA PTs reported in ≥30% of patients overall were Food Allergy (45.0%), Asthma (45.0%), House Dust Allergy (35.0%), Seasonal Allergy (35.0%), Allergic Rhinitis (35.0%), and Allergy to Animal (30.0%). A history of allergic conjunctivitis was present in 11 (27.5%) patients.

Based on the specific atopic disease questionnaire, the proportion of patients with a family history of atopic/allergic conditions was similar between the two dose cohorts. The most common atopic/allergic condition in patient family history was AD (37.5% overall). The most common atopic/allergic condition in patient family history in the 2 mg/kg dose cohort was AD (50.0%) whereas in the 4 mg/kg dose cohort it was Other Allergies (30.0%). The most common current atopic/allergic condition other than AD was Other Allergies (60.0% overall; 55.0% in the 2 mg/kg dose cohort and 65.0% in the 4 mg/kg dose cohort). Overall, 30.0% of all patients indicated a current history of Allergic Conjunctivitis and 37.5% had a current history of Asthma, both of which were reported in higher proportions of patients in the 4 mg/kg dose cohort. Five percent of all patients had a currently resolved atopic/allergic condition. The most common currently resolved atopic/allergic condition was Asthma, which was reported at a similar frequency in both dose cohorts.

Patients ≥6 to <12 Years of Age:

All patients aged ≥6 to <12 years (100%) had at least 1 medical history finding using the general questionnaire. The most common non-AD MedDRA PTs reported in ≥30% of patients overall were Food Allergy (67.6%), Allergic Rhinitis (51.4%), House Dust Allergy (48.6%), Asthma (43.2%), and Seasonal Allergy (35.1%). A history of allergic conjunctivitis was present in 9 (24.3%) patients. In general, medical history was similar between the dose cohorts. Differences between dose cohorts included a higher incidence of Food Allergy (73.7%, 61.1%), Milk Allergy (15.8%, 5.6%), and Allergic Conjunctivitis (31.6%, 16.7%) in the 4 mg/kg dose cohort than in the 2 mg/kg dose cohort, respectively. The incidence of Allergy to Animal (38.9%, 5.3%), Mycotic Allergy (16.7%, 5.3%), and Allergic Rhinitis (61.1%, 42.1%) were higher in the 2 mg/kg dose cohort than in the 4 mg/kg dose cohort, respectively.

Based on the specific atopic disease questionnaire, the proportion of patients with a family history of atopic/allergic conditions was higher in the 4 mg/kg dose cohort than in the 2 mg/kg dose cohort. The most common atopic/allergic condition in patient family history was AD (32.4% overall). The most common atopic/allergic condition in patient family history in the 2 mg/kg dose cohort was Allergic Rhinitis (33.3%) whereas in the 4 mg/kg dose cohort it was AD (36.8%). The most common current atopic/allergic conditions other than AD were Other Allergies and Food Allergy (64.9% overall each). The incidence of current Food Allergy was higher in the 4 mg/kg dose cohort (73.7%) than in the 2 mg/kg dose cohort (55.6%). Overall, 21.6% of all patients indicated a current history of Allergic Conjunctivitis and 43.2% had a current history of Asthma, both of which were reported in higher proportions of patients in the 4 mg/kg dose cohort.

(C) Previous Medications/Procedures

Prior medications/procedures were defined as medications taken or procedures performed prior to the first administration of study drug.

Adolescent Patients Aged ≥12 to <18 Years:

All adolescent patients received at least 1 prior medication. The most commonly used (≥50% of all patients) prior medications by therapeutic class were Corticosteroids Dermatological Preparations (97.5%), Antihistamines for Systemic Use (67.5%), and Other Dermatological Preparations (67.5%). Prior medication use was generally similar between the 2 dose cohorts. Dermatological preparations of corticosteroids included potent (Group III; 87.5% patients overall), weak (Group I; 35.0% patients overall), moderately potent (Group II; 27.5% patients overall), and very potent (Group IV; 12.5%). A total of 7 (17.5%) adolescent patients had a history of systemic glucocorticoid use. Thirteen patients reported prior use of a non-steroidal systemic immunosuppressant, which included cyclosporine and azathioprine. Nine (22.5%) adolescent patients reported at least 1 prior procedure. The most commonly reported prior procedures in >1 patient were ultraviolet (UV) light therapy (7.5% patients overall) and phototherapy (5.0% patients overall).

Patients ≥6 to <12 Years of Age:

All patients aged ≥6 to <12 years received at least 1 prior medication. The most commonly used (≥50% of all patients) prior medications by therapeutic class were Corticosteroids Dermatological Preparations (97.3%), Antihistamines for Systemic Use (91.9%), Emollients and Protectives (70.3%), and Other Dermatological Preparations (70.3%). Prior medication use was generally similar between the 2 dose cohorts. Dermatological preparations of corticosteroids included potent (Group III; 83.8% patients overall), moderately potent (Group II; 43.2% patients overall), weak (Group I; 29.7% patients overall), and very potent (Group IV; 10.8%). Prior systemic glucocorticoid use was reported by 11 (29.7%) patients. Ten patients reported prior use of a non-steroidal systemic immunosuppressant, including cyclosporine and azathioprine. Seven (18.9%) patients reported at least 1 prior procedure. Prior procedures reported by >1 patient overall included UV light therapy (10.8% patients overall) and phototherapy (5.4% patients overall).

(D) Concomitant Medications and Procedures

Adolescent Patients Aged ≥12 to <18 Years:

Most adolescent patients (97.5%) received at least 1 concomitant medication during the entire Study. The most commonly (25% patients overall) used concomitant medications by therapeutic class throughout the entire study were Corticosteroids Dermatological Preparations (75.0%), Antihistamines for Systemic Use (67.5%), Emollients and Protectives (45.0%), Other Dermatological Preparations (42.5%), and Drugs for Obstructive Airway Diseases (27.5%). Overall, 77.5% of patients used concomitant treatments for AD during the study, including 85.0% of patients in the 2 mg/kg dose cohort and 70.0% of patients in the 4 mg/kg dose cohort. The use of any TCS was higher in the 2 mg/kg dose cohort than in the 4 mg/kg dose cohort. The most commonly used TCS in both dose cohorts was potent (Group III) TCS. The use of TCI was also higher in the 2 mg/kg dose cohort than in the 4 mg/kg dose cohort. Tacrolimus was the most commonly used TCI in both dose cohorts. The number of adolescent patients who used any concomitant AD medication was higher during the Part A period (31 [77.5%]) than during the Part B period (11 [27.5%]). TCS and TCI use in adolescents was higher for both dose cohorts during the Part A period compared to the Part B period. Systemic corticosteroid use was low and comparable between Part A and Part B.

Patients ≥6 to <12 Years of Age:

Most patients aged ≥6 to <12 years (97.3%) received at least 1 concomitant medication during the entire study. The most commonly (≥25% patients overall) used concomitant medications by therapeutic class throughout the entire study were Antihistamines for Systemic Use (89.2%), Corticosteroids Dermatological Preparations (89.2%), Emollients and Protectives (75.7%), Other Dermatological Preparations (48.6%), Drugs for Obstructive Airway Diseases (40.5%) which may represent an overlap with asthma as a comorbidity, and Antibacterials for Systemic Use (27.0%). Overall, 91.9% of patients aged ≥6 to <12 years used concomitant treatments for AD during the study, including 88.9% of patients in the 2 mg/kg dose cohort and 94.7% of patients in the 4 mg/kg dose cohort. The use of any TCS was similar between the dose cohorts, and the most commonly used TCS in both dose cohorts was potent (Group III) TCS. The use of TCI was higher in the 2 mg/kg dose cohort than in the 4 mg/kg dose cohort. Tacrolimus was the most commonly used TCI in both dose cohorts. The number of patients ≥6 to <12 years of age who required the use of any concomitant AD medication was higher during the Part A period (33 [89.2%]) than during the Part B period (10 [27%]). The use of TCS and TCI was also higher during the Part A period than during the Part B period for both dose cohorts. No systemic immunosuppressant use was required during either Part A or Part B in the ≥6 to <12 years age group.

(E) Efficacy 40 adolescents/38 children (mean Eczema Area and Severity Index [EASI]±SD=31.7±16.00/35.9±17.22) were enrolled; 22.5% adolescents/16.2% children did not respond to ≥1 previous systemic treatment. The pharmacokinetic profile of dupilumab was similar to adults (target-mediated drug disposition). No new safety signals were detected compared with adults.

In the adolescent patients group, dupilumab administered as a single dose of either 2 mg/kg or 4 mg/kg induced significant and rapid reduction of disease activity in patients at week 2 (34% and 51% reduction in EASI score from baseline for 2 mg/kg and 4 mg/kg doses respectively). Repeated weekly doses of dupilumab led to a further improvement in disease severity in patients in both dose cohorts. At Week 12, in adolescent 2 mg/4 mg cohorts, baseline EASI significantly improved by 66.4%/69.7%, and peak pruritus Numerical Rating Scale (NRS) by 30.8%/37.6%; 10%/35% achieved an Investigator Global Assessment (IGA) 0-1.

Dupilumab administered as a single dose of either 2 mg/kg or 4 mg/kg induced significant and rapid reduction of disease activity in patients at week 2 (37% and 33% reduction in EASI score from baseline for 2 mg/kg and 4 mg/kg doses, respectively) Repeated weekly doses of dupilumab led to a further improvement in disease severity in patients in both dose cohorts. At Week 12 in children 2 mg/4 mg cohorts, baseline EASI significantly improved by 76.2%/63.4% and peak pruritus NRS by 41.6%/39.6%; 16.7%/21.1% achieved IGA 0-1.

Overall, both dose regimens studied showed significant clinical benefit in both pediatric age groups. Single doses of 2 mg/kg and 4 mg/kg dupilumab led to a rapid reduction in signs and symptoms of AD in both age groups. Repeated weekly doses provided an improved and more sustained response than a single dose in both age groups. This clinical response was seen in patients with high disease activity at baseline and who had failed all approved available therapies for their disease.

Conclusions

Dupilumab administered as single and repeated weekly doses of 2 mg/kg and 4 mg/kg for 4 weeks was generally safe and well tolerated in both pediatric age groups included in this study. In pediatric patients with AD, the dupilumab pharmacokinetic profile was consistent with adults; dupilumab provided clinical benefit (including itch improvement) faster than rates observed in adult clinical trials with a similar safety profile.

Example 3: Treatment Interruption Did not Impact Efficacy or Long-Term Safety of Dupilumab: A Phase 3 Open-Label Trial Treatment interruption may occur in clinical practice. The objective of this study is to present the effect of treatment interruption on long-term safety and efficacy of dupilumab.

This Example presents an interim analysis of an ongoing multicenter, open-label trial (NCT01949311) of dupilumab treatment for up to 3 yrs. Adults with moderate-to-severe atopic dermatitis (AD) were enrolled after participation in prior dupilumab trials. Safety and efficacy at Week [Wk] 52 for dupilumab naïve (previously unexposed) and retreated (>13 Wk gap between parent and open-label study) patients were evaluated.

Of the 1,491 treated patients, 116 naïve and 290 retreated patients were included in this analysis (includes patients who finished to or withdrew before Wk52). Naïve and retreated patients had 432.5 and 371.0 adverse events/100 patient years (AEs/100PY), 11.7 and 5.4 serious AEs/100PY, and 2.6% and 2.8% treatment discontinuations due to AEs, respectively; there were no deaths. At Wk52, 49.1%/50.7% naïve/retreated patients had an Investigator's Global Assessment score of 0 or 1, and 73.3%/80.7% achieved EASI-75 (from baseline of parent study); peak pruritus Numerical Rating Scale scores at Wk52 decreased by 64.9% and 60.6% from baseline of parent study for naïve and retreated patients. Overall, efficacy assessment at all time points previous to W52 showed similar results between groups.

In conclusion, interruption of dupilumab treatment for over 3 months had no effect on safety or efficacy endpoints in adults with moderate-to-severe AD compared with treatment naïve patients.

Example 4: Efficacy and Safety of Dupilumab in Adult Patients with Atopic Dermatitis Who were Candidates for Systemic Treatment with Cyclosporine: Subgroup Analysis from a One-Year Trial Atopic dermatitis (AD) is a chronic inflammatory skin disease that may persist for decades requiring systemic therapy for extended periods of time. Cyclosporine (CsA) provides a rapid and broad immunosuppressive effect but its long-term use is limited due to safety concerns including hypertension and impaired renal and hepatic function. Dupilumab, a fully human monoclonal antibody directed against interleukin (IL)-4 receptor alpha, inhibits type 2 cytokines IL-4 and IL-13. Long-term safety and efficacy of dupilumab was investigated in a phase 3 clinical trial (NCT02260986).

This Example describes a 1-year, double-blind, randomized, placebo-controlled, parallel-group study in adults with moderate-to-severe-AD and a history of inadequate response to topical corticosteroids (TCS). Patients were randomized 3:1:3 (dupilumab 300 mg weekly [qw], every two weeks [q2w], or placebo). Patients received concomitant low and/or medium potency TCS, which could be tapered and discontinued based on clinical response. Topical calcineurin inhibitors could be used in areas considered inadvisable for TCS.

Here we compare the efficacy and safety of dupilumab versus placebo in two patient subsets of the population: patients who had a documented history of inadequate response or intolerance to CsA, or had been considered for CsA, based on severity of AD, but had not received CsA treatment as it was contraindicated or inappropriate (CsA-ineligible, n=126) and the remaining CsA-eligible subset (n=497).

CsA-ineligible patients had, on average, more severe disease than CsA-eligible patients, as assessed by Eczema Area and Severity Index (EASI) (mean baseline±SD EASI score 36.9±13.09 vs 31.5±12.66; nominal p<0.001 [post-hoc analysis]). At Week 52 in both subsets, dupilumab treatment increased the proportion of patients achieving a 75% improvement in EASI (CsA-ineligible: 18.6% placebo, 52.4%/50.0% dupilumab q2w/qw; CsA-eligible: 22.4% placebo, 69.1%/67.0% dupilumab q2w/qw). Dupilumab treatment also increased the proportion of patients achieving a ≥4-point improvement in peak pruritus numerical rating scale at Week 52 (CsA-ineligible: 12.3% placebo, 42.9%/35.6% dupilumab q2w/qw; CsA-eligible: 13.0% placebo, 53.8%/39.7% dupilumab q2w/qw). Treatment groups had similar treatment-emergent adverse event (TEAE) rates (CSA-ineligible: 88.5%, 91.7%/88.5%; CSA-eligible: 88.3%, 87.2%/81.7%).

In further analysis, the efficacy and safety of dupilumab vs placebo (PBO) at 52 weeks was compared in two patient (pt) subsets of the population: pts who were earlier treated with CsA but responded inadequately or were intolerant to CsA (subset A; n=114) and the remaining study population (subset B; n=509). Subset A pts had, on average, more severe disease than subset B pts, as assessed by Eczema Area and Severity Index (EASI) (mean baseline±SD EASI score 37.0±12.70 vs 31.6±12.77; nominal p<0.0001 [post-hoc analysis]). At Week 52 in both subsets, dupilumab treatment increased the proportion of pts achieving a 75% improvement in EASI; and the proportion of pts achieving a ≥4-point improvement in peak pruritus numerical rating scale (Table 7). Treatment groups had similar treatment-emergent adverse event (TEAE) rates (Subset A: 88.9%, 90.9%/87.0%; Subset B: 83.5%, 87.5%/82.2%).

Cyclosporine (CsA) is approved for this indication; however, its clinical use is limited primarily due to safety concerns including hypertension and impaired renal and hepatic function. Dupilumab, a fully human anti-interleukin (IL)-4 receptor alpha monoclonal antibody, potently inhibits both IL-4 and IL-13 signaling. Dupilumab has been reported to improve AD outcomes while having an acceptable safety profile in 2 identically designed phase 3 trials of pts with moderate-to-severe AD (NCT02277743 and NCT02277769).

Objective and Methods:

To evaluate the efficacy and safety of dupilumab versus placebo in two subsets of the pooled population: pts who had a documented history of inadequate response or intolerance to CsA, or had been considered for CsA, based on severity of AD, but had not received CsA treatment as it was contraindicated or inappropriate (CsA-ineligible, n=288) and the remaining CsA-eligible subset (n=1091). Pts (N=1379) with moderate-to-severe AD whose disease was not adequately controlled by topical medications or for whom topical treatment is medically inadvisable were randomized to receive subcutaneous injections of placebo (PBO) or dupilumab 300 mg every 2 weeks (q2w) or weekly (qw) for 16 weeks.

TABLE 7

Comparison of efficacy of dupilumab in CsA-exposed patients (Subset A) and CsA-naïve patients (subset B)

| | Subset A (n = 114) Inadequate response or intolerance to CsA | | | Subset B (n = 509) Remaining study population | | |
|---|---|---|---|---|---|---|
| | PBO ± TCS (N = 52) | Dupilumab 300 mg Q2W ± TCS (N = 19) | Dupilumab 300 mg QW ± TCS (N = 43) | PBO ± TCS (N = 212) | Dupilumab 300 mg Q2W ± TCS (N = 70) | Dupilumab 300 mg QW ± TCS (N = 227) |
| Patients achieving EASI-75, n (%) | 10 (19.2) | 10 (52.6) | 21 (48.8) | 47 (22.2) | 48 (68.6) | 152 (67.0) |
| Patients achieving a peak pruritus NRS score improvement ≥4 points from baseline, n/N1 (%)† | 6/51 (11.8) | 9/19 (47.4) | 16/42 (38.1) | 26/198 (13.1) | 35/67 (52.2) | 81/207 (39.1) |
| Patients with at least one treatment-emergent adverse event, n/N (%)‡ | 48/54 (88.9) | 20/22 (90.9) | 40/46 (87.0) | 218/261 (83.5) | 77/88 (87.5) | 221/269 (82.2) |

†Analysis was performed for patients with baseline peak pruritus NRS ≥4.
N1 stands for number of patients with baseline NRS score ≥4.
EASI-75, 75% improvement in EASI from baseline; NRS, numerical rating scale.
‡N stands for number of patients included in the safety analysis set The most common TEAEs were upper respiratory tract infections, nasopharyngitis, conjunctivitis, AD exacerbations, and injection site reaction.

In conclusion, long-term treatment with dupilumab significantly improved signs and symptoms of AD regardless of a documented history of inadequate response or intolerance to CsA and even though these patients had significantly increased disease activity at baseline. Similarly, dupilumab improved signs and symptoms of AD in patients who were eligible for CsA.

Example 5: Efficacy and Safety of Dupilumab in Adult Patients with Atopic Dermatitis Who were Candidates for Treatment with Cyclosporine: Pooled Secondary Subgroup Analysis of Two Phase 3 Randomized Trials Introduction:

Patients (pts) with atopic dermatitis (AD) refractory to topical treatment are candidates for systemic treatment.

Results:

CsA-ineligible pts had, on average, more severe disease than CsA-eligible pts, as assessed by Eczema Area and Severity Index (EASI; mean baseline±SD EASI score 36.1±14.54 vs 32.1±13.35; nominal p<0.0001). In both subsets, dupilumab treatment increased the proportion of pts reaching a 75% improvement in EASI; achieving Investigator's Global Assessment 0-1; or reporting a ≥4-point improvement in peak pruritus numerical rating scale (Table 8). The most common treatment-emergent adverse events in these studies were nasopharyngitis, AD exacerbations, and injection site reactions. In both subsets, bacterial conjunctivitis (CsA-ineligible 1.1%, 3.8%/4.2% PBO, dupilumab q2w/qw; CsA-eligible 0.3%, 0.6%/1.1%) and conjunctivitis rates (CsA-ineligible 2.3%, 1.9%/4.2%; CsA-eligible 0.3%, 5%/3.3%) were numerically higher in the dupilumab groups than in the PBO groups.

TABLE 8

Comparison of efficacy of dupilumab in CsA-ineligible and CsA-eligible patients

| | CSA-ineligible subset | | | CSA-eligible subset | | |
|---|---|---|---|---|---|---|
| | PBO (N = 88) | Dupilumab 300 mg Q2W (N = 104) | Dupilumab 300 mg QW (N = 96) | PBO (N = 372) | Dupilumab 300 mg Q2W (N = 353) | Dupilumab 300 mg QW (N = 366) |
| Patients achieving EASI 75, n (%) | 10 (11.4) | 42 (40.4) | 34 (35.4) | 51 (13.7) | 176 (49.9) | 198 (54.1) |
| Patients achieving IGA 0-1, n (%) | 6 (6.8) | 32 (30.8) | 27 (28.1) | 37 (9.9) | 137 (38.8) | 143 (39.1) |
| Patients achieving a ≥4-point improvement in peak pruritus NRS, n/N1 (%)† | 7/88 (8.0) | 33/98 (33.7) | 33/91 (36.3) | 40/345 (11.6) | 135/340 (39.7) | 137/338 (40.5) |

†Analysis was performed for patients with baseline peak pruritus NRS ≥4.
N1 stands for number of patients with baseline NRS score ≥4.
EASI-75, 75% improvement in EASI from baseline; IGA, Investigator's Global Assessment; NRS, numerical rating scale.

In further analysis, the efficacy and safety of dupilumab versus placebo was compared in two subsets of the pooled population: pts who had a documented history of inadequate response or intolerance to CsA (subset A; n=255) and the remaining study population (subset B; n=1124). Subset A pts had, on average, more severe disease than subset B pts, as assessed by Eczema Area and Severity Index (EASI; mean baseline±SD EASI score 37.2±14.69 vs 32.0±13.29; nominal $p<0.0001$). In both subsets, dupilumab treatment increased the proportion of pts reaching a 75% improvement in EASI (Table 5); achieving Investigator's Global Assessment 0-1 (Table 9); or reporting a ≥4-point improvement in peak pruritus numerical rating scale (Table 9).

Methods:

The clinical trial was a 52-week randomized, multicenter, double-blind, placebo-controlled trial of subcutaneous dupilumab with concomitant topical corticosteroids (TCS) in 740 adult patients (NCT02260986) randomized 3:1:3 to placebo, dupilumab 300 mg every 2 weeks (q2w) and dupilumab 300 mg every week (qw); patients randomized to dupilumab received a loading dose of 600 mg. An open-label extension study of dupilumab 300 mg qw (NCT01949311) is ongoing in patients who participated in prior studies and results from 1076 patients treated for up to 68 weeks are also reported. This Example describes functional dupilumab concentra-

TABLE 9

Comparison of efficacy of dupilumab in CsA-exposed patients (Subset A) and CsA-naïve patients (subset B)

| | Subset A Inadequate response or intolerance to CsA | | | Subset B Remaining study population | | |
|---|---|---|---|---|---|---|
| | PBO (N = 78) | Dupilumab 300 mg Q2W (N = 94) | Dupilumab 300 mg QW (N = 83) | PBO (N = 382) | Dupilumab 300 mg Q2W (N = 363) | Dupilumab 300 mg QW (N = 379) |
| Patients achieving EASI 75, n (%) | 10 (12.8) | 36 (38.3) | 29 (34.9) | 51 (13.4) | 182 (50.1) | 203 (53.6) |
| Patients achieving IGA 0-1, n (%) | 6 (7.7) | 28 (29.8) | 23 (27.7) | 37 (9.7) | 141 (38.8) | 147 (38.8) |
| Patients achieving a ≥4-point improvement in peak pruritus NRS, n/N1 (%)† | 7/78 (9.0) | 30/89 (33.7) | 28/82 (34.1) | 40/355 (11.3) | 138/349 (39.5) | 142/379 (40.9) |

†Analysis was performed for patients with baseline peak pruritus NRS ≥4.
N1 stands for number of patients with baseline NRS score ≥4.
EASI-75, 75% improvement in EASI from baseline; IGA, Investigator's Global Assessment; NRS, numerical rating scale.

Conclusion:

Dupilumab 16-week monotherapy significantly improves signs and symptoms of AD in both pts not eligible for treatment with CsA (even though these pts had significantly increased disease activity at baseline), as well as in those who were eligible for CsA treatment.

Example 6: Pharmacokinetics of Dupilumab in Long-Term Phase 3 Studies in Adult Patients with Moderate-to-Severe Atopic Dermatitis This Example presents pharmacokinetic (PK) data from two long-term phase 3 studies conducted to evaluate the efficacy and safety of dupilumab in adults with moderate-to-severe atopic dermatitis.

tions measured in serum from blood samples at various time-points and analyzed using descriptive statistics.

Results:

In the randomized study, mean functional concentrations of dupilumab in serum increased from Week 2 to Week 16, reaching 80 mg/L and 185 mg/L for the q2w and qw treatment groups, respectively. The results are consistent with published data from patients not receiving TCS, suggesting that concomitant use does not affect the dupilumab PK. Steady-state concentrations were maintained for the remainder of treatment. Concentrations in the qw group of the 52-week trial were similar in the open-label extension study at Week 20 through Week 68.

Conclusions:

Mean functional concentrations of dupilumab in serum were consistent for both studies, suggesting that there is no time-dependent change in PK during long-term treatment.

Example 7: Pharmacokinetics of Dupilumab in Phase 3 Confirmatory Studies in Adult Patients with Moderate-to-Severe Atopic Dermatitis This Example describes pharmacokinetic (PK) data from two phase 3 studies conducted to assess the efficacy and safety of dupilumab monotherapy in adults with moderate-to-severe atopic dermatitis.

Methods:

The studies were multicenter, randomized, double-blind, placebo-controlled studies of subcutaneously administered dupilumab in 1379 adult patients; each had duration of 16 weeks (NCT02277743 and NCT02277769). Patients were randomized 1:1:1 to placebo, dupilumab 300 mg every week (qw), and dupilumab 300 mg every 2 weeks (q2w); patients randomized to dupilumab received a loading dose of 600 mg. Presented here are functional dupilumab concentrations measured in serum from blood samples at various pharmacokinetic time-points and analyzed using descriptive statistics.

Results:

Mean functional concentrations of dupilumab in serum increased from Week 2 to Week 16, reaching ~75 mg/L and 180 mg/L for the dupilumab 300 q2w and dupilumab 300 qw treatment groups, respectively, with a ratio (qw:q2w) of 2.4 at Week 16. The mean $C_{trough}$ values at Week 12 indicated that dupilumab $C_{trough}$ values were at steady state at Weeks 12 through 16 with both dosing regimens. A 600 mg loading dose enabled a rapid approach to steady state at the q2w dose, allowing ~80% of the Week 12 $C_{trough}$ to be reached by Week 4. With the qw dose, ~67% of the Week 12 $C_{trough}$ was reached by Week 4.

Conclusions:

The pharmacokinetic profile of dupilumab in the phase 3 studies was consistent with early phase clinical studies and the ratio of $C_{trough}$ at Week 16 was close to dose proportional for the q2w and qw regimens studied.

Example 8: Effect of Dupilumab on the Pharmacokinetics of Cytochrome P450 Substrates in Adult Patients with Moderate-to-Severe Atopic Dermatitis: An Open Label Phase I Trial This study assessed the effect of dupilumab on the PK of 5 CYP isoform-specific substrates, as well as safety and efficacy of dupilumab in an open-label phase 1 trial (NCT02647086).

Methods:

Adults with moderate-to-severe AD received an oral cocktail consisting of midazolam, omeprazole, S-warfarin, caffeine, and metoprolol (metabolized by CYP3A, CYP2C19, CYP2C9, CYP1A2, and CYP2D6, respectively), on Days 1 and 36. Subcutaneous dupilumab was administered as a 600 mg loading dose on Day 8, followed by a weekly dose of 300 mg from Day 15 to Day 50. PK parameters included Geometric Mean Ratios (GMR) of $AUC_{last}$ (area under the plasma concentration-time curve from time zero to the time of the last quantifiable concentration) and $C_{max}$ (maximum observed plasma concentration) measured at Day 1 and Day 36, while efficacy assessments included changes in Eczema Area and Severity Index (EASI) scores (scale 0-72).

Results:

A total of 14 patients were enrolled in the study (baseline mean EASI score [SD]=29.2 [14.2]), and 13 completed the study. GMRs and 90% confidence intervals for both $AUC_{last}$ and $C_{max}$ (Table 10) indicate no meaningful effect of dupilumab on the PK of midazolam, omeprazole, S-warfarin or caffeine. Based on a slight increase in metoprolol exposure, blockade of IL-4/IL-13 signaling by dupilumab may have a small numerical effect on the activity of CYP2D6, considered to be of little to no clinical relevance. A total of 3 patients had at least one adverse event (AE); there was 1 serious AE leading to treatment discontinuation (systemic inflammatory response syndrome). Mean EASI (SD) scores decreased by 59.3% (37.6) and 87.2% (13.4) at Days 35 and 50, respectively.

TABLE 10

Pharmacokinetic Geometric Mean Ratios (Day 36/Day 1) for all analytes

| Analyte | Pharmacokinetic parameter | Geometric Mean Ratio | 90% CI |
|---|---|---|---|
| midazolam, | $C_{max}$ | 1.13 | 0.93-1.36 |
| n = 13 | $AUC_{last}$ | 0.98 | 0.89-1.09 |
| omeprazole, | $C_{max}$ | 0.98 | 0.83-1.15 |
| n = 13 | $AUC_{last}$ | 1.00 | 0.88-1.12 |
| warfarin, | $C_{max}$ | 0.96 | 0.83-1.11 |
| n = 13 | $AUC_{last}$ | 0.90 | 0.83-0.98 |
| caffeine, | $C_{max}$ | 1.05 | 0.95-1.17 |
| n = 12 | $AUC_{last}$ | 1.12 | 0.87-1.45 |
| metoprolol, | $C_{max}$ | 1.22 | 1.05-1.41 |
| n = 13 | $AUC_{last}$ | 1.29 | 1.10-1.51 |

90% CI, 90% confidence interval;
$AUC_{last}$, area under the plasma concentration-time curve from time zero to the time of the last quantifiable concentration;
$C_{max}$, maximum observed plasma concentration Conclusions:

This study showed that blockade of IL-4/IL-13 signaling by dupilumab through IL-4Rα does not have a meaningful effect on the activity of CYP3A, CYP2C19, CYP2C9, CYP1A2 or CYP2D6 in adult patients with moderate to severe AD. Consistent with previous studies, dupilumab had an acceptable safety profile and provided substantial clinical benefit to patients with AD.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method of reducing pruritus or improving at least one atopic dermatitis (AD)-associated parameter comprising:
   (a) selecting a patient with AD, wherein the patient has a history of inadequate response or intolerance to a systemic immunosuppressant and/or wherein therapy with a systemic immunosuppressant is inadvisable; and
   (b) administering a therapeutically effective amount of a pharmaceutical composition comprising an interleukin-4 receptor (IL-4R) inhibitor in combination with a topical corticosteroid (TCS) to the patient in need thereof, wherein the IL-4R inhibitor is an antibody or antigen-binding fragment thereof that specifically binds IL-4R, wherein the antibody or antigen-binding fragment thereof comprises the heavy chain complementarity determining regions (HCDRs) of a heavy chain variable region (HCVR) comprising the amino acid sequence of SEQ ID NO: 1 and the light chain complementarity determining regions (LCDRs) of a light chain variable region (LCVR) comprising the amino acid sequence of SEQ ID NO: 2.

2. The method of claim 1, wherein the patient has one or more characteristics selected from the group consisting of:
   (i) the patient has a baseline Investigator's Global Assessment (IGA) score=4;
   (ii) the patient has a baseline IGA score ≥3;
   (iii) the patient is a candidate for systemic therapy; (iv) the patient has disease that is uncontrolled by topical AD therapy;
   (v) the patient has a documented history of inadequate response to topical AD therapy or for whom topical therapy is inadvisable due to adverse side effects or safety risks;
   (vi) the patient has been previously treated with a medication or procedure selected from the group consisting of a topical corticosteroid, a topical calcineurin inhibitor, an anti-histamine, an emollient, a dermatological therapeutic, a systemic glucocorticoid, a non-steroidal systemic immunosuppressant, cyclosporine A, azathioprine, ultraviolet (UV) light therapy, and phototherapy; and
   (vii) the patient, prior to or at the time of administration of the IL-4R inhibitor, has or is diagnosed with a disease or disorder selected from the group consisting of food allergy, asthma, seasonal allergy, allergic rhinitis, house dust allergy, and allergic conjunctivitis.

3. The method of claim 1, wherein the systemic immunosuppressant is selected from the group consisting of cyclosporine A (CSA), methotrexate, mycophenolate mofetil, azathioprine, systemic corticosteroids, and interferon-gamma.

4. The method of claim 3, wherein the systemic immunosuppressant is CSA.

5. The method of claim 4, wherein the patient has no prior exposure to CSA, and CSA therapy is inadvisable due to a condition selected from the group consisting of medical contraindications, hypersensitivity to CSA or excipients, use of a concomitant medication prohibited with CSA, increased susceptibility to CSA-induced renal damage, increased susceptibility to CSA-induced liver damage, and increased risk of serious infections.

6. The method of claim 4, wherein the patient is previously exposed to CSA, and CSA therapy is inadvisable due to a condition selected from the group consisting of intolerance, unacceptable toxicity, inadequate response, requirement for CSA at a dose >5 mg/kg/day of the patient's body weight, and requirement of CSA administration for a duration >1 year.

7. The method of claim 1, wherein the IL-4R inhibitor is administered at a dose of about 50-about 600 mg.

8. The method of claim 7, wherein the IL-4R inhibitor is administered at a dose of about 300 mg.

9. The method of claim 1, wherein the IL-4R inhibitor is administered at an initial dose followed by one or more secondary doses, wherein each secondary dose is administered 1 to 4 weeks after the immediately preceding dose.

10. The method of claim 9, wherein the initial dose comprises about 50-about 600 mg of the IL-4R inhibitor.

11. The method of claim 10, wherein each secondary dose comprises about 25-about 400 mg of the IL-4R inhibitor.

12. The method of claim 9, wherein the initial dose comprises about 600 mg of the IL-4R inhibitor, and each secondary dose comprises about 300 mg of the IL-4R inhibitor.

13. The method of claim 12, wherein each secondary dose is administered one week after the immediately preceding dose.

14. The method of claim 12, wherein each secondary dose is administered 2 weeks after the immediately preceding dose.

15. The method of claim 1, wherein administration of the IL-4R inhibitor results in improvement of an AD-associated parameter selected from the group consisting of:
(a) a decrease from baseline in Eczema Area and Severity Index (EAST) score of at least 75%;
(b) a decrease from baseline in Pruritus Numeric Rating Scale (NRS) score of at least 45%;
(c) a decrease from baseline in Scoring Atopic Dermatitis (SCORAD) score of at least 50%;
(d) a decrease from baseline in Investigator's Global Assessment (IGA) score of ≥2 points; and
(e) a decrease from baseline in NRS score of ≥3 points.

16. The method of claim 1, wherein administration of the IL-4R inhibitor results in an improvement in at least one patient-related outcome selected from the group consisting of Global Individual Signs Score (GISS), Patient Oriented Eczema Measure (POEM), Patient-assessed Hospital Anxiety and Depression Scale (HADS), and Patient-reported Dermatology Life Quality Index (DLQI).

17. The method of claim 1, wherein administration of the IL-4R inhibitor results in a decrease in the number of flares or exacerbations in the patient.

18. The method of claim 1, wherein the IL-4R inhibitor is administered subcutaneously.

19. The method of claim 1, wherein the IL-4R inhibitor is administered in combination with an additional therapeutic agent or therapy, wherein the second therapeutic agent or therapy is selected from the group consisting of calcineurin inhibitors and emollients.

20. The method of claim 1, wherein the TCS is selected from the group consisting of low-potency TCS, medium-potency TCS, and high-potency TCS.

21. The method of claim 20, wherein the amount of TCS administered to the patient is gradually reduced following administration of the first dose of the IL-4R inhibitor.

22. The method of claim 21, wherein the amount of TCS administered to the patient is reduced by least about 20% by 4 weeks following administration of the first dose of the IL-4R inhibitor.

23. The method of claim 21, wherein the amount of TCS administered to the patient is reduced by about 50% by 4 weeks following administration of the first dose of the IL-4R inhibitor.

24. The method of claim 1, wherein the antibody or antigen-binding fragment prevents the interaction of IL-4 and/or IL-13 with a type 1 or type 2 IL-4 receptor.

25. The method of claim 24, wherein the antibody or antigen-binding fragment thereof prevents the interaction of IL-4 with both type 1 and type 2 IL-4 receptors.

26. The method of claim 1, wherein the antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO: 3; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 6; the LCDR2 comprises the amino acid sequence of SEQ ID NO: 7; and the LCDR3 comprises the amino acid sequence of SEQ ID NO: 8.

27. The method of claim 26, wherein the HCVR comprises the amino acid sequence of SEQ ID NO: 1 and the LCVR comprises the amino acid sequence of SEQ ID NO: 2.

28. The method of claim 1, wherein the antibody or antigen-binding fragment thereof comprises a heavy chain comprising the amino acid sequence of SEQ ID NO: 9 and a light chain comprising the amino acid sequence of SEQ ID NO: 10.

29. The method of claim 1, wherein the IL-4R inhibitor is dupilumab or a bioequivalent thereof.

30. A method for treating moderate-to-severe or severe atopic dermatitis (AD) or improving an AD-associated parameter, the method comprising:
(a) selecting a patient with moderate-to-severe or severe AD, wherein the patient has an attribute selected from the group consisting of:
(i) the patient has a baseline IGA score=4;
(ii) the patient has a baseline IGA score ≥3;
(iii) the patient is between 6 and 18 years of age;
(iv) the patient has disease that is uncontrolled by topical AD therapy;
(v) the patient has a documented history of inadequate response to topical AD therapy or for whom topical therapy is inadvisable due to adverse side effects or safety risks;
(vi) the patient has been previously treated with a medication or procedure selected from the group consisting of a topical corticosteroid, a topical calcineurin inhibitor, an anti-histamine, an emollient, a dermatological therapeutic, a systemic glucocorticoid, a non-steroidal systemic immunosuppressant, cyclosporine A, azathioprine, ultraviolet (UV) light therapy, and phototherapy; and
(vii) the patient has a concomitant disease or disorder selected from the group consisting of food allergy, asthma, seasonal allergy, allergic rhinitis, house dust allergy, and allergic conjunctivitis; and
(b) administering one or more doses of a therapeutically effective amount of an IL-4R inhibitor to the patient in need thereof, wherein the IL-4R inhibitor is an antibody or antigen-binding fragment thereof that specifically binds IL-4R, wherein the antibody or antigen-binding fragment thereof comprises the heavy chain complementarity determining regions (HCDRs) of a heavy chain variable region (HCVR) comprising the amino acid sequence of SEQ ID NO: 1 and the light chain complementarity determining regions (LCDRs) of a light chain variable region (LCVR) comprising the amino acid sequence of SEQ ID NO: 2.

31. The method of claim 30, wherein the patient has severe AD, is between 6 and 11 years of age, has a baseline IGA score=4, and has disease that is uncontrolled by topical AD therapy.

32. The method of claim 30, wherein each dose of the IL-4R inhibitor comprises 1, 2, 3, 4, or 5 mg/kg of the patient's body weight, and wherein each dose is administered 1-4 weeks after the immediately preceding dose.

33. The method of claim 30, wherein each dose comprises about 20-about 600 mg of the IL-4R inhibitor, and wherein each dose is administered 1-4 weeks after the immediately preceding dose.

34. The method of claim 30, wherein the administration of the IL-4R inhibitor leads to an effect selected from the group consisting of:
(i) more than 30% reduction from baseline in EASI score by week 2 after administration of the first dose of the IL-4R inhibitor;
(ii) more than 50% reduction from baseline in pruritus NRS; and (iii) a reduction from baseline in IGA score to achieve an IGA score of 0 or 1 by week 12 after administration of the first dose of the IL-4R inhibitor.

35. The method of claim 30, wherein the IL-4R inhibitor is administered in combination with a second therapeutic agent selected from the group consisting of a topical corticosteroid, a topical calcineurin inhibitor, an anti-histamine, an emollient, an anti-bacterial therapeutic, and a therapeutic agent for obstructive airway disease.

36. The method of claim 30, wherein the antibody or antigen-binding fragment prevents the interaction of IL-4 and/or IL-13 with a type 1 or type 2 IL-4 receptor.

37. The method of claim 36, wherein the antibody or antigen-binding fragment thereof prevents the interaction of IL-4 with both type 1 and type 2 IL-4 receptors.

38. The method of claim 30, wherein the antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO: 3; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 6; the LCDR2 comprises the amino acid sequence of SEQ ID NO: 7; and the LCDR3 comprises the amino acid sequence of SEQ ID NO: 8.

39. The method of claim 38, wherein the HCVR comprises the amino acid sequence of SEQ ID NO: 1 and the LCVR comprises the amino acid sequence of SEQ ID NO: 2.

40. The method of claim 30, wherein the antibody or antigen-binding fragment thereof comprises a heavy chain comprising the amino acid sequence of SEQ ID NO: 9 and a light chain comprising the amino acid sequence of SEQ ID NO: 10.

41. The method of claim 30, wherein the IL-4R inhibitor is dupilumab or a bioequivalent thereof.

42. The method of claim 7, wherein the IL-4R inhibitor is administered at a dose of about 100 mg.

43. The method of claim 18, wherein the IL-4R inhibitor is contained in a container selected from the group consisting of a syringe, a pen delivery device, a vial, and an autoinjector.

44. The method of claim 43, wherein the IL-4R inhibitor is contained in a syringe.

45. The method of claim 43, wherein the IL-4R inhibitor is contained in a pen delivery device.

46. The method of claim 45, wherein the pen delivery device is prefilled.

47. The method of claim 43, wherein the IL-4R inhibitor is contained in a vial.

48. The method of claim 43, wherein the IL-4R inhibitor is contained in an autoinjector.

49. The method of claim 30, wherein the IL-4R inhibitor is administered subcutaneously.

50. The method of claim 49, wherein the IL-4R inhibitor is contained in a container selected from the group consisting of a syringe, a pen delivery device, a vial, and an autoinjector.

51. The method of claim 50, wherein the IL-4R inhibitor is contained in a syringe.

52. The method of claim 50, wherein the IL-4R inhibitor is contained in a pen delivery device.

53. The method of claim 52, wherein the pen delivery device is prefilled.

54. The method of claim 50, wherein the IL-4R inhibitor is contained in a vial.

55. The method of claim 50, wherein the IL-4R inhibitor is contained in an autoinjector.

56. The method of claim 33, wherein each dose comprises about 100 mg of the IL-4R inhibitor.

57. The method of claim 33, wherein each dose comprises about 200 mg of the IL-4R inhibitor.

* * * * *